US008841068B2

(12) United States Patent
Smith et al.

(10) Patent No.: US 8,841,068 B2
(45) Date of Patent: Sep. 23, 2014

(54) HUMAN IMMUNODEFICIENCY VIRUS ANTIVIRAL SCREENING ASSAY INVOLVING THE DETECTION OF CEM15 EXPRESSION

(75) Inventors: Harold C. Smith, Rochester, NY (US); Xia Jin, Fairpoint, NY (US); Andrew Brooks, New York, NY (US)

(73) Assignee: University of Rochester, Rochester, NY (US)

( * ) Notice: Subject to any disclaimer, the term of this patent is extended or adjusted under 35 U.S.C. 154(b) by 1540 days.

(21) Appl. No.: 11/816,063

(22) PCT Filed: Feb. 13, 2006

(86) PCT No.: PCT/US2006/004920
§ 371 (c)(1),
(2), (4) Date: Jun. 24, 2009

(87) PCT Pub. No.: WO2007/126402
PCT Pub. Date: Nov. 8, 2007

(65) Prior Publication Data
US 2010/0016253 A1    Jan. 21, 2010

Related U.S. Application Data

(60) Provisional application No. 60/652,177, filed on Feb. 11, 2005.

(51) Int. Cl.
*C12Q 1/70* (2006.01)
(52) U.S. Cl.
CPC ..................................... *C12Q 1/703* (2013.01)
USPC ............................................................ 435/5
(58) Field of Classification Search
None
See application file for complete search history.

(56) References Cited

U.S. PATENT DOCUMENTS

| | | |
|---|---|---|
| 2003/0013844 A1 | 1/2003 | Zhang et al. |
| 2004/0009951 A1 | 1/2004 | Malim et al. |
| 2004/0234956 A1 | 11/2004 | Kabat et al. |

FOREIGN PATENT DOCUMENTS

WO    WO 2007/126402    11/2007

OTHER PUBLICATIONS

Strongin, W., 1992, "Sensitivity, specificity, and predictive value of diagnostic tests: definitions and clinical applications", in Laboratory Diagnosis of Viral Infections, Lennette, E. H., ed., Marcel Dekker, Inc., New York, New York, pp. 211-219.*
Kao, S., et al., Nov. 2003, The human immunodeficiency virus type 1 Vif protein reduces intracellular expression and inhibits packaging of APOBEC3G (CEM15), a cellular inhibitor of virus infectivity, J. Virol. 77(21):11398-11407.*

An, P., G. Bleiber, P. Duggal, G. Nelson, M. May, B. Mangeat, I. Alobwede, D. Trono, D. Vlahov, S. Donfield, J. J. Goedert, J. Phair, S. Buchbinder, S. J. O'Brien, A. Telenti, and C. A. Winkler. 2004. APOBEC3G genetic variants and their influence on the progression to AIDS. J Virol 78:11070-6.
Anant, S. and N.O. Davidson, Molecular mechanisms of apolipoprotein B mRNA editing. *Curr Opin Lipidol.* 12(2):159-65 (2001).
Anant, S. G., Giannoni, F., Antic, D., DeMaria, C. T., Keene, J. D., Brewer, G. and Davidson, N. O. AU-rich RNA binding proteins Hel-N1 and AUF1 bind apolipoprotein B mRNA and inhibit post-transcriptional C to U editing. *Nucleic Acids Symp.* Ser. 36, 115-118 (1997).
Anant, S., et al., ARCD-1, an apobec-1-related cytidine deaminase, exerts a dominant negative effect on C to U RNA editing. *Am J Physiol Cell Physiol.* 281:C1904-16 (2001).
Anant, S., et al., Evolutionary origins of the mammalian apolipoproteinB RNA editing enzyme, apobec-1: structural homology inferred from analysis of a cloned chicken small intestinal cytidine deaminase. *Biol Chem.* 379:1075-81 (1998).
Anant, S., MacGinnitie, A.J. and Davidson, N.O. APOBEC-1, the catalytic subunit of the mammalian apoB B mRNA editing enzyme, is a novel RNA-binding protein. *J. Biol. Chem.* 270, 14762-14767 (1995).
Andersson, T., C. Furebring, C.A. Borrebaeckand S. Pettersson, Temporal expression of a V(H) promoter-Cmu transgene linked to the IgH HS1,2 enhancer. *Mol Immunol*, 36(1):19-29 (1999).
Arakawa, H., J. Hauschildand J.M. Buerstedde, Requirement of the activation-induced deaminase (AID) gene for immunoglobulin gene conversion. *Science*, 295(5558): p. 1301-6 (2002).
Arulampalam, V., C. Furebring, A. Samuelsson, U. Lendahl, C. Borrebaeck, I. Lundkvistand S. Pettersson, Elevated expression levels of an Ig transgene in mice links the IgH 3' enhancer to the regulation of IgH expression. *Int Immunol.* 8(7):1149-57 (1996).
Baba, T. W., V. Liska, R. Hofmann-Lehmann, J. Vlasak, W. Xu, S. Ayehunie, L. A. Cavacini, M. R. Posner, H. Katinger, G. Stiegler, B. J. Bernacky, T. A. Rizvi, R. Schmidt, L. R. Hill, M. E. Keeling, Y. Lu, J. E. Wright, T. C. Chou, and R. M. Ruprecht. 2000. Human neutralizing monoclonal antibodies of the IgG1 subtype protect against mucosal simian-human immunodeficiency virus infection. Nat Med 6:200-6.
Backus, J.W. and Smith, H.C. Apolipoprotein B mRNA sequences 3' of the editing site are necessary and sufficient for editing and editosome assembly. *Nucleic Acids Res.* 19(24):6781-6786 (1991).

(Continued)

*Primary Examiner* — Jeffrey S. Parkin
(74) *Attorney, Agent, or Firm* — Riverside Law LLP

(57) ABSTRACT

The present invention provides compositions and methods related to determining the severity of viral infections and identifying antiviral agents. In certain embodiments, the invention comprises determining the expression level of APOBEC-1 related proteins, where the expression level of APOBEC-1 related proteins is an indicator for disease severity and/or effectiveness of a potential antiviral agent. In one embodiment, the present invention provides for a method of screening for an antiviral agent.

4 Claims, 12 Drawing Sheets

(56) References Cited

OTHER PUBLICATIONS

Backus, J.W. and Smith, H.C. Specific 3' sequences flanking a minimal apoB mRNA editing 'cassette' are critical for efficient editing in vitro. *Biochim. Biophys. Acta* 1217, 65-73 (1994).

Backus, J.W. and Smith, H.C. Three distinct RNA sequence elements are required for efficient apoB RNA editing in vitro. *Nucleic Acids Res.* 22, 6007-6014 (1992).

Backus, J.W., Schock, D. and Smith, H.C. Only cytidines 5' of the apoB mRNA mooring sequence are edited. *Biochim. Biophys. Acta* 1219(1):1-14 (1994).

Barat, C., V. Lullien, O. Schatz, G. Keith, M.T. Nugeyre, F. Gruninger-Leitch, F. Barre-Sinoussi, S.F. LeGrice, and J.L. Darlix, HIV-1 reverse transcriptase specifically interacts with the anticodon domain of its cognate primer tRNA. *Embo J.* 8(11):3279-85 (1989).

Baum, C.L., Teng, B.B. and Davidson, N.O. Apolipoprotein B messenger RNA editing in the rat liver: modulation by fasting and refeeding a high carbohydrate diet. *J. Biol. Chem.* 265, 19263-19270 (1990).

Berkhout, B., A.T. Das, and N. Beerens, HIV-1 RNA editing, hypermutation, and error-prone reverse transcription. *Science* 292(5514):7 (2001).

Bernstein, E., A.M. Denliand G.J. Hannon, The rest is silence. *RNA* 7(11):1509-21 (2001).

Betts L., Xiang S, Short SA, Wolfenden R, Carter CW Cytidine deaminase. The 2.3 A crystal structure of an enzyme: transition-state analog complex. *J Mol Biol.* 235, 635-56 (1994).

Bishop, K. N., R. K. Holmes, A. M. Sheehy, N. O. Davidson, S. J. Cho, and M. H. Malim. 2004. Cytidine deamination of retroviral DNA by diverse APOBEC proteins. Curr Biol 14:1392-6.

Blanc, V., et al. Mutagenesis of apobec-1 complementation factor reveals distinct domains that modulate RNA binding, protein-protein interaction with apobec-1, and complementation of C to U RNA-editing activity. *J Biol Chem.* 276(49):46386-93 (2001).

Blanc. V., Navaratnam, N., Henderson, J.O., Anant, S., Kennedy, S., Jarmuz, A., Scott, J. and Davidson, N.O. Identification of GR-RBP as an apo B mRNA binding protein that interacts with both apobec-1 and with apobec-1 complementation factor (ACF) to modulate C to U editing. *J. Biol. Chem.* 276(13):10272-10283 (2001).

Bogerd, H. P., B. P. Doehle, H. L. Wiegand, and B. R. Cullen. 2004. A single amino acid difference in the host APOBEC3G protein controls the primate species specificity of HIV type 1 virion infectivity factor. Proc Natl Acad Sci U S A 101:3770-4.

Borrow, P., H. Lewicki, B. H. Hahn, G. M. Shaw, and M. B. Oldstone. 1994. Virus-specific CD8+ cytotoxic T-lymphocyte activity associated with control of viremia in primary human immunodeficiency virus type 1 infection. Journal of Virology 68:6103-10.

Borrow, P., H. Lewicki, X. Wei, M. S. Horwitz, N. Peffer, H. Meyers, J. A. Nelson, J. E. Gairin, B. H. Hahn, M. B. Oldstone, and G. M. Shaw. 1997. Antiviral pressure exerted by HIV-1-specific cytotoxic T lymphocytes (CTLs) during primary infection demonstrated by rapid selection of CTL escape virus. Nature Medicine 3:205-11.

Bostrom, K., Garcia, Z., Poksay, K. S., Johnson, D. F., Lusis, A. J. and Innerarity, T. L. Apolipoprotein B mRNA editing. Direct determination of the edited base and occurrence in non-apolipoprotein B producing cell lines. *J. Biol. Chem.* 265, 22446-22452 (1990).

Bouhamdan, M., S. Benichou, F. Rey, J.M. Navarro, I. Agostini, B. Spire, J. Camonis, G. Slupphaug, R. Vigne, R. Benarous, and J. Sire, Human immunodeficiency virus type 1 Vpr protein binds to the uracil DNA glycosylase DNA repair enzyme. *J Virol.* 70(2):697-704 (1996).

Bourara, K., S. Litvak, and A. Araya, Generation of G-to-A and C-to-U changes in HIV-1 transcripts by RNA editing. *Science.* 289(5484):1564-6 (2000).

Bowie, J.U., R. Luthy, and D. Eisenberg, A method to identify protein sequences that fold into a known three-dimensional structure. *Science.* 253(5016):164-70 (1991).

Bransteitter, R., P. Pham, M.D. Scharff, and M.F. Goodman, Activation-induced cytidine deaminase deaminates deoxycytidine on single-stranded DNA but requires the action of RNase. *Proc Natl Acad Sci U S A.* 100(7): p. 4102-7 (2003).

Bross, L., M. Muramatsu, K. Kinoshita, T. Honjoand H. Jacobs, DNA Double-Strand Breaks: Prior to but not Sufficient in Targeting Hypermutation. *J Exp Med* 195(9):1187-1192 (2002).

Buchbinder, S., and Vittinghoff, E. 1999. HIV-infected long-term nonprogressors: epidemiology, mechanisms of delayed progression, and clinical and research implications. *Microbes and Infection* 1:1113-1120.

Burley, S.K. An overview of structural genomics. *Nature Struct. Biol.* 7, 932-934 (2000).

Camaur, D. and D. Trono, Characterization of human immunodeficiency virus type 1 Vif particle, *J Virol..* 70(9):6106-11 (1996).

Cao, Y., L. Qin, L. Zhang, J. Safrit, and D. D. Ho. 1995. Virologic and immunologic characterization of long-term survivors of human immunodeficiency virus type 1 infection. N. Engl J Med 332:201-8.

Carlow, D.C., A.A. Smith, C.C. Yang, S.A. Short, and R. Wolfenden, Major contribution of a carboxymethyl group to transition-state stabilization by cytidine deaminase: mutation and rescue. *Biochemistry.* 34(13):4220-4 (1995).

Carrington, M., G. W. Nelson, M. P. Martin, T. Kissner, D. Vlahov, J. J. Goedert, R. Kaslow, S. Buchbinder, K. Hoots, and S. J. O'Brien. 1999. HLA and HIV-1: heterozygote advantage and B*35-Cw*04 disadvantage. Science 283:1748-52.

Cartegni, L., S.L. Chewand A.R. Krainer, Listening to silence and understanding nonsense: exonic mutations that affect splicing. Nat Rev Genet. 3(4):285-98 (2002).

Casellas, R., A. Nussenzweig, R. Wuerffel, R. Pelanda, A. Reichlin, H. Suh, X.F. Qin, E. Besmer, A. Kenter, K. Rajewsky and M.C. Nussenzweig, Ku80 is required for immunoglobulin isotype switching. *Embo J* 17(8):2404-11 (1998).

Cattaneo, R. Biased (A→I) hypermutation of animal RNA virus genomes. *Curr Opin Genet Dev* 4(6): 895-900 (1994).

Chaudhuri, J., M. Tian, C. Khuong, K. Chua, E. Pinaud, and F.W. Alt, Transcription-targeted DNA deamination by the AID antibody diversification enzyme. *Nature.* 422(6933):726-30 (2003).

Chen, J., R. Lansford, V. Stewart, F. Youngand F.W. Alt, RAG-2-deficient blastocyst complementation: an assay of gene function in lymphocyte development. *Proc Natl Acad Sci U S A.* 90(10): 4528-32 (1993).

Chen, R., H. Wang, and L.M. Mansky, Roles of uracil-DNA glycosylase and dUTPase in virus replication. *J Gen Virol.* 83(Pt 10):2339-45 (2002).

Chen, S.H., Habib, G., Yang, C Y., Gu, Z.W., Lee, BR., Weng, S.A., Silberman, S.R., Cai, S.J., Deslypere, J.P., Rosseneu, M., Gotto, A.M.J.R., Li, W.H. and Chan, L. Apolipoprotein B-48 is the product of a messenger RNA with an organ-specific in-frame stop codon. *Science* 238, 363-366 (1987).

Cho et al., APOBEC3F and APOBEC3G mRNA Levels Do Not Correlate with Human Immunodeficiency Virus, Type 1 Plasma Viremia or CDR T-Cell Count, *Journal of Virology*, vol. 80, No. 4: pp. 2069-2072, Feb. 2006.

Chothia, C. and A.M. Lesk, The relation between the divergence of sequence and structure in proteins, *Embo J.* 5(4):823-6 (1986).

Chua, K.F., F.W. Altand J.P. Manis, The Function of AID in Somatic Mutation and Class Switch Recombination: Upstream or Downstream of DNA Breaks. *J Exp Med.* 195(9): F37-41 (2002).

Clerici, M., N. I. Stocks, R. A. Zajac, R. N. Boswell, D. R. Lucey, C. S. Via, and G. M. Shearer. 1989. Detection of three distinct patterns of T helper cell dysfunction in asymptomatic, human immunodeficiency virus-seropositive patients. Independence of CD4+ cell numbers and clinical staging. The Journal of Clinical Investigation 84:1892-9.

Courcoul, M., C. Patience, F. Rey, D. Blanc, A. Harmache, J. Sire, R. Vigne, and B. Spire, Peripheral blood mononuclear cells produce normal amounts of defective Vif- human immunodeficiency virus type 1 particles which are restricted for the preretrotranscription steps. *J Virol.* 69(4):2068-74 (1995).

Dance, G. S. C., Sowden, M. P., Yang, Y. and Smith, H. C. APOBEC-1 dependent cytidine to uridine editing of apolipoprotein B RNA in yeast. *Nucleic Acids Res.* 28, 424-429 (2000).

(56) References Cited

OTHER PUBLICATIONS

Dance, G.S.C., Beemiller, P., Yang, Y., Van Mater, D. Mian, S.I. and Smith, H.C. Identification of the yeast cytidine deaminase CDD1 as an orphan C to U RNA editase. *Nucleic Acids Res.* 29, 1772-1780 (2001).

Dance, G.S.C., Sowden,M.P., Cartegni, L., Cooper, E., Krainer, A.R., Smith, H.C., Two proteins essential for apolipoprotein B mRNA editing are expressed from a single gene through alternative splicing. *J. Biol. Chem.*, 277:12703-09 (2002).

Davidson, N.O., Powell, L.M., Wallis, S.C. and Scott, J. Thyroid hormone modulates the introduction of a stop codon in rat liver apolipoprotein B messenger RNA. *J. Biol. Chem.* 263, 13482-13485 (1988).

Deacon, N. J., A. Tsykin, A. Solomon, K. Smith, M. Ludford-Menting, D. J. Hooker, D. A.McPhee, A. L. Greenway, A. Ellett, C. Chatfield, and et al. 1995. Genomic structure of an attenuated quasi species of HIV-1 from a blood transfusion donor and recipients. Science 270:988-91.

Dettenhofer, M., S. Cen, B.A. Carlson, L. Kleiman, and X.F. Yu, Association of human immunodeficiency virus type 1 Vif with RNA and its role in reverse transcription. *J Virol*, 74(19):8938-45 (2000).

Doi, T., K. Kinoshita, M. Ikegawa, M. Muramatsu, and T. Honjo, Inaugural Article: De novo protein synthesis is required for the activation-induced cytidine deaminase function in class-switch recombination. *Proc Natl Acad Sci U S A* 100(5):2634-8 (2003).

Driscoll, D. M., Lakhe-Reddy, S., Oleksa, L. M. and Martinez, D. Induction of RNA editing at heterologous sites by sequences in apolipoprotein B mRNA. *Mol. Cell. Biol.* 13, 7288-7294 (1993).

Driscoll, D.M. and E. Casanova, Characterization of the apolipoprotein B mRNA editing activity in enterocyte extracts. *J Biol Chem.* 265(35):21401-3 (1990).

Economidis, I.V. and T. Pederson, In vitro assembly of a pre-messenger ribonucleoprotein. *Proc Natl Acad Sci U S A*, 80(14):4296-300 (1983).

Egebjerg, J., Kukekov, V. and Heinemann, S. F. Intron sequence directs RNA editing of the glutamate receptor subunit GluR2 coding sequence. *Proc. Natl. Acad. Sci. U.S.A.* 91, 10270-10274 (1994).

Ehrenstein, M.R. and M.S. Neuberger Deficiency in Msh2 affects the efficiency and local sequence specificity of immunoglobulin class-switch recombination: parallels with somatic hypermutation. *Embo J*, 18(12): p. 3484-90 (1999).

Eisenberg, D., R. Luthy, and J.U. Bowie, VERIFY3D: assessment of protein models with three-dimensional profiles. *Methods Enzymol.* 277:396-404 (1997).

Faham, M., S. Baharloo, S. Tomitaka, J. DeYoungand N.B. Freimer, Mismatch repair detection (MRD): high-throughput scanning for DNA variations. Hum Mol *Genet.* 10(16):1657-64 (2001).

Fauci, A. S. 1993. Multifactorial nature of human immunodeficiency virus disease: implications for therapy. Science 262:1011-8.

Fisher, A.G., B. Ensoli, L. Ivanoff, M. Chamberlain, S. Petteway, L. Ratner, R.C. Gallo, and F. Wong-Staal, *The sor gene of HIV-1 is required for efficient virus transmission in vitro. Science.* 237(4817):888-93 (1987).

Fisher, C. L. and Pei, K. P. Modification of a PCR-based site-directed mutagenesis method. *BioTechniques* 23, 570-574 (1997).

Fugmann, S.D. and Schatz, D.G. Immunology. One AID to unite them all. *Science.* 295:1244-5 (2002).

Funahashi, T., Giannoni, F., DePaoli, A.M., Skarosi, S.F. and Davidson, N.O. Tissue-specific, developmental and nutritional regulation of the gene encoding the catalytic subunit of the rat apoB mRNA editing enzyme: functional role in the modulation of apoB mRNA editing. *J. Lipid Res.* 36:414-428 (1995).

Gaddis, N. C., A. M. Sheehy, K. M. Ahmad, C. M. Swanson, K. N. Bishop, B. E. Beer, P. A. Marx, F. Gao, F. Bibollet-Ruche, B. H. Hahn, and M. H. Malim. 2004. Further investigation of simian immunodeficiency virus Vif function in human cells. J Virol 78:12041-6.

Gaddis, N.C., Certova, E., Sheehy, A.M., Henderson, L.E. and Malim, M.H. Comprehensive investigation of the molecular defect in vif-deficient human immunodeficiency virus type 1 virions. *J. Virol.* 77(10): 5810-5820 (2003).

Gerber, A., H. Grosjean, T. Melcher, and W. Keller Tad1p, a yeast tRNA-specific adenosine deaminase, is related to the mammalian pre-mRNA editing enzymes ADAR1 and ADAR2. *Embo J.* 17(16):4780-9 (1998).

Gerber, A.P. and Keller, W. RNA editing by base deamination: more enzymes, more targets, new mysteries. *TIBS* 26:376-384 (2001).

Gerber, A.P. and W. Keller An adenosine deaminase that generates inosine at the wobble position of tRNAs. *Science* 286(5442):1146-9 (1999).

Giannoni, F., Bonen, D. K., Funahashi, T., Hadjiagapiou, C., Burant, C. F. and Davidson, N. O. Complementation of apolipoprotein B mRNA editing by human liver accompanied by secretion of apolipoprotein B48. *J. Biol. Chem.* 269:5932-5936 (1994).

Giannoni, F., Chou, S.C., Skarosi, S.F., Verp, M.S., Field, F.J., Coleman, R.A. and Davidson, N.O. Developmental regulation of the catalytic subunit of the apoB mRNA editing enzyme (APOBEC-1) in human small intestine. *J. Lipid Res.* 36:1664-1675 (1995).

Gott, J. M. and Emeson, R. B. Functions and mechanisms of RNA editing. Annu. Rev. Genet. 34, 499-531 (2000).

Goulder, P. J., R. E. Phillips, R. A. Colbert, S. McAdam, G. Ogg, M. A. Nowak, P. Giangrande, G. Luzzi, B. Morgan, A. Edwards, A. J. McMichael, and S. Rowland-Jones. 1997. Late escape from an immunodominant cytotoxic T-lymphocyte response associated with progression to AIDS. Nat Med 3:212-7.

Goulder, P. J., Y. Tang, S. I. Pelton, and B. D. Walker. 2000. HLA-B57-restricted cytotoxic T-lymphocyte activity in a single infected subject toward two optimal epitopes, one of which is entirely contained within the other. Journal of Virology 74:5291-9.

Greeve, J., Altkemper, I., Dieterich, J-H., Greten, H. and Winder, E. (1993) Apolipoprotein B mRNA editing in 12 different mammalian species: hepatic expression is reflected in low concentrations of apoB-containing plasma lipoproteins. *J. Lipid Res.* 34:1367-1383 (2000).

Greeve, J., Lellek, H., Rautenberg, P. and Greten, H. Inhibition of the apolipoprotein B mRNA editing enzyme-complex by hnRNP C1 protein and 40S hnRNP complexes. *Biol. Chem.* 379:1063-1073 (1998).

Hader, S. L., T. W. Hodge, K. A. Buchacz, R. A. Bray, N. S. Padian, A. Rausa, S. A. Slaviniski, and S. D. Holmberg. 2002. Discordance at human leukocyte antigen-DRB3 and protection from human immunodeficiency virus type 1 transmission. J Infect Dis 185:1729-35.

Harris et al., Retroviral Restriction by APOBEC proteins, *Nature*, vol. 4: pp. 868-877, 2004.

Harris, R.S., Bishop, K.N., Sheehy, A.M., Craig, H.M., Petersen-Mahrt, S.K., Watt, I.N., Neuberger, M.S., and Malim, M. H. DNA deamination mediates innate immunity to retroviral infection. *Cell.* 113:803-809 (2003).

Harris, R.S., S.K. Petersen-Mahrt, and M.S. Neuberger, *RNA editing enzyme APOBEC1 and some of its homologs can act as DNA mutators. Mol Cell.* 10(5):1247-53 (2002).

Harris, S. G., Sabio, I., Mayer, E., Steinburg, M. F., Backus, J. W., Sparks, J. D., Sparks, C. E. and Smith, H. C. Extract-specific heterogeneity in high-order complexes containing apolipoprotein B mRNA editing activity and RNA-binding proteins. *J. Biol. Chem.* 268(10):7382-7392 (1993).

Harris, S.G. and Smith, H.C. In vitro apoB mRNA editing activity can be modulated by fasting and refeeding rats with a high carbohydrate diet. *Biochem. Biophys. Res. Commun.* 183(2):899-903 (1992).

Hendel, H., S. Caillat-Zucman, H. Lebuanec, M. Carrington, S. O'Brien, J. M. Andrieu, F. Schachter, D. Zagury, J. Rappaport, C. Winkler, G. W. Nelson, and J. F. Zagury. 1999. New class I and II HLA alleles strongly associated with opposite patterns of progression to AIDS. J Immunol 162:6942-6.

Henzler, T., Harmache, A., Herrmann, H., Spring, H., Suzan, M., Audoly, G., Panek, T. and Bosch, V. Fully functional, naturally occurring and C-terminally truncated variant human immunodeficiency virus (HIV) Vif does not bind to HIV Gag but influences intermediate filament structure. *J. Gen Virol.* 82:561-573 (2001).

(56) References Cited

OTHER PUBLICATIONS

Hersberger, M. and Innerarity, T. L. Two efficiency elements flanking the editing site of cytidine 6666 in the apolipoprotein B mRNA support mooring dependent editing. *J. Biol. Chem.* 273:9435-9442 (1998).

Hersberger, M., Patarroyo-White, S., Arnold, K. S. and Innerarity, T. L. Phylogenetic analysis of the apolipoprotein B mRNA editing region. Evidence for a secondary structure between the mooring sequence and the 3' efficiency element. *J. Biol. Chem.* 274, 34590-34597 (1999).

Higuchi, M., Maas, S., Single, F. N., Hartner, J., Rozov, A., Burnashev, N., Feldmeyer, D., Sprengel, R. and Seeburg, P. H. Point mutation in an AMPA receptor gene rescues lethality in mice deficient in the RNA editing enzyme ADAR2. *Nature* (London) 405:78-81 (2000).

Higuchi, M., Single, F.N., Köhler, M., Sommer, B., Sprengel, R. and Seeburg, P.H. RNA editing of AMPA receptor subunit GluR-B: a base-paired intron-exon structure determines position and efficiency. *Cell* 75:1361-1370 (1993).

Hilleren, P. and R. Parker, mRNA surveillance in eukaryotes: kinetic proofreading of proper translation termination as assessed by mRNP domain organization? *RNA*. 5(6):711-9 (1999).

Hirano, K.I., Young, S.G., Farese, R.V., Ng, J., Sande, E., Warburton, C., Powell-Braxton, L.M. and Davidson, N.O. Targeted disruption of the mouse apobec-1 gene abolishes apoB mRNA editing and eliminates ApoB48. *J. Biol. Chem.* 271, 9887-9890 (1996).

Honjo, T., et al. Molecular Mechanism of Class Switch Recombination: Linkage with Somatic Hypermutation. *Annu Rev Immunol.* 20:165-96 (2002).

Hu, B.T., S.C. Lee, E. Mahn, D.H. Ryanand R.A. Insel, Telomerase is up-regulated in human germinal center B cells in vivo and can be re-expressed in memory B cells activated in vitro. *J Immunol.* 159(3):1068-71 (1997).

Huang, Y., L. Zhang, and D. D. Ho. 1998. Characterization of gag and pol Sequences from Long-Term Survivors of Human Immunodeficiency Virus Type 1 Infection. Virology 240:36.

Hwang, J.T., K.A. Tallman, and M.M. Greenberg, The reactivity of the 2-deoxyribonolactone lesion in single-stranded DNA and its implication in reaction mechanisms of DNA damage and repair. *Nucleic Acids Res*, 27(19):3805-10 (1999).

Inui, Y., Giannoni, F., Funahashi, T. and Davidson, N.O. REPR and complementation factor(s) interact to modulate rat apolipoprotein B mRNA editing in response to alterations in cellular cholesterol flux. *J. Lipid Res.* 35, 1477-1489 (1994).

Jarmuz, A., A. Chester, J. Bayliss, J. Gisbourne, I. Dunham, J. Scott, and N. Navaratnam. 2002. An Anthropoid-Specific Locus of Orphan C to U RNA-Editing Enzymes on Chromosome 22. Genomics 79:285-96.

Jin et al., APOBEC3G/CEM15 (hA3G) mRNA Levels Associate Inversely with Human Immunodeficiency Virus Viremia, *Journal of Virology*, vol. 79, No. 17: pp. 11513-11516, 2005.

Jin, X., G. Ogg, S. Bonhoeffer, J. Safrit, M. Vesanen, D. Bauer, D. Chen, Y. Cao, M. A. Demoitie, L. Zhang, M. Markowitz, D. Nixon, A. McMichael, and D. D. Ho. 2000. An antigenic threshold for maintaining human immunodeficiency virus type 1-specific cytotoxic T lymphocytes. Molecular Medicine 6:803-9.

Johansson E, Mejlhede N, Neuhard J, Larsen S. Crystal structure of the tetrameric cytidine deaminase from *Bacillus subtilis* at 2.0 Å resolution. *Biochem.* 41(8):2563-70 (2002).

Jones, T.A., J.Y. Zou, S.W. Cowan, and Kjeldgaard, Improved methods for building protein models in electron density maps and the location of errors in these models. *Acta Crystallogr A*. 47 ( Pt 2):110-9 (1991).

Kabsch, W., A solution for the best rotation to relate two sets of vectors. Acta. Crystallogr., A32:922-923 (1976).

Kao, S., E. Miyagi, M. A. Khan, H. Takeuchi, S. Opi, R. Goila-Gaur, and K. Strebel. 2004. Production of infectious human immunodeficiency virus type 1 does not require depletion of APOBEC3G from virus-producing cells. Retrovirology 1:27.

Kaslow, R. A., M. Carrington, R. Apple, L. Park, A. Munoz, A. J. Saah, J. J. Goedert, C. Winkler, S. J. O'Brien, C. Rinaldo, R. Detels, W. Blattner, J. Phair, H. Erlich, and D. L. Mann. 1996. Influence of combinations of human major histocompatibility complex genes on the course of HIV-1 infection. Nat Med 2:405-11.

Kataoka, N., Yong, J., Kim, V. N., Velazquez, F., Perkinson, R. A., Wang, F. and Dreyfuss, G. Pre-mRNA splicing imprints mRNA in the nucleus with a novel RNA-binding protein that persists in the cytoplasm. *Mol. Cell* 6:673-682 (2000).

Kaul, R., F. A. Plummer, J. Kimani, T. Dong, P. Kiama, T. Rostron, E. Njagi, K. S. MacDonald, J. J. Bwayo, A. J. McMichael, and S. L. Rowland-Jones. 2000. HIV-1-specific mucosal CD8+lymphocyte responses in the cervix of HIV-1-resistant prostitutes in Nairobi. J Immunol 164:1602-11.

Kaushik, N. and V.N. Pandey, PNA targeting the PBS and A-loop sequences of HIV-1 genome destabilizes packaged tRNA3(Lys) in the virions and inhibits HIV-1 replication. *Virology*. 303(2):297-308 (2002).

Keegan, L.P., A.P. Gerber, J. Brindle, R. Leemans, A. Gallo, W. Keller, and M.A. O'Connell, The properties of a tRNA-specific adenosine deaminase from *Drosophila melanogaster* support an evolutionary link between pre-mRNA editing and tRNA modification. *Mol Cell Biol* 20(3):825-33 (2000).

Keegan, L.P., et al. The many roles of an RNA editor. *Nat Rev Genet.* 2:869-78 (2001).

Keller, W., J. Wolf, and A. Gerber, Editing of messenger RNA precursors and of tRNAs by adenosine to inosine conversion. *FEBS Lett*, 452(1-2):71-6. (1999).

Khan, M.A., Aberham, C., Kao, S., Akari, H., Gorelick, R., Bour, S. and Strebel, K. Human immunodeficiency virus type 1 Vif protein is packaged into the nucleoprotein complex through an interaction with viral genomic RNA. *J. Virol.* 75(16):7252-7265 (2001).

Kleiman, L., tRNA(Lys3): the primer tRNA for reverse transcription in HIV-1. *IUBMB Life* 53(2):107-14 (2002).

Kohler, M., Burnashev, N., Sakmann, B. and Seeburg, P. H. Determinants of Ca 2+ permeability in both TM1 and TM2 of high affinity kainate receptor channels : diversity by RNA editing. *Neuron* 10:491-500 (1993).

Koup, R. A., C. A. Pikora, K. Luzuriaga, D. B. Brettler, E. S. Day, G. P. Mazzara, and J. L. Sullivan. 1991. Limiting dilution analysis of cytotoxic T lymphocytes to human immunodeficiency virus gag antigens in infected persons: in vitro quantitation of effector cell populations with p17 and p24 specificities. The Journal of Experimental Medicine 174:1593-600.

Koup, R. A., J. T. Safrit, Y. Cao, C. A. Andrews, G. McLeod, W. Borkowsky, C. Farthing, and D. D. Ho. 1994. Temporal association of cellular immune responses with the initial control of viremia in primary human immunodeficiency virus type 1 syndrome. Journal of Virology 68:4650-5.

Krogh, A., Brown, M., Mian, I. S., Sjolander, K. and Haussler, D. Hidden Markov models in computational biology. Applications to protein modeling, *J Mol Biol*. 235:1501-31 (1994).

Kumar, M. and G.G. Carmichael Nuclear antisense RNA induces extensive adenosine modifications and nuclear retention of target transcripts. *Proc Natl Acad Sci U S A*. 94(8):3542-7 (1997).

Kuyper, L.F. and C.W. Carter, Resolving crystal polymorphism by finding 'stationary points' from quantitative analysis of crystal growth response surfaces. *J. Crystal Growth.* 168:135-169 (1996).

Kuzin, Li., J. E. Snyder, G. D. Ugine, D. Wu, S. Lee, T. J. Bushnell, R. A. Insel, F. M. Young, Bottaro, A., Tetracyclines inhibit activated B cell function. *Int. Immunol.* 12:921-931 (2001).

Kuzin, Il, G.D. Ugine, D. Wu, F. Young, J. Chenand A. Bottaro, Normal isotype switching in B cells lacking the I mu exon splice donor site: evidence for multiple I mu-like germline transcripts. *J Immunol.* 164(3):1451-7 (2000).

Lanier, L. L. 1998. NK cell receptors. Annu Rev Immunol 16:359-93.

Lau, P. P., Xiong, W. J., Zhu, H. J., Chen, S. H. and Chan, L. Apolipoprotein B mRNA editing is an intranuclear event that occurs post-transcriptionally coincident with splicing and polyadenylation. *J. Biol. Chem.* 266:20550-20554 (1991).

(56) References Cited

OTHER PUBLICATIONS

Lau, P.P, Chang, B.H.J. and Chan, L. Two-hybrid cloning identifies an RNA-binding protein GRY-RBP, as a component of apobec-1 editosome. *Biochem. Biophys. Res. Commun.* 282(4):977-983 (2001).

Lau, P.P., Cahill, D.J., Zhu, H.J. and Chan, L. Ethanol modulates apolipoprotein B mRNA editing in the rat. *J. Lipid Res.* 36:2069-2078 (1995).

Lau, P.P., Villanueva, H., Kobayashi, K., Nakamuta, M., Chang, H.J., Chan, L., A DnaJ protein, Apobec-1-binding protein-2, modulates apolipoprotein B mRNA editing. J. Biol. Chem. 276:46445-46452 (2001).

Lau, P.P., Zhu, H.J., Baldini, A., Charnsangavej, C. and Chan, L. Dimeric structure of a human apolipoprotein B mRNA editing protein and cloning and chromosomal localization of its gene. *Proc. Natl. Acad. Sci. USA* 91:8522-8526 (1994).

Lau, P.P., Zhu, H.J., Nakamuta, M. and Chan, L. Cloning of an Apobec-1-binding protein that also interacts with apolipoprotein B mRNA and evidence for its involvement in RNA editing. *J. Biol. Chem.* 272(3):1452-1455 (1997).

Le Hir, H., Izaurralde, E., Maquat, L. E. and Moore, M. J. (2000) The spliceosome deposits multiple proteins 20-24 nucleotides upstream of mRNA exon-exon junctions. EMBO J. 19, 6860-6869.

Lecossier, D., Bouchonnet, F., Clavel, F. and Hance, A.J. (2003) Science 300: 1112.

Lee, R.M., et al., (1998) An alternatively spliced form of apobec-1 messenger RNA is overexpressed in human colon cancer. Gastroenterology. 115:1096-103.

Lei et al., Inhibition of hepatitis B virus replication by APOBEC3G in vitro and in vivo, *World Journal of Gastroenterology*, 12(28): pp. 4492-4497, Jul. 2006.

Lellek, H., Kirsten, R., Diehl, I., Apostel, F., Buck, F. and Greeve, J.(2000) Purification and Molecular cloning of a novel essential component of the apolipoprotein B mRNA editing Enzyme-complex. J. Biol. Chem., 275, 19848-19856.

Lesk, A.M. and C. Chothia, How different amino acid sequences determine similar protein structures: the structure and evolutionary dynamics of the globins. *J Mol Biol* 136(3):225-70 (1980).

Lewis, J. D. and Tollervey, D. (2000) Like attracts like: getting RNA processing together in the nucleus. Science 288, 1385-1389.

Liao, W., Hong, S.H., Chan, B.H.J., Rudolph, F.B., Clark, S.C. and Chan, L. (1999) APOBEC-2, a cardiac- and skeletal muscle-specific member of the cytidine deaminase supergene family. Biochem. Biophys. Res. Commun. 260, 398-404.

Liddament, M. T., W. L. Brown, A. J. Schumacher, and R. S. Harris. 2004. APOBEC3F properties and hypermutation preferences indicate activity against HIV-1 in vivo. Curr Biol 14:1385-91.

Liu, B., X. Yu, K. Luo, Y. Yu, and X. F. Yu. 2004. Influence of primate lentiviral Vif and proteasome inhibitors on human immunodeficiency virus type 1 virion packaging of APOBEC3G. J Virol 78:2072-81.

Liu, H., X. Wu, M. Newman, G.M. Shaw, B.H. Hahn, and J.C. Kappes, The Vif protein of human and simian immunodeficiency viruses is packaged into virions and associates with viral core structures. *J Virol.* 69(12):7630-8 (1995).

Liu, H.X., M. Zhangand A.R. Krainer, Identification of functional exonic splicing enhancer motifs recognized by individual SR proteins. *Genes Dev*, 12(13):1998-2012 (1998).

Liu, Y. and C.E. Samuel, Mechanism of interferon action: functionally distinct RNA-binding and catalytic domains in the interferon-inducible, double-stranded RNA-specific adenosine deaminase. *J Virol.* 70(3):1961-8 (1996).

Liu, Y., R.B. Emeson, and C.E. Samuel, Serotonin-2C receptor pre-mRNA editing in rat brain and in vitro by splice site variants of the interferon-inducible double-stranded RNA-specific adenosine deaminase ADAR1. *J Biol Chem.* 274(26):8351-8 (1999).

Long, E. O. 1999. Regulation of immune responses through inhibitory receptors. Annu Rev Immunol 17:875-904.

Longacre, A. and U. Storb, A novel cytidine deaminase affects antibody diversity. Cell 102(5): 541-4 (2000).

Lum, J. J., O. J. Cohen, Z. Nie, J. G. Weaver, T. S. Gomez, X. J. Yao, D. Lynch, A. A. Pilon, N. Hawley, J. E. Kim, Z. Chen, M. Montpetit, J. Sanchez-Dardon, E. A. Cohen, and A. D. Badley. 2003. Vpr R77Q is associated with long-term nonprogressive HIV infection and impaired induction of apoptosis. J Clin Invest 111:1547-54.

Maas, S. and Rich, A. (2000) Changing genetic information through RNA editing. BioEssays 22, 790-802.

Maas, S., Melcher, T. and Seeburg, P. H. (1997) Mammalian RNA-dependent deaminases and edited mRNAs. Curr. Opin. Cell. Biol. 9, 343-349.

Maas, S., Melcher, T., Herb, A., Seeburg, P.H., Keller, W., Krause, S., Higuchi, M. and O'Connell, M.A. (1996). Structural requirements for RNA editing in glutamate receptor pre-mRNA by recombinant double-stranded RNA adenosine deaminase. J. Biol. Chem. 271, 12221-12226.

MacGinnitie, A.J., Anant, S. and Davidson, N.O. (1995) Mutagenesis of APOBEC-1, the catalytic subunit of the mammalian apolipoprotein B mRNA editing enzyme, reveals distinct domains that mediate cytosine nucleoside deaminase, RNA-binding, and RNA editing activity. J. Biol. Chem. 270, 14768-14775.

Madani, N. and D. Kabat, *An endogenous inhibitor of human immunodeficiency virus in human lymphocytes is overcome by the viral Vif protein.* J Virol. 72(12):10251-5 (1998).

Madsen P., Anant S., Rasmussen, H.H., Gromov, P., Vorum, H., Dumanski, J.P., Tommerup, N., Collins, J.E., Wright, C.L., Dunham, I., MacGinnitie, A.J., Davidson, N.O. and Celis, J.E. Psoriasis upregulated phorbolin-1 shares structural but not functional similarity to the mRNA-editing protein apobec-1. *J. Invest. Dermatol.* 113(2):162-169 (1999).

Mangeat, B., P. Turelli, S. Liao, and D. Trono. 2004. A single amino acid determinant governs the species-specific sensitivity of APOBEC3G to Vif action. J Biol Chem 279:14481-3.

Mangeat, B., Turelli, P., Caron, G., Friedli, M., Perrin, L., and Trono, D. 2003. Broad antiretroviral defence by human APOBEC3G through lethal editing of nascent reverse transcripts. *Nature* 424:99-103.

Manis, J.P., Y. Gu, R. Lansford, E. Sonoda, R. Ferrini, L. Davidson, K. Rajewskyand F.W. Alt, Ku70 is required for late B cell development and immunoglobulin heavy chain class switching. *J Exp Med.* 187(12):2081-9 (1998).

Mansky, L.M., S. Preveral, L. Selig, R. Benarous, and S. Benichou, The interaction of vpr with uracil DNA glycosylase modulates the human immunodeficiency virus type 1 In vivo mutation rate. 74(15):7039-47 (2000).

Maquat, L. and Carmichael, G. G. Quality control of mRNA function. *Cell* 104(2):173-176 (2001).

Mariani, R., Chen, D., Schrofelbauer, B., Navarro, F., Konig, R., Bollman, B., Munk, C., Nymark-McMahon, H., and Landau, N.R. 2003. Species-specific exclusion of APOBEC3G from HIV-1 virions by Vif. *Cell* 114:21-31.

Martin, A. and M.D. Scharff, *AID and mismatch repair in antibody diversification.* Nat Rev Immunol. 2(8):605-14 (2002).

Martin, A., P.D. Bardwell, C.J. Woo, M. Fan, M.J. Shulmanand M.D. Scharff, Activation-induced cytidine deaminase turns on somatic hypermutation in hybridomas. *Nature.* 415(6873): 802-6 , (2002).

Mascola, J. R., G. Stiegler, T. C. VanCott, H. Katinger, C. B. Carpenter, C. E. Hanson, H. Beary, D. Hayes, S. S. Frankel, D. L. Birx, and M. G. Lewis. 2000. Protection of macaques against vaginal transmission of a pathogenic HIV-1/SIV chimeric virus by passive infusion of neutralizing antibodies. Nat Med 6:207-10.

McCahill, A., Lankester, D.J., Park, S., Price, N.T. and Zammit, V.A. (2000) Acute modulation of the extent of apoB mRNA editing and relative rates of synthesis of apoB48 and apoB100 in cultured rat hepatocytes by osmotic and other stresses. Molec. Cell. Biochem. 208, 77-87.

Mehta, A., Driscoll, D.M. Identification of Domains in APOBEC-1 Complementation Factor Required for RNA Binding and Apolipoprotein B mRNA editing. *RNA.* 8:69-82 (2002).

Mehta, A., Kinter, M.T., Sherman, N.E. and Driscoll, D.M. Molecular cloning of apobec-1 complementation factor, a novel RNA- binding protein involved in the editing of apolipoprotein B mRNA, *Mol Cell Biol.* 20:1846-54 (2000).

(56) References Cited

OTHER PUBLICATIONS

Mian, I.S., Moser, M.J., Holley, W.R. and Chatterjee, A. Statistical modeling and phylogenetic analysis of a deaminase domain, J Comput. Biol. 5: 57-72 (1998).

Migueles, S. A., A. C. Laborico, H. Imamichi, W. L. Shupert, C. Royce, M. McLaughlin, L. Ehler, J. Metcalf, S. Liu, C. W. Hallahan, and M. Connors. 2003. The differential ability of HLA B*5701+ long-term nonprogressors and progressors to restrict human immunodeficiency virus replication is not caused by loss of recognition of autologous viral gag sequences. Journal of Virology 77:6889-98.

Minegishi, Y., A. Lavoie, et al. (2000). "Mutations in activation-induced cytidine deaminase in patients with hyper IgM syndrome." Clin Immunol 97(3): 203-10.

Morrison, J.R., Paszty, C., Stevens, M.E., Hughes, S.D., Forte, T. and Scott, J. (1996) ApoB RNA editing enzyme-deficient mice are viable despite alterations in lipoprotein metabolism. Proc. Natl. Acad. Sci. USA 93, 7154-7159.

Mukhopadhyay, D., S. Anant, R.M. Lee, S. Kennedy, D. Viskochil and N.O. Davidson, C→U editing of neurofibromatosis 1 mRNA occurs in tumors that express both the type II transcript and apobec-1, the catalytic subunit of the apolipoprotein B mRNA-editing enzyme. *Am J Hum Genet.* 70(1):38-50 (2002).

Muramatsu, M., K. Kinoshita, et al. (2000). "Class switch recombination and hypermutation require activation-induced cytidine deaminase (AID), a potential RNA editing enzyme." Cell 102(5): 553-63.

Muramatsu, M., V. S. Sankaranand, et al. (1999). "Specific expression of activation-induced cytidine deaminase (AID), a novel member of the RNA-editing deaminase family in germinal center B cells." J Biol Chem 274(26): 18470-6.

Muschen, M., K. Rajewsky, M. Kronke and R. Kuppers, The origin of CD95-gene mutations in B-cell lymphoma. Trends Immunol, 2002. 23(2): p. 75-80.

Muto, T., M. Muramatsu, et al. (2000). "Isolation, tissue distribution, and chromosomal localization of the human activation-induced cytidine deaminase (AID) gene." Genomics 68(1): 85-8.

Nagaoka, H., M. Muramatsu, N. Yamamura, K. Kinoshita and T. Honjo, Activation-induced deaminase (AID)-directed hypermutation in the immunoglobulin Smu region: implication of AID involvement in a common step of class switch recombination and somatic hypermutation. J Exp Med, 2002. 195(4): p. 529-34.

Nakamuta, M., Chang, B.H.J., Zsigmond, E., Kobayashi, K., Lei, H., Ishida, B.Y., Oka, K., Li, E. and Chan, L. (1996) Complete phenotypic characterization of apobec-1 knockout mice with a wild-type genetic background and a human apoB transgenic background, and restoration of apoB mRNA editing by somatic gene transfer of APOBEC-1. J. Biol. Chem. 271, 25981-25988.

Navaratnam, N., Bhattacharya, S., Fujino, T., Patel, D., Jarmuz, A.L. and Scott, J.. Evolutionary origins of apoB mRNA editing: catalysis by a cytidine deaminase that has acquired a novel RNA-binding motif at its active site. Cell 81, 187-195 (1995).

Navaratnam, N., D., Patel, R.R., Shah, J.C., Greeve L.M., Powell, T.J., Knott, J., Scott, An additional editing site is present in apolipoprotein B mRNA. Nucleic Acids Res., 19:1741-1744 (1991).

Navaratnam, N., Fujino, T., Bayliss, J., Jarmuz, A., How, A. Richardson, N., Somasekaram, A. Bhattacharya, S., Carter, C. & Scott, J. *Escherichia coli* cytidine deaminase provides a molecular model for ApoB RNA editing and a mechanism for RNA substrate recognition *JMB* 275:695-714 (1998).

Navaratnam, N., R. Shah, D. Patel, V. Fayand J. Scott, Apolipoprotein B mRNA editing is associated with UV crosslinking of proteins to the editing site. Proc Natl Acad Sci U S A. 90(1):222-6 (1993).

Neuberger, M.S., Harris, R.S., Di Noia, J., and Petersen-Mahrt, S.K. Immunity through DNA deamination. Trends in Biochemical Sciences. Advanced online publication, in press (2003).

Neumann, J. R., Morency, C. A. and Russian, K. O. A novel rapid assay for chloramphenicol acetyltransferase gene expression. *BioTechniques* 5: 444-448 (1987).

Nixon, D. F., A. R. Townsend, J. G. Elvin, C. R. Rizza, J. Gallwey, and A. J. McMichael. 1988. HIV-1 gag-specific cytotoxic T lymphocytes defined with recombinant vaccinia virus and synthetic peptides. Nature 336:484-7.

O'Brien, S. J., and J. P. Moore. 2000. The effect of genetic variation in chemokines and their receptors on HIV transmission and progression to AIDS. Immunol Rev 177:99-111.

O'Brien, S. J., X. Gao, and M. Carrington. 2001. HLA and AIDS: a cautionary tale. Trends Mol Med 7:379-81.

O'Connell, M.A. RNA Editing: Rewriting Receptors. *Current Biology* 7:R437-R439 (1997).

Ohagen, A. and D. Gabuzda, Role of Vif in stability of the human immunodeficiency virus type 1 core. *J Virol,.* 74(23):11055-66 (2000).

Oka, K., Kobayashi, K., Sullivan, M., Martinez, J., Teng, B.B., Ishimura-Oka, K. and Chan, L.. Tissue-specific inhibition of apoB B mRNA editing in the liver by adenovirus-mediated transfer of a dominant negative mutant APOBEC-1 leads to increased low density lipoprotein in mice. *J. Biol. Chem.* 272(3):1456-1460 (1997).

Okazaki, I.M., et al. The AID enzyme induces class switch recombination in fibroblasts. Nature. 416:340-5 (2002).

Paddison, P.J., A.A. Caudy, E. Bernstein, G.J. Hannon and D.S. Conklin, Short hairpin RNAs (shRNAs) induce sequence-specific silencing in mammalian cells. Genes Dev, 2002. 16(8):948-58.

Paddison, P.J., A.A. Caudy and G.J. Hannon, Stable suppression of gene expression by RNAi in mammalian cells. Proc Natl Acad Sci U S A, 2002. 99(3): p. 1443-8.

Pantaleo, G., and R. A. Koup. 2004. Correlates of immune protection in HIV-1 infection: what we know, what we don't know, what we should know. Nat Med 10:806-10.

Pantaleo, G., S. Menzo, M. Vaccarezza, C. Graziosi, O. J. Cohen, J. F. Demarest, D. Montefiori, J. M. Orenstein, C. Fox, and L. K. Schrager. 1995. Studies in subjects with long-term nonprogressive human immunodeficiency virus infection. The New England Journal of Medicine 332:209-16.

Papavasiliou, F.N. and D.G. Schatz Cell-cycle-regulated DNA double-stranded breaks in somatic hypermutation of immunoglobulin genes. *Nature* 408(6809):216-21 (2000).

Papavasiliou, F.N. and D.G. Schatz The Activation-induced Deaminase Functions in a Postcleavage Step of the Somatic Hypermutation Process. *J Exp Med* 195(9):1193-1198 (2002).

Petersen-Mahrt, S.K., et al., AID mutates *E. coli* suggesting a DNA deamination mechanism for antibody diversification. *Nature* 418:99-104 (2002).

Pham, P., Bransteitter, R., Petruska, J. and Goodman, M.F. Processive AID-catalyzed cytosine deamination on single-stranded DNA simulates somatic hypermutation. *Nature,* Jul. 2003, 424(6944):103-7.

Phillips, R. E., S. Rowland_Jones, D. F. Nixon, F. M. Gotch, J. P. Edwards, A. O. Ogunlesi, J.G. Elvin, J. A. Rothbard, C. R. Bangham, and C. R. Rizza. 1991. Human immunodeficiency virus genetic variation that can escape sytotoxic T cell recognition. Nature 354:453-9.

Phung, T.L., Sowden, M.P., Sparks, J.D., Sparks, C.E. and Smith, H.C. (1996) Regulation of hepatic apoB RNA editing in the genetically obese Zucker rat. Metabolism 45, 1056-1058.

Polson, A.G., B.L. Bass, and J.L. Casey, RNA editing of hepatitis delta virus antigenome by dsRNA-adenosine deaminase. *Nature* 380(6573):454-6 (1996).

Potterton, E., S. McNicholas, E. Krissinel, K. Cowtan, and M. Noble, The CCP4 molecular-graphics project. *Acta Crystallogr D Biol Crystallogr.* 58(Pt 11):1955-7 (2002).

Powell, L.M., Wallis, S.C., Pease, R.J., Edwards, Y.H., Knott, T.J. and Scott, J. (1987) A novel form of tissue-specific RNA processing produces apolipoprotein-B48 in intestine. Cell 50, 831-840.

Puck, J.M., A disease gene for autosomal hyper-IgM syndrome: more genes associated with more immunodeficiencies. Clin Immunol,( 2000). 97(3): p. 191-2.

Rada, C., et al., (2002) AID-GFP chimeric protein increases hypermutation of Ig genes with no evidence of nuclear localization. Proc. Natl. Acad. Sci USA. 99:7003-7008.

Ramiro, A.R., P. Stavropoulos, M. Jankovic, and M.C. Nussenzweig, Transcription enhances AID-mediated cytidine deamination by exposing single-stranded DNA on the nontemplate strand. *Nat Immunol* (2003).

(56) References Cited

OTHER PUBLICATIONS

Renda, M.J., J.D. Rosenblatt, E. Klimatcheva, L.M. Demeter, R.A. Bambara, and V. Planelles, Mutation of the methylated tRNA(Lys)(3) residue A58 disrupts reverse transcription and inhibits replication of human immunodeficiency virus type 1. *J Virol* 75(20):9671-8 (2001).
Revy, P, Muto, R., Levy, Y., Geissmann, f., Plebani, A., Sanal, O., Catalan, N., Forveille, M., Dufourcq-Lagelouse, R., Gennery, A., Tezcan, I., Ersoy, F., Kayserili, H., Ugazio, A.G., Brousse, N., Muramatsu, M., Notarangelo, L.D., Kinoshita, K., Honjo, T., Fisher, A. and Durandy, A. Activation-induced cytidine deaminase (AID) deficiency causes the autosomal recessive form of the hyper-IgM syndrome (HIGM2). Cell 102,(5):565-576 (2000).
Richardson, N., Navaratnam, N. and Scott, J. (1998) Secondary structure for the apolipoprotein B mRNA editing site. AU binding proteins interact with a stem loop. J. Biol Chem. 273, 31707-31717.
Rinaldo, C., X. L. Huang, Z. F. Fan, M. Ding, L. Beltz, A. Logar, D. Panicali, G. Mazzara, J. Liebmann, and M. Cottrill. 1995. High levels of anti-human immunodeficiency virus type 1 (HIV-1) memory cytotoxic T-lymphocyte activity and low viral load are associated with lack of disease in HIV-1-infected long-term nonprogressors. Journal of Virology 69:5838-42.
Robberson, B. L., Cote, G. J. and Berget, S. M. (1990) Exon definition may facilitate splice site selection in RNAs with multiple exons. Mol. Cell. Biol. 10, 1084-1094.
Rolink, A., F. Melchersand J. Andersson, The SCID but not the RAG-2 gene product is required for S mu-S epsilon heavy chain class switching. Immunity, 1996. 5(4): p. 319-30.
Rosenberg, E. S., J. M. Billingsley, A. M. Caliendo, S. L. Boswell, P. E. Sax, S. A. Kalams, and B. D. Walker. 1997. Vigorous HIV-1-specific CD4+ T cell responses associated with control of viremia. Science 278:1447-50.
Rowland_Jones, S., J. Sutton, K. Ariyoshi, T. Dong, F. Gotch, S. McAdam, D. Whitby, S. Sabally, A. Gallimore, and T. Corrah. 1995. HIV-specific cytotoxic T-cells in HIV-exposed but uninfected Gambian women. Nature Medicine 1:59-64.
Rueter, S. M. and Emeson, R. B. (1998) Adenosine-to-inosine conversion in mRNA. In Modification and Editing of RNA (Grosjean, H. and Benne, R., eds.), pp. 343-361, American Society for Microbiology Press, Washington.
Rueter, S.M., Dawson, T.R. and Emeson, R.B. (1999) Regulation of alternative splicing by RNA editing. Nature 399, 75-80.
Sakashita, E. and H. Sakamoto, Protein-RNA and protein-protein interactions of the *Drosophila* sex-lethal mediated by its RNA-binding domains. Journal of Biochemistry, 1996. 120(5): p. 1028-33.
Sale, J.E., D.M. Calandrini, M. Takata, S. Takedaand M.S. Neuberger, Ablation of XRCC2/3 transforms immunoglobulin V gene conversion into somatic hypermutation. Nature, 2001. 412(6850): p. 921-6.
Sali, A., L. Potterton, F. Yuan, H. van Vlijmen, and M. Karplus, Evaluation of comparative protein modeling by Modeller. *Proteins*. 23(3): p. 318-26 (1995).
Schock, D., Kuo, S.R., Steinburg, M.F., Bolognino, M., Sparks, J.D., Sparks, C.E. and Smith, H.C. (1996). An auxiliary factor containing a 240 kDa protein is involved in apoB RNA editing. Proc. Natl. Acad. Sci. USA 93, 1097-1102.
Schrofelbauer, B., Chen, D., and Landau, N.R. 2004. A single amino acid of APOBEC3G controls its species-specific interaction with virion infectivity factor (Vif). *Proc Natl Acad Sci U S A* 101:3927-3932.
Scott, J. (1989) The molecular and cell biology of apolipoprotein-B.. J. Mol. Med. 6, 65-80.
Seeburg, P. H., Higuchi, M. and Sprengel, R. (1998) RNA editing of brain glutamate receptor channels : mechanism and physiology. Brain Res. Rev. 26, 217-229.
Selig, L., S. Benichou, M.E. Rogel, L.I. Wu, M.A. Vodicka, J. Sire, R. Benarous, and M. Emerman, Uracil DNA glycosylase specifically interacts with Vpr of both human immunodeficiency virus type 1 and simian immunodeficiency virus of sooty mangabeys, but binding does not correlate with cell cycle arrest. *J Virol*. 71(6):4842-6. (1997).
Shah, R. R., Knott, T. J., Legros, J. E., Navaratnam, N., Greeve, J. C. and Scott, J. Sequence requirements for the editing of apolipoprotein B mRNA. *J. Biol. Chem*. 266, 16301-16304 (1991).
Sheehy, A.M., Gaddis, N.C., Choi, J.D., Malim, M.H. 2002. Isolation of a human gene that inhibits HIV-1 infection and is suppressed by the viral Vif protein. *Nature* 418:646-650.
Shibata, R., T. Igarashi, N. Haigwood, A. Buckler-White, R. Ogert, W. Ross, R. Willey, M. W. Cho, and M. A. Martin. 1999. Neutralizing antibody directed against the HIV-1 envelope glycoprotein can completely block HIV-1/SIV chimeric virus infections of macaque monkeys. Nat Med 5:204-10.
Shindo, K., A. Takaori-Kondo, M. Kobayashi, A. Abudu, K. Fukunaga, and T. Uchiyama. 2003. The enzymatic activity of CEM15/Apobec-3G Is essential for the regulation of the infectivity of HIV-1 Virion, but not a sole determinant of Its antiviral activity. J Biol Chem.278:44412-6.
Siddiqui, J. F. M., Van Mater, D., Sowden, M. P. and Smith, H. C. (1999) Disproportionate relationship between APOBEC-1 expression and apolipoprotein B mRNA editing activity. Exp. Cell Res. 252(1):154-164.
Simon, J.H. and M.H. Malim. The human immunodeficiency virus type 1 Vif protein modulates the postpentration stability of viral nucleoprotein complexes. *J Virol*. 70(8):5297-305 (1996).
Simon, J.H., N.C. Gaddis, R.A. Fouchier, and M.H. Malim, *Evidence for a newly discovered cellular anti-HIV-1 phenotype. Nat Med*. 4(12):1397-400 (1998).
Simpson, L. and Emeson, R. B. (1996) RNA editing. Annu. Rev. Neurosci. 19, 27-52.
Skuse, G.R., A.J. Cappione, M. Sowden, L.J. Methenyand H.C. Smith, The neurofibromatosis type I messenger RNA undergoes base-modification RNA editing. Nucleic Acids Res, 1996. 24(3): p. 478-85.
Smith, H. C., Kuo, S. R., Backus, J. W., Harris, S. G., Sparks, C. E. and Sparks, J. D. (1991) In vitro mRNA editing : identification of a 27 S editing complex. Proc. Natl. Acad. Sci. U.S.A. 88, 1489-1493.
Smith, H.C. (1993) Apo B mRNA editing: the sequence to the event. Seminars in Cell Biology (Stuart, K., ed.) Saunders Sci. Publications/ Academic Press, London, 4, 267-278.
Smith, H.C. and Sowden, M.P. (1996) Base modification RNA editing through deamination—the good, the bad and the unregulated. Trends in Genetics 12, 418-424.
Smith, H.C., Analysis of protein complexes assembled on apolipoprotein B mRNA for mooring sequence-dependent RNA editing. Methods, 1998. 15(1): p. 27-39.
Smith, H.C., Gott, J.M. and Hanson, M.R. (1997) A guide to RNA editing. RNA, 3, 1105-1123.
Sohail, A., Klapacz, J., Samaranayake, M., Ullah, A. and Bhagwat, A. Human activation-induced cytidine deaminase causes transcript-dependent, strand-biased C to U deaminations. *Nucleic Acids. Res*. 31(12):2990-2994 (2003).
Soya, P. and D.J. Volsky, Efficiency of viral DNA synthesis during infection of permissive and nonpermissive cells with vif-negative human immunodeficiency virus type 1. *J Virol*. 67(10): 6322-6 (1993).
Sowden, M. P., Hamm, J. K. and Smith, H. C. (1996) Over-expression of APOBEC-I results in mooring sequence dependent promiscuous RNA editing. J. Biol. Chem. 271(6):3011-3017.
Sowden, M. P., Harrison, S. M., Ashfield, R. A., Kingsman, A. J. and Kingsman, S. M. (1989) Multiple cooperative interactions constrain BPV-1 E2 dependent activation of transcription. Nucleic Acids Res. 17, 2959-2972.
Sowden, M.P. and H.C. Smith, Commitment of apolipoprotein B RNA to the splicing pathway regulates cytidine-to-uridine editing-site utilization. Biochem J, 2001. 359(Pt 3): p. 697-705.
Sowden, M.P., Ballatori, N., de Mesy Jensen, K.L., Hamilton Reed, L., Smith, H.C., The editosome for cytidine to uridine mRNA editing has a native complexity of 27S: identification of intracellular domains containing active and inactive editing factors. J. Cell Science, 2002. 115: p. 1027-1039.
Sowden, M.P., Eagleton, M.J. and Smith, H.C. (1998). ApoB RNA sequence 3' of the mooring sequence and cellular sources of auxiliary factors determine the location and extent of promiscuous editing. Nucleic Acids Res. 26, 1644-1652.

(56) References Cited

OTHER PUBLICATIONS

Sowden, M.P., Hamm, J.K., Spinelli, S. and Smith, H.C. (1996) Determinants involved in regulating the proportion of edited apolipoprotein B RNAs. RNA 2(3):274-288.

Spector, D. (1993) Macromolecular domains within the cell nucleus. Annu. Rev. Cell Biol. 9, 265-315.

Steinburg, M. F., Schock, D., Backus, J. W. and Smith, H. C. (1999) Tissue-specific differences in the role of RNA 3' of the apolipoprotein B mRNA mooring sequence in editosome assembly. Biochem. Biophys. Res. Commun. 263(1):81-86.

Stopak, K., De Noronha, C., Yonemoto, W., and Greene, W.C. 2003. HIV-1 Vif Blocks the Antiviral Activity of APOBEC3G by Impairing both Its Translation and Intracellular Stability. Mol Cell 12:591-601.

Strebel, K., D. Daugherty, K. Clouse, D. Cohen, T. Folks, and M.A. Martin, The HIV 'A' (sor) gene product is essential for virus infectivity. Nature. 328(6132): p. 728-30 (1987).

Svarovskaia, E. S., H. Xu, J. L. Mbisa, R. Barr, R. J. Gorelick, A. Ono, E. O. Freed, W. S. Hu, and V. K. Pathak. 2004. Human APOBEC3G mRNA—editing enzyme—catalytic polypeptide—like 3G (APOBEC3G) is incorporated into HIV-1 virions through interactions with viral and nonviral RNAs. J Biol Chem.279:35822-8.

Taagepera, S., McDonald, D., Loeb, J. E., Whitaker, L. L., McElroy, A. K., Wang, J. Y. J. and Hope, T. J. (1998) Nuclear-cytoplasmic shuttling of C-ABL tyrosine kinase. Proc. Natl. Acad. Sci. U.S.A. 95, 7457-7462.

Teng, B. and N.O. Davidson, Evolution of intestinal apolipoprotein B mRNA editing. Chicken apolipoprotein B mRNA is not edited, but chicken enterocytes contain in vitro editing enhancement factor(s). J Biol Chem, 267(29): 21265-72 1992.

Teng, B., Burant, C. F. and Davidson, N.O. Molecular cloning of an apolipoprotein B messenger RNA editing protein, Science, 260:1816-1819 (1993).

Teng, B.B., S. Ochsner, Q. Zhang, K.V. Soman, P.P. Lau, and L. Chan, Mutational analysis of apolipoprotein B mRNA editing enzyme (APOBEC1). structure-function relationships of RNA editing and dimerization. J Lipid Res, 40(4):623-35 (1999).

Turelli et al., Inhibition of Hepatitis B Virus Replication by APOBEC3G, Science, vol. 303: p. 1829, 2004.

Van Mater, D., Sowden, M.P., Cianci, J., Sparks, J.D., Sparks, C.E., Ballitori, N. and Smith, H.C. (1998). Ethanol increases apoB mRNA editing in rat primary hepatocyte and McArdle cells. Biochem. Biophys Res. Commun. 252, 334-339.

Van Parijs, L., Y. Refaeli, J.D. Lord, B.H. Nelson, A.K. Abbasand D. Baltimore, Uncoupling IL-2 signals that regulate T cell proliferation, survival, and Fas-mediated activation-induced cell death. Immunity, 1999. 11(3): p. 281-8.

von Schwedler, U., J. Song, C. Aiken, and D. Trono, Vif is crucial for human immunodeficiency virus type 1 proviral DNA synthesis in infected cells. J Virol. 67(8): 4945-55 (1993).

von Wronski, M.A., Hirano, K.I., Cagen, L.M., Wilcox, H.G., Raghow, R., Thorngate, F.E., Heimberg, M., Davidson, N.O. and Elam, M.B. (1998). Insulin increases expression of apobec-1, the catalytic subunit of the apoB B mRNA editing complex in rat hepatocytes. Metabolism Clinical & Exp. 7, 869-873.

Walker, B. D., S. Chakrabarti, B. Moss, T. J. Paradis, T. Flynn, A. G. Durno, R. S. Blumberg, J. C. Kaplan, M. S. Hirsch, and R. T. Schooley. 1987. HIV-specific cytotoxic T lymphocytes in seropositive individuals. Nature 328:345-8.

Walker, C. M., D. J. Moody, D. P. Stites, and J. A. Levy. 1986. CD8+ lymphocytes can control HIV infection in vitro by suppressing virus replication. Science 234:1563-6.

Wedekind, J.E., G.S. Dance, M.P. Sowden, and H.C. Smith, Messenger RNA editing in mammals: new members of the APOBEC family seeking roles in the family business. Trends Genet 19(4):207-16 (2003).

Wedekind, J.E., X. Kefang, G.S. Dance, M.P. Sowden, and H.C. Smith, The structure of yeast Cdd1 provides insight into the molecular details of the mRNA editase APOBEC-1. (2003—In preparation).

Wiegand, H. L., B. P. Doehle, H. P. Bogerd, and B. R. Cullen. 2004. A second human antiretroviral factor, APOBEC3F, is suppressed by the HIV-1 and HIV-2 Vif proteins. Embo J 23:2451-8.

Winn, M.D. An overview of the CCP4 project in protein crystallography: an example of a collaborative project. J Synchrotron Radiat. 10(Pt 1):23-5 (2003).

Wu, J.H., Semenkovish, C.F., Chen, S.H., Li, W.H. and Chan, L. (1990). ApoB mRNA editing: validation of a sensitive assay and developmental biology of RNA editing in the rat. J. Biol. Chem. 265, 12312-12316.

Xie, K., M. P. Sowden, G. S. Dance, A. T. Torelli, H. C. Smith, and J. E. Wedekind. 2004. The structure of a yeast RNA-editing deaminase provides insight into the fold and function of activation-induced deaminase and APOBEC-1. Proc Natl Acad Sci U S A 101:8114-9.

Xu, H., E. S. Svarovskaia, R. Barr, Y. Zhang, M. A. Khan, K. Strebel, and V. K. Pathak. 2004. A single amino acid substitution in human APOBEC3G antiretroviral enzyme confers resistance to HIV-1 virion infectivity factor-induced depletion. Proc Natl Acad Sci U S A 101:5652-7.

Yamanaka, S., Balestra, M., Ferrell, L., Fan, J., Arnold, K.S., Taylor, S., Taylor, J.M. and Innerarity, T.L. (1995). Apolipoprotein B mRNA-editing protein induces hepatocellular carcinoma and dysplasia in transgenic animals. Proc. Natl. Acad. Sci. USA 92, 8483-8487.

Yamanaka, S., K. S. Poksay, D. M. Driscoll, Innerarity, T. L., Hyperediting of multiple cytidines of apolipoprotein B mRNA by APOBEC-1 requires auxiliary protein(s) but not a mooring sequence motif. J. Biol. Chem. 271:11506-11510 (1996).

Yamanaka, S., Poksay, K. S., Balestra, M. E., Zeng, G. Q. and Innerarity, T. L. (1994) Cloning and mutagenesis of the rabbit apoB mRNA editing protein. J. Biol. Chem. 269, 21725-21734.

Yamanaka, S., Poksay, K.S., Arnold, K.S. and Innerarity, T.L. A novel translational repressor mRNA is edited extensively in livers containing tumors caused by the transgene expression of the apoB mRNA-editing enzyme. Genes Dev., 11, 321-33 (1997).

Yang, B., Gao, L., Li, L., Lu, Z., Fan, X., Patel, C.A., Pomerantz, R.J., DuBois, G.C. and Zhang, H. Potent suppression of viral infectivity by the peptides that inhibit multimerizations of human immunodeficiency virus type 1 (HIV-1) vif proteins. J. Biol Chem. 278(8):6596-6602 (2002).

Yang, O. O., S. A. Kalams, A. Trocha, H. Cao, A. Luster, R. P. Johnson, and B. D. Walker. 1997. Suppression of human immunodeficiency virus type 1 replication by CD8+ cells: evidence for HLA class I-restricted triggering of cytolytic and noncytolytic mechanisms. Journal of Virology 71:3120-8.

Yang, Y. and Smith, H. C. (1996) In vitro reconstitution of apolipoprotein B RNA editing activity from recombinant APOBEC-1 and McArdle cell extracts. Biochem. Biophys. Res. Commun. 218, 797-801.

Yang, Y., Ballatori, N., Smith, H.C., Apolipoprotein B mRNA editing and the reduction in Synthesis and secretion of the atherogenic risk factor apoB100 is reduced through TAT-mediated protein transduction of an mRNA editase into hepatocytes. Molec. Pharm. 61:269-276 (2002).

Yang, Y., Kovalski, K. and Smith, H.C. (1997) Partial characterization of the auxiliary factors involved in apoB mRNA editing through APOBC-1 affinity chromatography, J Biol. Chem., 272, 27700-27706.

Yang, Y., M.P., Sowden Y., Yang, H.C., Smith, Intracellular Trafficking Determinants in APOEC-1, the Catalytic Subunit for Cytidine to Uridine Editing of Apolipoprotein B mRNA. Exp. Cell Res. 267:153-164 (2001).

Yang, Y., Sowden, M. P. and Smith, H. C. (2000) Induction of cytidine to uridine editing on cytoplasmic apolipoprotein B mRNA by overexpressing APOBEC-1. J. Biol. Chem. 275(30):22663-22669.

Yang, Y., Yang, Y. and Smith, H. C. (1997) Multiple protein domains determine the cell type-specific nuclear distribution of the catalytic subunit required for apolipoprotein B mRNA editing. Proc. Natl. Acad. Sci. U.S.A. 94, 13075-13080.

Yoshikawa, K., Okazaki, I.M., Eto, T., Kinoshita, K., Muramatsu, M., Nagaoka, H., Honjo, T. (2002). "AID enzyme-induced hypermutation in an actively transcribed gene in fibroblasts." Science 296: 2033-2036.

(56) References Cited

OTHER PUBLICATIONS

Yu, Q. and C.D. Morrow, Essential regions of the tRNA primer required for HIV-1 infectivity. *Nucleic Acids Res.* 28(23):4783-9 (2000).

Yu, Q., D. Chen, R. Konig, R. Mariani, D. Unutmaz, and N. R. Landau. 2004. APOBEC3B and APOBEC3C are potent inhibitors of simian immunodeficiency virus replication. J Biol Chem.279 (51):53379-86.

Yu, Q., Konig, R., Pillai, S., Chiles, K., Kearney, M., Palmer, S., Richman, D., Coffin, J.M., and Landau, N.R. 2004. Single-strand specificity of APOBEC3G accounts for minus-strand deamination of the HIV genome. *Nat Struct Mol Biol* 11:435-442.

Yu, X., Yu, Y., Liu, B., Luo, K., Kong, W., Mao, P., and Yu, X.F. 2003. Induction of APOBEC3G ubiquitination and degradation by an HIV-1 Vif-Cul5-SCF complex. *Science* 302:1056-1060.

Zhang, H., B. Yang, R. J. Pomerantz, C. Zhang, S. C. Arunachalam, and L. Gao. 2003. The cytidine deaminase CEM15 induces hypermutation in newly synthesized HIV-1 DNA. Nature 424:94-98.

Zhang, J., and D. M. Webb. 2004. Rapid evolution of primate antiviral enzyme APOBEC3G. Hum Mol Genet 13:1785-91.

Zheng, Y.H., Irwin, D., Kurosu, T., Tokunaga, K., Sata, T., Peterlin, B.M. (2004) Human APOBEC3F is Another Host Factor that Blocks Human Immunodeficiency Virus Type 1 Replication. *J. Virol.* 78:6073-6076.

Accession No. AF 182420.

Accession No. AW 380203.

Accession No. AK 024854.

Accession No. AF 165520.

Accession No. BQ 056344.

Accession No. BM 564332.

Ulenga et al. "Relationship between human immunodeficiency type 1 infection and expression of human APOBEC3G and APOBEC3F." 2008, J Infect Dis 198(4):486-492.

Chang and Tyring., "Therapy of HIV infection." 2004 Dermatologic Therapy 17(6):449-464.

Chen et al., "Discordant Protein and mRNA Expression in Lung Adenocarcinomas." 2002, Molecular & Cellular Proteomics 1(4):304-313.

\* cited by examiner

Pseudocatalytic Domain (PCD)

```
                          160         170          180         190         200         210         220         230
Sc CDD1           1 MKVGGIEDR QLEALKRAALKACE LSYS PYSH FRVGCSIL TNND VIFTGANVEN ASYSN CIC AERSAMIQVLM AG-HR-SGWK
B.subtilis        1 -------M NRQELITEALKARD MAYA PYSK FQVGAALL TKDG KVYRGCNIEN AAYSM CNC AERTALFKAVS EG-DT--EFQ
E.coli          189 -------- --DALSQAAIAAAN RSHM PYSK SPSGVALE CKDG RIFSGSYAEN AAFNP TLP PLQGALILLNL KG-YDYPDIQ
hAPOBEC-1-nt      1 MTSEKGPST GDPTLRRRIEPWEF DVFY DPRE LRKEACLL YEIK WGMSRKIWRS SGKNT TNH VEVNFIKKFTS ERDF--HPSI
hAPOBEC-1-cf    144 -------- -------------- ---- ---- MRASEYYH CWRN FVNYPPGDEA H--WP QYP PLWMMLYALEL HC-IILSLPP
AID             139 -------- -------------- ---- ---- MTFKDYFY CWNT FVENHERTFK A--WE GLH ENSVRLTRQLR RI-L-L-PL-
APOBEC-3G-nt    152 -------- -------------- ---- ---- MNYDEFQH CWSK FVYSQRELFE P--WN NLP KYYILLHIMLG EI-LRHSIDP
APOBEC-3G-ct    338 -------- -------------- ---- ---- MTYSEFKH CWDT FVDHQGCPFQ P--WD GLD EHSQDLSGRLR AI-LQNQGEN*

α1              β 3₁₀  β      ⇧β1         T   β    T   β            ⇩α2          L 240         250        260        270         280         290         300         310
Sc CDD1          80 CMVICG DSEDQCVS ------- -- PC GVCRQFINEF VVKDFP IVML NSTGS RSKVMT MGEL LPMAF GPSHLN*
B.subtilis       72 MLAVAA DTP-GPVS ------- -- PC GACRQVISEL CTKDVI VVLT NL-QG QIKEMT VEEL LPGAF SSEDLH*
E.coli          259 RAVLAE -------- KADAPLIQW -- DATSATLKAL GC--HS IDRV LL-A*
hAPOBEC-1-nt     81 SCSITW -F--LSWS ------- -- PC WECSQAIRSF LSRHPG VILV -I-Y- VARLFW -HND QQMRQ GLRDLV*
hAPOBEC-1-cf    192 CLKISR -------- R--WQNHLT FF ELHLQNCHYQ T---IP PHIL LAT-L JHPSVA WR*
AID             184 YEVDDL -------- -------- -- RDAFRTLGL*
APOBEC-3G-nt    200 PTFTFN -F----NN*

HUMAN IMMUNODEFICIENCY VIRUS ANTIVIRAL SCREENING ASSAY INVOLVING THE DETECTION OF CEM15 EXPRESSION

CROSS-REFERENCE TO RELATED APPLICATIONS

This application claims benefit of U.S. Provisional Application No. 60/652,177, filed Feb. 11, 2005, which is hereby incorporated herein by reference in its entirety.

ACKNOWLEDGEMENTS

This invention was made with government support under grants R01-AI05163, UO1-AI27658, and R21-AI58789-01 awarded by the National Institutes of Health and grant F49620-01-1-0571 awarded by the Air Force. The government has certain rights in the invention.

BACKGROUND OF THE INVENTION

Human white blood cells express proteins called APOBEC-1 related proteins (ARPs), which are cytidine deaminases that can change the genetic code of an infecting virus. These changes can render the virus incapable of producing an infection when they occur in critical genes encoding viral proteins and/or when they occur extensively throughout the viral genome. APOBEC-1 related proteins (ARPs), such as CEM-15, APOBEC-3B, APOBEC-3C, and APOBEC-3F have been found to have a deleterious effect on HIV-1, HIV-2, retrovirus and hepatitis B. HIV-1, however, expresses a protein called Viral infectivity factor (Vif) that impairs the ability of ARPs such as CEM15 to act on viral DNA.

A small subset of HIV-infected individuals, known as long-term nonprogressors (LNTPs) have substantially slower rates of disease progression in the absence of therapeutic intervention. Clinically, these LTNPs are usually asymptomatic, maintain high CD4 counts and low HIV viremia levels. The characteristics are therefore of prognostic value in evaluating disease severity. The mechanisms responsible for long-term nonprogression have been attributed to defective or less fit HIV variants, strong host immune responses and unique host genetic elements, such as the CCR5 genotype and HLA haplotypes (Buchbinder et al. (1999) Microbes and Infection 1: 1113-1120).

Thus, needed in the art are methods and compositions related to determining the status and mechanisms underlying long-term nonprogression of viral infections. More specifically, the role of APOBEC-1 related proteins in viral progression and its affect in long-term nonprogressors is of importance.

SUMMARY OF THE INVENTION

In accordance with the purposes of this invention, as embodied and broadly described herein, this invention, in one aspect, relates to a method of predicting the severity of a viral infection in a subject. For example, the level of expression of at least one APOBEC-1 related protein is used to indicate the level of severity.

Also disclosed is a method of predicting whether a subject is or will be a long term nonprogressor (LTNP) when infected with a virus. A higher level of expression in a biological sample from the subject of one or more APOBEC-1 related proteins as compared to a control level indicates the subject is a potential LNTP.

Further disclosed is a method of optimizing antiviral therapy in a subject with a viral infection. The level of expression of one or more APOBEC-1 related proteins (ARPs) in a biological sample from the subject is used to adjust the antiviral therapy, thereby optimizing the viral therapy.

Also disclosed is a method of predicting the level of CD4 cells in a subject. The level of CEM15 correlates with the level of CD4 cells and can be used to predict the level of CD4 cells.

Also disclosed is a method of monitoring effectiveness of an antiviral agent in a subject. Specifically, expression levels of one or more APOBEC-1 related proteins are monitored during the treatment. An increase in expression levels of the APOBEC-1 related proteins during the course of treatment indicates the effectiveness of the antiviral agent.

Further disclosed is a method of screening for an antiviral agents and compositions used to detect levels of ARP expression, including nucleic acid primers and probes.

Additional advantages of the invention will be set forth in part in the description which follows, and in part will be obvious from the description, or may be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this specification, illustrate several embodiments of the invention and together with the description, serve to explain the principles of the invention.

FIG. 2 shows schematic depictions of the cytidine deaminase (CDA) polypeptide fold and structure-based alignments of APOBEC-1 with respect to its related proteins (ARPs). FIG. 2d depicts a schematic diagram of the domain structure observed in APOBEC-1 and related ARPs based upon computer-based sequence alignments using the ZDD signature sequence shown in the lower panel of FIG. 2a.

DETAILED DESCRIPTION

Figure 1:
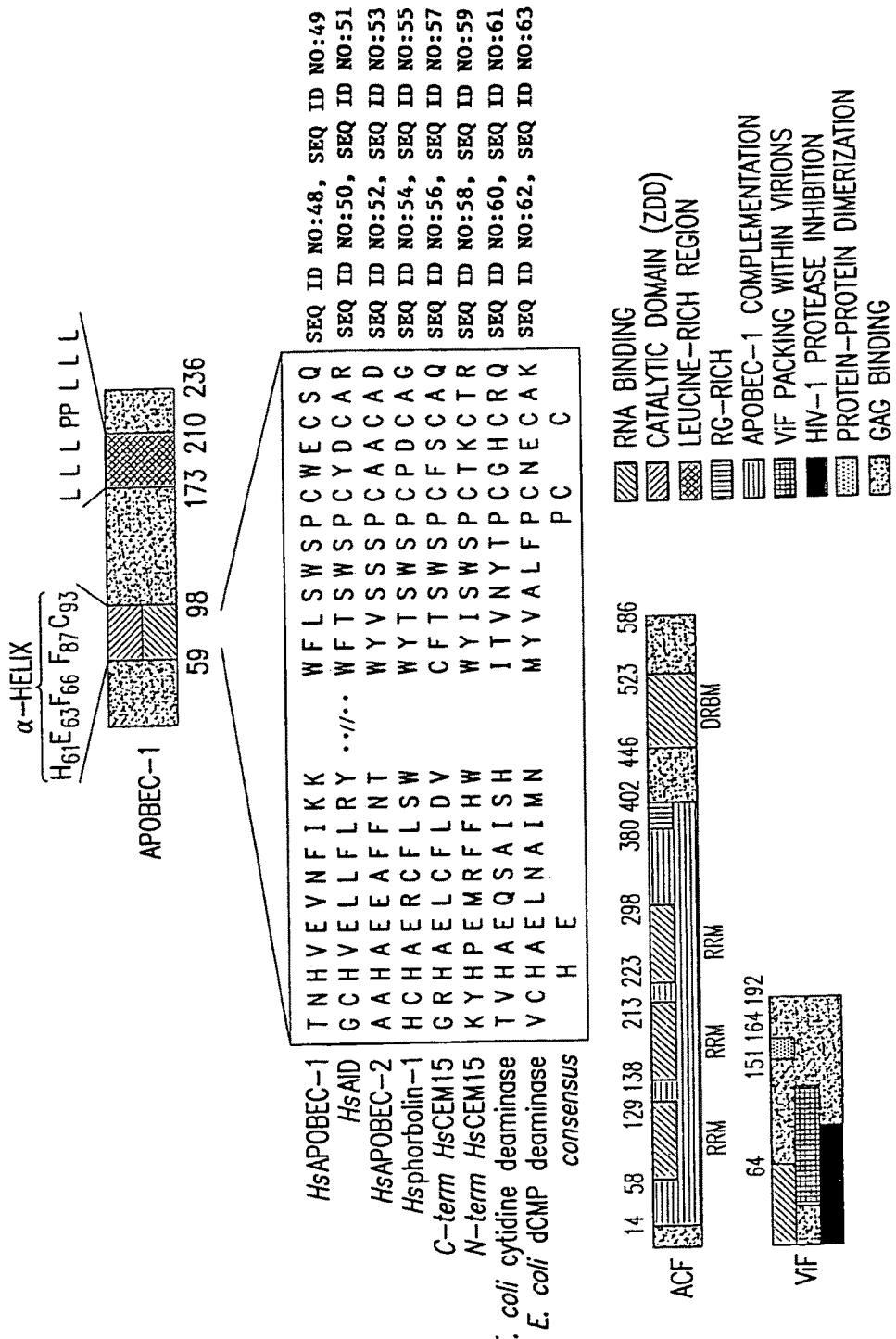
FIG. 1 shows representative members of the APOBEC-1 related family of cytidine deaminases including CEM15. Also shown are APOBEC-1 complementation factor (ACF) and viral infectivity factor (Vif). The catalytic domain of APOBEC-1 is characterized by a ZDD with three zinc ligands (either His or Cys), a glutamic acid, a proline residue and a conserved primary sequence spacing (Mian, I. S., et al., (1998) J Comput Biol. 5:57-72). The ZDD of other deaminases and APOBEC-1 related proteins is shown for comparison along with a consensus ZDD. The indicated residues in the catalytic site of APOBEC-1 bind AU-rich RNA with weak affinity. The leucine rich region (LRR) of APOBEC-1 has been implicated in APOBEC-1 dimerization and shown to be required for editing (Lau, P. P., et al., (1994) Proc Natl Acad Sci USA. 91:8522-6; Oka, K., et al., (1997) J Biol Chem. 272:1456-60) but structural modeling suggests that LRR forms the hydrophobic core of the protein monomer (Navaratnam, N., et al., (1998) J Mol Biol. 275:695-714). ACF complements APOBEC-1 through its APOBEC-1 and RNA binding activities. The RNA recognition motifs (RRM)s are required for mooring sequence-specific RNA binding and these domains plus sequence flanking them are required for APOBEC-1 interaction and complementation (Blanc, V., et al., (2001) J Biol Chem. 276:46386-93; Mehta, A., et al., (2002) RNA. 8:69-82.) APOBEC-1 complementation activity minimally depends on ACF binding to both APOBEC-1 and mooring sequence RNA. A broad APOBEC-1 complementation region is indicated that is inclusive of all regions implicated in this activity (Blanc, V., et al., (2001) J Biol Chem. 276:46386-93; Mehta, A., et al., (2002) RNA. 8:69-82.) Experiments have shown the N-terminal half of Vif is necessary for viral infectivity (Henzler, T. 2001). However, reports have demonstrated that residues in the C-terminus (amino acids 151-164) are essential for infectivity (Yang, S. et al. 2001) and that multimerization of Vif through the motif PPLP (SEQ ID NO: 14) within this region was essential for infectivity. Peptides capable of binding to this domain of Vif blocked Vif-Vif interactions and Vif-Hck interactions in vitro and suppressed viral infectivity in cell-based assay systems. Residues in the N-terminus of Vif are essential for RNA binding and packing of Vif within the virion (Zhang et al. 2000; Khan et al. 2001; Lake et al. 2003).

The APOBEC-1 and APOBEC-1 related compositions described herein are useful in preventing or treating viral infections. Described herein are methods of identifying long term nonprogressors, optimizing antiviral infectivity therapy, predicting the severity of a viral infection in a subject, predicting the level of CD4 cells in a subject, monitoring the effectiveness of an antiviral agent, and screening for an antiviral agent. Also disclosed are nucleic acid sequences used to detect expression of ARPs.

The present invention may be understood more readily by reference to the following detailed description of preferred embodiments of the invention and the Examples included therein and to the Figures and their previous and following description.

Before the present compounds, compositions, articles, devices, and/or methods are disclosed and described, it is to be understood that this invention is not limited to specific synthetic methods, specific recombinant biotechnology methods unless otherwise specified, or to particular reagents unless otherwise specified, as such may, of course, vary. It is also to be understood that the terminology used herein is for the purpose of describing particular embodiments only and is not intended to be limiting.

As used in the specification and the appended claims, the singular forms "a," "an" and "the" include plural referents unless the context clearly dictates otherwise. Thus, for example, reference to "a pharmaceutical carrier" includes mixtures of two or more such carriers, and the like.

Ranges may be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that when a value is disclosed that "less than or equal to" the value, "greater than or equal to the value" and possible ranges between values are also disclosed, as appropriately understood by the skilled artisan. For example, if the value "10" is disclosed the "less than or equal to 10" as well as "greater than or equal to 10" is also disclosed.

In this specification and in the claims which follow, reference will be made to a number of terms which shall be defined to have the following meanings:

"Optional" or "optionally" means that the subsequently described event or circumstance may or may not occur, and that the description includes instances where said event or circumstance occurs and instances where it does not.

The terms "higher," "increases," "elevates," "enhances," or "elevation" refer to increases as compared to a control. The terms "low," "lower," "reduces," "suppresses" or "reduction" refer to decreases as compared to a control level. Control levels can be normal in vivo levels prior to, or in the absence of, an infection or a treatment. Thus, the control can be from the same subject prior to infection or treatment or can be an uninfected or untreated control subject or group thereof.

The term "test compound" is defined as any compound to be tested for its ability to bind to increase ARP activity, production, or expression. "Test compounds" include drugs, molecules, and compounds that come from combinatorial libraries where thousands of such ligands are screened by drug class.

By "subject" is meant an individual. Preferably, the subject is a mammal such as a primate, and, more preferably, a human. The term "subject" can include domesticated animals, such as cats, dogs, etc., livestock (e.g., cattle, horses, pigs, sheep, goats, etc.), and laboratory animals (e.g., mouse, rabbit, rat, guinea pig, etc.).

The terms "control levels" or "control cells" are defined as the standard by which a change is measured, for example, the controls are not subjected to the experiment, but are instead subjected to a defined set of parameters, or the controls are based on pre- or post-treatment levels.

By "contacting" is meant an instance of exposure of at least one substance to another substance. For example, contacting can include contacting a substance, such as a cell, or cell to a test compound described herein. A cell can be contacted with the test compound, for example, by adding the protein or small molecule to the culture medium (by continuous infusion, by bolus delivery, or by changing the medium to a medium that contains the agent) or by adding the agent to the extracellular fluid in vivo (by local delivery, systemic delivery, intravenous injection, bolus delivery, or continuous infusion). The duration of contact with a cell or group of cells is determined by the time the test compound is present at physiologically effective levels or at presumed physiologically effective levels in the medium or extracellular fluid bathing the cell. In the present invention, for example, a virally infected cell (e.g., a, HIV infected cell) or a cell at risk for viral infection (e.g., before, at about the same time, or shortly after HIV infection of the cell) is contacted with a test compound.

"Treatment" or "treating" means to administer a composition to a subject or a system with an undesired condition or at risk for the condition. The condition can be any pathogenic disease, autoimmune disease, cancer or inflammatory condition. The effect of the administration of the composition to the subject can have the effect of but is not limited to reducing the symptoms of the condition, a reduction in the severity of the condition, or the complete ablation of the condition.

By "effective amount" is meant a therapeutic amount needed to achieve the desired result or results, e.g., reducing viral infectivity, blunting physiological functions, altering the qualitative or quantitative nature of the proteins expressed by cell or tissues, and eliminating or reducing disease causing molecules and/or the mRNA or DNA that encodes them, etc.

Herein, "inhibition" or "suppression" means to reduce activity as compared to a control (e.g., activity in the absence of such inhibition). It is understood that inhibition or suppression can mean a slight reduction in activity to the complete ablation of all activity. An "inhibitor" or "suppressor" can be anything that reduces the targeted activity.

"Suppression of viral activity" is defined as a 10%, 20%, 30%, 40%, 50%, 60%, 70%, 80%, 90%, 100%, 2-fold, 10-fold, 100-fold, or 1000-fold suppression of viral activity. Viral activity includes, but is not limited to, viral reproduction, viral shedding, or viral infectivity.

Many methods disclosed herein refer to "systems." It is understood that systems can be, for example, cells, columns, or batch processing containers (e.g., culture plates). A system is a set of components, any set of components that allows for the steps of the method to performed. Typically a system will comprise one or more components, such as a protein(s) or reagent(s). One type of system disclosed would be a cell that comprises both Vif and a test compound, for example. Another type of system would be one that comprises a cell and an infective unit (e.g., an HIV unit). A third type of system might be a chromatography column that has CEM15 or other ARPs bound to the column.

By "virally infected mammalian cell system" or "virally infected" is meant an in vitro or in vivo system infected by a virus. Such a system can include mammalian cellular components; mammalian cells, tissues, or organs; and whole animal systems. By "HIV infectivity" or "viral infectivity" is meant the capacity of an in vitro or in vivo system to become infected by an virus (e.g., an HIV virus).

By "Vif antagonist" is meant any molecule or composition that counteracts, reduces, suppresses, inhibits, blocks, or hinders the activity of a Vif molecule or a fragment thereof. This includes Vif dimerization antagonists, which reduce, suppress, inhibit, block, or hinder the dimerization of Vif. Any time a "Vif antagonist" is mentioned, this includes Vif dimerization antagonists. Also included are agents that block Vif binding to the CEM15, agents that block Vif-mediated poly-ubiquitination of CEM15, and the like.

By "cytidine deaminase activator" is meant any molecule or composition that enhances or increases the activity of a cytidine deaminase molecule or a fragment thereof. By cytidine deaminase activator is also meant deoxycytidine deaminase activator, ARP activator, or any related molecule.

By "deoxycytidine deaminase activator" is meant any molecule or composition that enhances or increases the activity of a deoxycytidine deaminase molecule or a fragment thereof.

By "ARP activator" is meant any molecule or composition that enhances or increases the activity of an APOBEC-1 Related Protein molecule or a fragment thereof.

A "cytidine deaminase-positive cell" means any cell that expresses one or more cytidine deaminases or deoxycytidine deaminases. Such express can be naturally occurring or the cell can include an exogenous nucleic acid that encodes one or more selected deaminases.

"Primers" are a subset of probes that are capable of supporting some type of enzymatic manipulation and that can hybridize with a target nucleic acid such that the enzymatic manipulation can occur. A primer can be made from any combination of nucleotides or nucleotide derivatives or analogs available in the art which do not interfere with the enzymatic manipulation.

There are several examples of cellular and viral mRNA editing in mammalian cells. (Grosjean and Benne (1998); Smith et al. (1997) RNA 3: 1105-23). Two examples of such editing mechanisms are the adenosine to inosine and cytidine to uridine conversions. (Grosjean and Benne (1998); Smith et al. (1996) Trends in Genetics 12:418-24; Krough et al. (1994) J. Mol. Biol. 235:1501-31). Editing can also occur on both RNA and on DNA, and typically these functions are performed by different types of deaminases.

A to I editing involves a family of adenosine deaminases active on RNA (ADARs). ADARs typically have two or more double stranded RNA binding motifs (DRBM) in addition to a catalytic domain whose tertiary structure positions a histidine and two cysteines for zinc ion coordination and a glutamic acid residue as a proton donor. The catalytic domain is conserved at the level of secondary and tertiary structure among ADARs, cytidine nucleoside/nucleotide deaminases and CDARs but differs markedly from that found in adenosine nucleoside/nucleotide deaminases (Higuchi et al (1993) Cell 75:1361-70). ADAR editing sites are found predominantly in exons and are characterized by RNA secondary structure encompassing the adenosine(s) to be edited. In human exon A to I editing, RNA secondary structure is formed between the exon and a 3' proximal sequence with the downstream intron (Grosjean and Benne (1998); Smith et al. (1997) RNA 3: 1105-23; Smith et al. (1996) Trends in Genetics 12:418-24; Maas et al (1996) J. Biol. Chem. 271:12221-26; Reuter et al. (1999) Nature 399:75-80; O'Connell (1997) Current Biol. 7:R437-38). Consequently, A to I editing occurs prior to pre-mRNA splicing in the nucleus. The resultant inosine base pairs with cytosine and codons that have been edited, effectively have an A to G change. ADAR mRNA substrates frequently contain multiple A to I editing sites and each site is selectively edited by an ADAR, such as ADAR1 or ADAR2. ADARs typically function autonomously in editing mRNAs. ADARs bind secondary structure at the editing site through their double stranded RNA binding motifs or DRBMs and perform hydrolytic deamination of adenosine through their catalytic domain.

One example of a Cytosine Deaminase Active on-RNA (CDAR) is APOBEC-1 (apolipoprotein B mRNA editing catalytic subunit 1) (accession # NM_005889) encoded on human chromosome 12. (Grosjean and Benne (1998); Lau et al. (1994) PNAS 91:8522-26; Teng et al (1993) Science 260: 1816-19). APOBEC-1 edits apoB mRNA primarily at nucleotide 6666 (C6666) and to a lesser extent at C8702 (Powell et al. (1987) Cell 50:831-40; Chen et al. (1987) Science 238: 363-366; Smith (1993) Seminars in Cell Biology 4:267-78) in a zinc dependent fashion (Smith et al. (1997) RNA 3:1105-1123). This editing creates an in-frame translation stop codon, UAA, from a glutamine codon, CAA at position C6666 (Grosjean and Benne (1998); Powell et al. (1987) Cell 50:831-840; Chen et al. (1987) Science 238:363-66). The biomedical significance of apoB mRNA editing is that it results in increased production and secretion of B48 containing very low density lipoproteins and correspondingly, a decrease in the abundance of the atherogenic apoB 100 containing low density lipoproteins in serum (Davidson et al. (1988) JBC 262:13482-85; Baum et al. (1990) JBC 265: 19263-70; Wu et al. (1990) JBC 265:12312-12316; Harris and Smith (1992) Biochem. Biophys. Res. Commun. 183: 899-903; Inui et al. (1994) J. Lipid Res. 35:1477-89; Funahashi et al (1995) J. Lipid Res. 36:414-428; Giannoni et al. J. Lipid Res. 36:1664-75; Lau et al. (1995) J. Lipid Res. 36: 2069-78; Phung et al. (1996) Metabolism 45:1056-58; Van Mater et al. (1998) Biochem. Biophys. Res. Commun. 252: 334-39; von Wronski et al. (1998) Metab. Clin. Exp. 7:869-73).

Figure 5A:
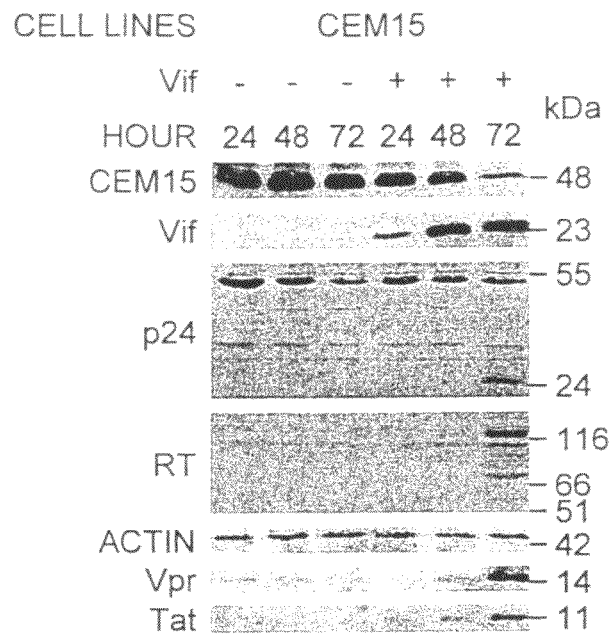
FIG. 5 shows CEM15 suppresses HIV-1 protein abundance. 293T cell lines stably expressing (A) CEM15, (B) DM, and (C) control pIRES-P vector were transiently transfected with proviral HIV-1 plasmids (containing either wild-type Vif(+) or ΔVif(−)). Total cell lysates were prepared at 24, 48, and 72 hours post-transfection, separated by SDS-PAGE and analyzed by immunoblot assay using antibodies reactive with HA (HA-tagged CEM15 and DM), Vif, p24, RT, β-actin, Vpr, or Tat (as denoted on the left). The molecular weight (kDa) of the indicated protein species is given to the right.
Figure 5B:
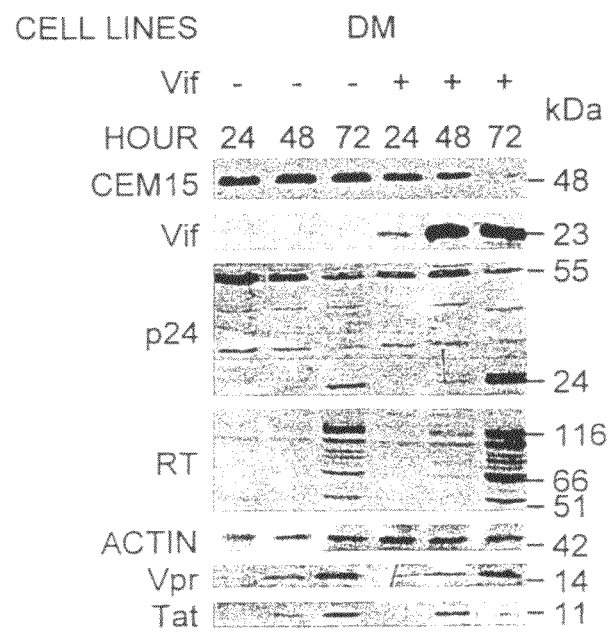
Figure 5C:
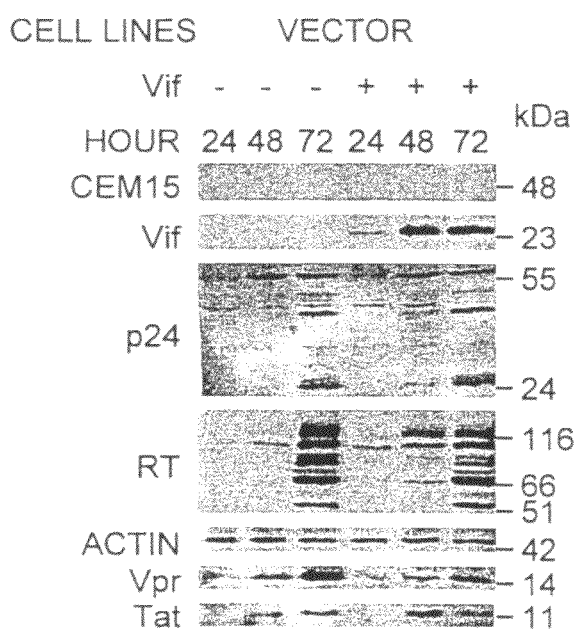
Figure 6A:
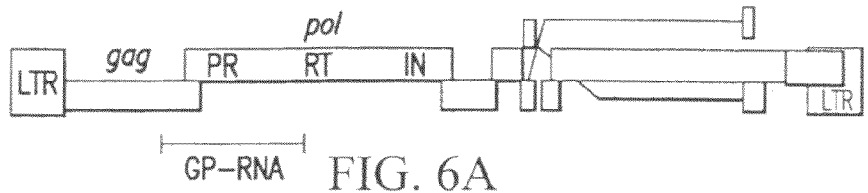
FIG. 6 shows CEM15 suppresses HIV-1 viral RNA abundance. (A) Location of Gag-Pol junction and protease region of HIV-1 genomic RNA corresponding to the GP-RNA probe used for RNA binding and Northern blot analysis. (B) UV crosslinking of increasing concentration of recombinant CEM15 protein (1, 2 and 4 μg protein) to 20 fmol radiolabeled GP-RNA and apoB RNA. (C) Poly A+ RNA abundance for Gag-Pol transcripts in 293T-CEM15 at 24, 48, and 72 hours and DM cells at 48 hours post-transfection with Vif+(black) and ΔVif(white) proviral DNA. Results are expressed as the ratio of viral RNA (GP-RNA region) to endogenous cellular RNA (adenovirus E1A) determined through phosphorimager scanning densitometry analysis of Northern blots.
Figure 6B:
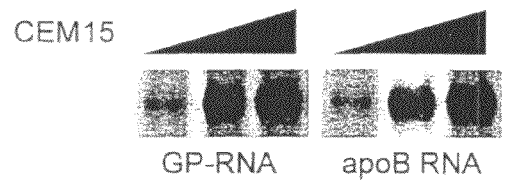
Figure 6C:
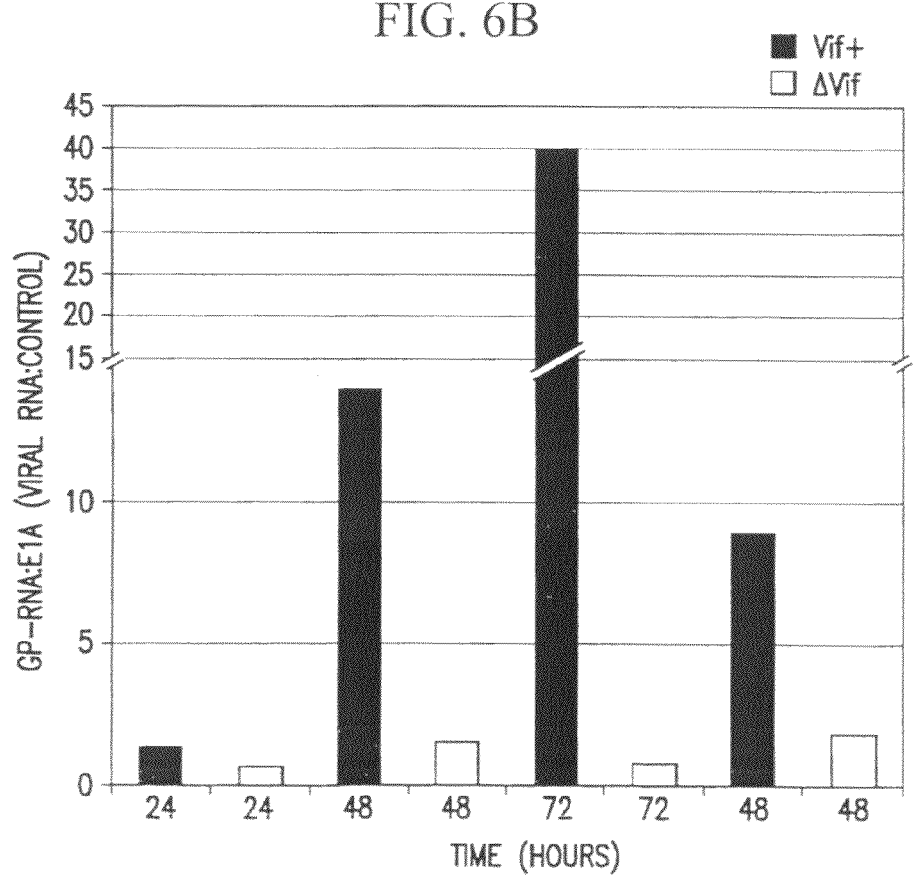

Activation induced deaminase, AID (GenBank accession # BC006296) is encoded on human chromosome 12 (Muto, 2000); (Muramatsu et al. (1999) JBC 274: 18740-76; Muramatsu et al. (2000) Cell 102:553-64; Revy et al. (2000) Cell 102:565-76). AID contains a ZDD (Zinc-dependent deaminase domain) and has 34% amino acid identity to APOBEC-1 (Table 3, FIGS. 5 and 6). Its location on human chromosome 12p13 suggests it may be related to APOBEC-1 by a gene duplication event (Lau, 1994; Muto, 2000). This chromosomal region has been implicated in the autosomal recessive form of Hyper-IgM syndrome (HIGM2) (Revy, 2000). Most patients with this disorder have homozygous point mutations or deletions in three of the five coding exons, leading to missense or nonsense mutations (Revy, P., 2000) Cell. 102: 565-75). Significantly, some patients had missense mutations for key amino acids within AID's ZDD (Revy, 2000; Minegishi, 2000). AID homologous knockout mice demonstrated that AID expression was the rate limiting step for class switch recombination (CSR) and required for an appropriate level of somatic hypermutation SHM (Muramatsu, 2000). The expression of AID controls antibody diversity through multiple gene rearrangements involving mutation of DNA sequence and recombination.

Human APOBEC-2 (Genbank Accession # XM004087) is encoded on chromosome 6 and is expressed uniquely in cardiac and skeletal muscle (Liao et al. Biochem Biophys. Res. Commun. 260:398-404). It shares homology with APOBEC-1's catalytic domain, has a leucine/isoleucine-rich C-terminus and a tandem structural homology of the ZBD in its C-terminus. APOBEC-2 deaminated free nucleotides in vitro but did not have editing activity on apoB mRNA.

Human phorbolin 1, phorbolin 1-related protein, phorbolin-2 and -3 share characteristics with C to U editing enzymes.

(XM_092919) located just 2 kb away from APOBEC-3G, and is thus likely to be an eighth member of the family. The other is at position 12q23, and has similarity to APOBEC-3G.

Figure 2A:
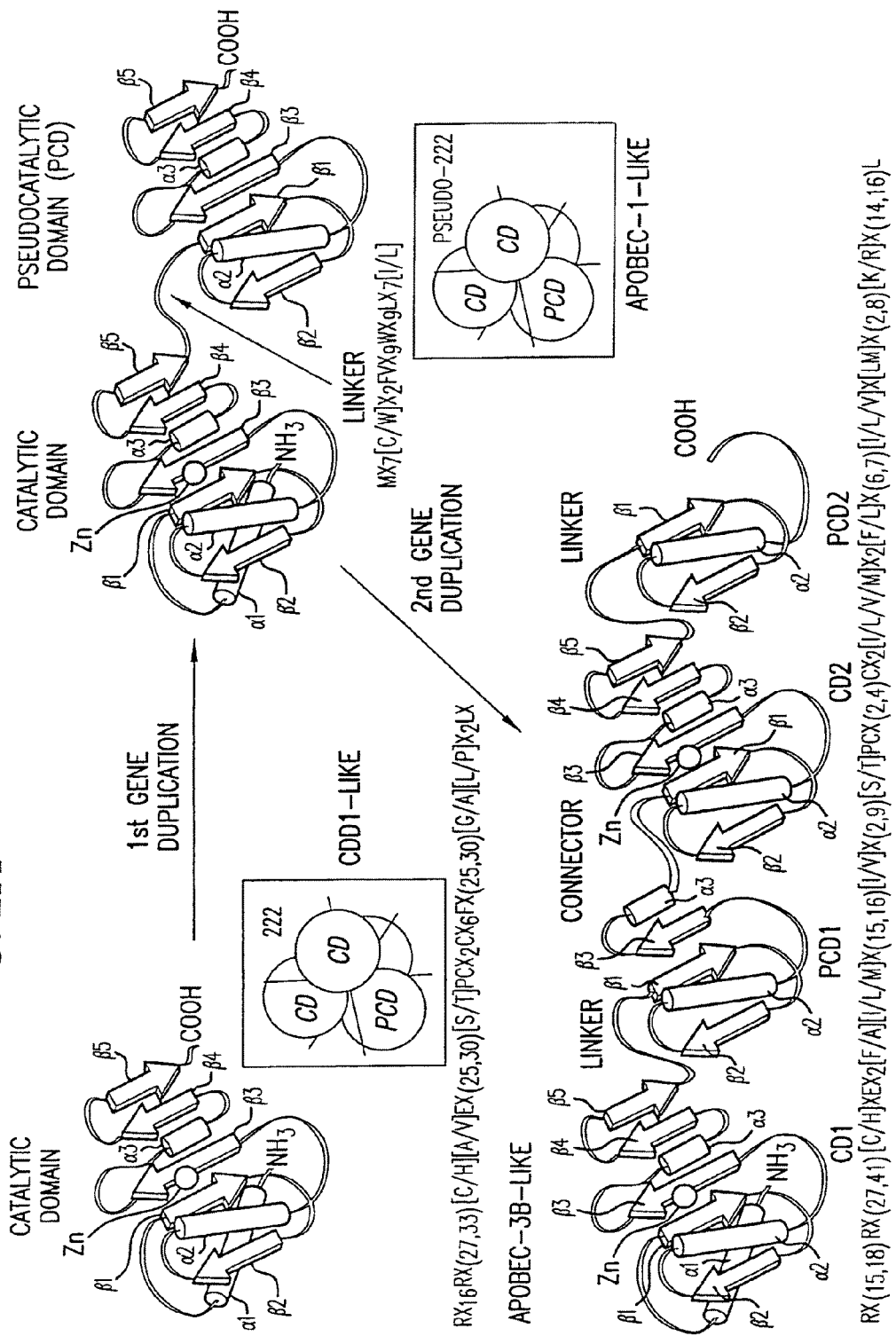
FIG. 2a depicts a gene duplication model for cytidine deaminases. CDD1 belongs to the tetrameric class of cytidine deaminases with a quaternary fold nearly identical to that of the tetrameric cytidine deaminase from *B. subtilis* (Johansson, E., et al., (2002) Biochemistry. 41:2563-70). Such tetrameric enzymes exhibit the classical $\alpha\beta\beta\alpha\beta\alpha\beta\beta$ topology of the Zinc Dependent Deaminase Domain (ZDD) observed first in the Catalytic Domain (CD) of the dimeric enzyme from *E. coli* (Betts, L., et al., (1994) J Mol Biol. 235:635-56). According to the gene duplication model, an ancestral CDD1-like monomer (upper left ribbon) duplicated and fused to produce a bipartite monomer. Over time a C-terminal Pseudo-Catalytic Domain (PCD) arose that lost substrate and Zn2+ binding abilities (upper right ribbon). The model holds that the interdomain CD-PCD junction is joined via flexible linker that features conserved Gly residues necessary for catalytic activity on large polymeric DNA or RNA substrates. The function of the PCD is to stabilize the hydrophobic monomer core and to engage in auxiliary factor binding. The loss of PCD helix $\alpha 1$ can provide a hydrophobic surface were auxiliary factors bind to facilitate substrate recognition thereby regulating catalysis. The enzymes remain oligomeric because each active site comprises multiple polypeptide chains. Modern representatives of the chimeric CDA fold include the enzyme from *E. coli*, as well as APOBEC-1 and AID. Other ARPs such as APOBEC-3G (CEM15) may have arisen through a second gene duplication to produce a pseudo-homodimer on a single polypeptide chain (lower ribbon); structural properties of the connector polypeptide are unknown. Signature sequences compiled from strict structure-based alignments (upper) are shown below respective ribbon diagrams, where X represents any amino acid. Linker regions (lines) and the location of Zn2+ binding (spheres) are depicted. Although experimental evidence suggests APOBEC-3B has reduced Zn2+ binding and exists as a dimer (Jarmuz, A., et al., (2002) Genomics, 79:285-96), modeling studies suggest it will bind Zn2+ (as shown in Wedekind et al. *Trends Genet*, 19(4):207-16, 2003) and may function as a monomer. Inset spheres represent proper (222) CDD1-like quaternary structure symmetry whereas APOBEC-1-like enzymes exhibit pseudo-222 symmetry relating CD and PCD subunits; in the latter enzyme a proper dyad axis relates the polypeptide chains. Finally, APOBEC-3G can fold as a monomer from a single polypeptide chain with each CD and PCD (differently colored spheres in lower left inset box) related by improper 222 symmetry with no strict axes of symmetry.

ARP variants show homology to cytidine deaminases (FIG. 2d). As anticipated from the SBSA, Some of these proteins bind zinc and have RNA binding capacities similar to APOBEC-1 Jarmuz, A., et al., (2002) Genomics, 79:285-96). However, analysis of APOBEC-3A, -3B and -3G revealed them unable to edit apoB mRNA Jarmuz, A., et al., (2002) Genomics, 79:285-96); Muramatsu, M. et al. (1999) J Biol Chem. 274:18470-6). It has been shown that the frequency of deleterious mutations in HIV and impaired infectivity correlated with the expression of CEM15 (APOBEC-3G) (Sheehy et al, 2002; Mariani et al, 2003; Mangeat et al, 2003; Harris et al, 2003; Lecossier et al, 2003.

TABLE 1

| Gene/Chromosomal location | Protein Accession # | Equivalent/Former Names/Variants (Accn #) | Expression | Proposed CDAR/ARP |
|---|---|---|---|---|
| Yeast | | | | |
| CDD1/Chr XII | NP_013346 | — | yeast | ScCDAR-1 |
| Human | | | | |
| APOBEC-1/12p13.1 | AAD00185 | — | small intestine, liver | HsCDAR-1 |
| APOBEC-2/6p21 | NP_006780 | CAB44740 ARCD-1 | cardiac & skeletal muscle | HsARP-1 |
| AID/12p13 | NP_065712 | — | B lymphocytes | HsARP-2 |
| APOBEC-3A/22q13.1 | NP_663745 | Phorbolin-1 (P31941) | keratinocytes | HsARP-3 |
| APOBEC-3B/22q13.1 | Q9U1117 | Phorbolin-3, Phorbolin-1-related (U61084), Phorbolin-2 (Q9UE74), APOBECIL, ARCD-3 | keratinocytes/colon | HsARP-4 |
| APOBEC-3C/22q13.1 | CAB-15271 | Phorbolin-1 (AP165520), ARCD-2/ARCD-4 | spleen/testes/heart/thymus/prostate/ovary/uterus/PBLs | HsARP5 |
| APOBEC-3D/22q13.1 | BF841711 (EST only) | — | hHead & neck cancers | HsARP-6 |
| APOBEC-3E/22q13.1 | pseudogene | ARCD-6 | — | — |
| APOBEC-3D*3E/22q13.1 | NM_145298 | — | uterus | HsARP-7 |
| APOBEC-3F/22q13.1 | BG_758984 (EST only) | ARCD-5 | B lymphocytes | HsARP-8 |
| APOBEC-3G/22q13.1 | NP_068594 | Phorbolin-like-protein, MDS019 (AAH24268), HsCEM15 | spleen/testes/heart/thymus/PBLs/colon/stomach/kidney/uterus/pancreas/placenta/prostate | HsARP-9 |
| 22q13.1 | XP_092919 | — | — | HsARP-10 |
| 12q23 | XP_115170 | — | — | HsARP-11 |
| Mouse | | | | |
| Mm APOBEC-1/6F2 | NP_112436 | — | small intestine/liver/spleen/B lymphocytes/kidney | MmCDAR-1 |
| Mm APOBEC-2/17 | NP_033824 | — | cardiac & skeletal muscle/hair/skin | MmARP-1 |
| mmAID/6F2 | NP_033775 | — | B lymphocytes | MmARP-2 |
| CEM15/15 | NP_084531 | XP_122858 | mammary tumor | MmARP-3 |

Several proteins with homology to APOBEC-1 named Phorbolins 1, 2, 3, and Phorbolin-1 related protein were identified in skin from patients suffering from psoriasis and were shown to be induced (in the case of Phorbolins 1 and 2) in skin treated with phorbol 12-myristate-1-acetate (Muramatsu, M. et al. (1999) J Biol Chem. 274:18470-6). The genes for these proteins were subsequently renamed as members of the APOBEC-3 or ARP family locus (Table 1) (Madsen, P. et al. (1999) J Invest Dermatol. 113:162-9). Bioinformatic studies revealed the presence of two additional APOBEC-1 related proteins in the human genome. One is an expressed gene HIV expressing functional Vif (viral infectivity factor) protein is able to overcome the effects of CEM15 due to the ability of Vif to bind and target fit or ubiquitinate and distruct in the proteasome (Mariani et al., Cell 114:21-31, 2003; Stopal et al. Mol. Cell. 12:591-601, 2003; Yu et al. Nat Struct Mol. Biol. 11:435-42, 2004). In contrast, it is unlikely that APOBEC-3D and 3E function as an APOBEC-1 like editases because they are missing fundamental sequence elements that are required for mRNA editing by both APOBEC-1 and CDD1 (Anant, S. et al. (2001) Am J Physiol Cell Physiol. 281:C1904-16; Dance et al 2001), and experimental evidence shows an impaired ability to coordinate $Zn^{2+}$ and deaminate cytidine Jarmuz, A., et al., (2002) Genomics, 79:285-96). APOBEC-3E appears to be a pseudogene (Jarmuz, A., et al., (2002) Genomics, 79:285-96), yet the EST database shows that APOBEC-3D and APOBEC-3E are alternatively spliced to form a single CD-PCD-CD-PCD encoding transcript.

Additionally, it has been shown that rat APOBEC-1, mouse APOBEC-3, and human APOBEC-3B, are able to inhibit HIV infectivity even in the presence of Vif. Like APOBEC-3G, human APOBEC-3F preferentially restrict vif-deficient virus. The mutation spectra and expression profile of APOBEC-3F indicate that this enzyme, together with APOBEC-3G, accounts for the G to A hypermutation of proviruses described in HIV-infected individuals (Bishop et al., Curr. Bio. 14:1392-1396, 2004). In accordance with this, it has also been shown that APOBEC-3F blocks HIV-1 and is suppressed by both the HIV-1 and HIV-2 Vif proteins (Zheng et al, J Virol 78(11): 6073-6076, 2004; Wiegand et al, EMBO 23:2451-58, 2004). The limited tissue expression, and association with pre-cancerous and cancerous cells (Table 1), and in the case of APOBEC-3G, antagonism of the HIV viral protein Vif shows specific roles for the APOBEC-3 family in growth/cell cycle regulation and antiviral control.

CEM15 (APOBEC-3G) has also been shown to interfere with other retroelements, including but not limited to hepatitis B virus (HBV) and murine leukemia virus (MLV). The methods and compositions described herein are useful with any of these viruses (Bishop et al., Curr. Bio. 14:1392-1396, 2004; Machida et al., PNAS 101(12):4262-67, 2004; Turelli et al., Science, 303:1829, 2004).

Human HIV-1 virus contains a 10-kb single-stranded, positive-sense RNA genome that encodes three major classes of gene products that include: (i) structural proteins such as Gag, Pol and Env; (ii) essential trans-acting proteins (Tat, Rev); and (iii) "auxiliary" proteins that are not required for efficient virus replication in at least some cell culture systems (Vpr, Vif, Vpu, Nef). Among these proteins, Vif is required for efficient virus replication in vivo, as well as in certain host cell types in vitro (Fisher et al. Science 237(4817):888-93, 1987; Strebel et al. Nature 328(6132):728-30, 1987) because of its ability to overcome the action of a cellular antiviral system (Madani et al. J Virol 72(12):10251-5, 1998; Simon et al. Nat Med 4(12):1397-400, 1998).

The in vitro replicative phenotype of vif-deleted molecular clones of HIV-1 is strikingly different in vif-permissive cells (e.g. 293T, SUPT1 and CEM-SS T cell lines), as compared to vif-non-permissive cells (e.g. primary T cells, macrophages, or CEM, H9 and HUT78 T cell lines). In the former cells, vif-deleted HIV-1 clones replicate with an efficiency that is essentially identical to that of wild-type virus, whereas in the latter cells, replication of vif-negative HIV-1 mutants is arrested due to a failure to accumulate reverse transcripts and inability to generate infectious proviral integrants in the host cell (Sova et al. J Virol 67(10):6322-6, 1993; von Schwedler et al. *J Virol* 67(8):4945-55, 1993; Simon et al. *J Virol* 70(8): 5297-305, 1996; Courcoul et al. *J Virol* 69(4):2068-74, 1995). These defects are due to the expression of the host protein CEM15 (Sheehy, A. M., et al., (2002) Nature. 418:646-650) in non-permissive cells for vif minus viruses. CEM15 antiviral activity is derived from effects on viral RNA or reverse transcripts (Sheehy, A. M., et al., (2002) Nature. 418:646-650). CEM15 deaminates dC to dU as the first strand of DNA is being made by reverse transcriptase or soon after its completion, and this results in dG to dA changes at the corresponding positions during second strand DNA synthesis (Harris et al. *Cell* 113:803-809, 2003).

Figure 3:
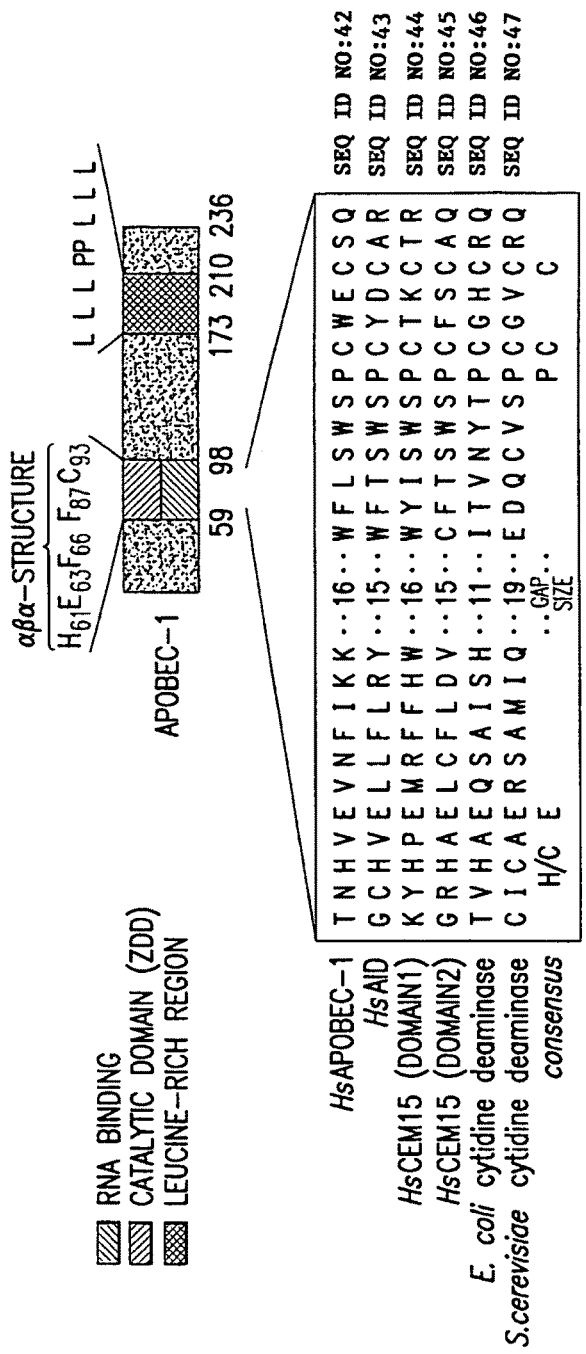
FIG. 3 shows the relation of CEM15 amino acid sequence to APOBEC-1 and other APOBEC-1 Related Proteins (ARPs) by use of standard computational methods based upon amino acid similarity or identity. Amino acid sequence alignments illustrate conservation of $Zn^{2+}$ ligands and key catalytic residues essential to the mechanism of hydrolytic deamination by cytidine deaminases (CDA). Collectively, these amino acids form a signature zinc-dependent deaminase domain (ZDD), present in: (i) APOBEC-1, which mediates C to U editing of apoB mRNA, (ii) the Activation Induced Deaminase (AID), which mediates Somatic Hypermutation (SHM) and Class Switch Recombination (CSR), and (iii) CEM15, which blocks HIV-1 viral infectivity.
Figure 4:
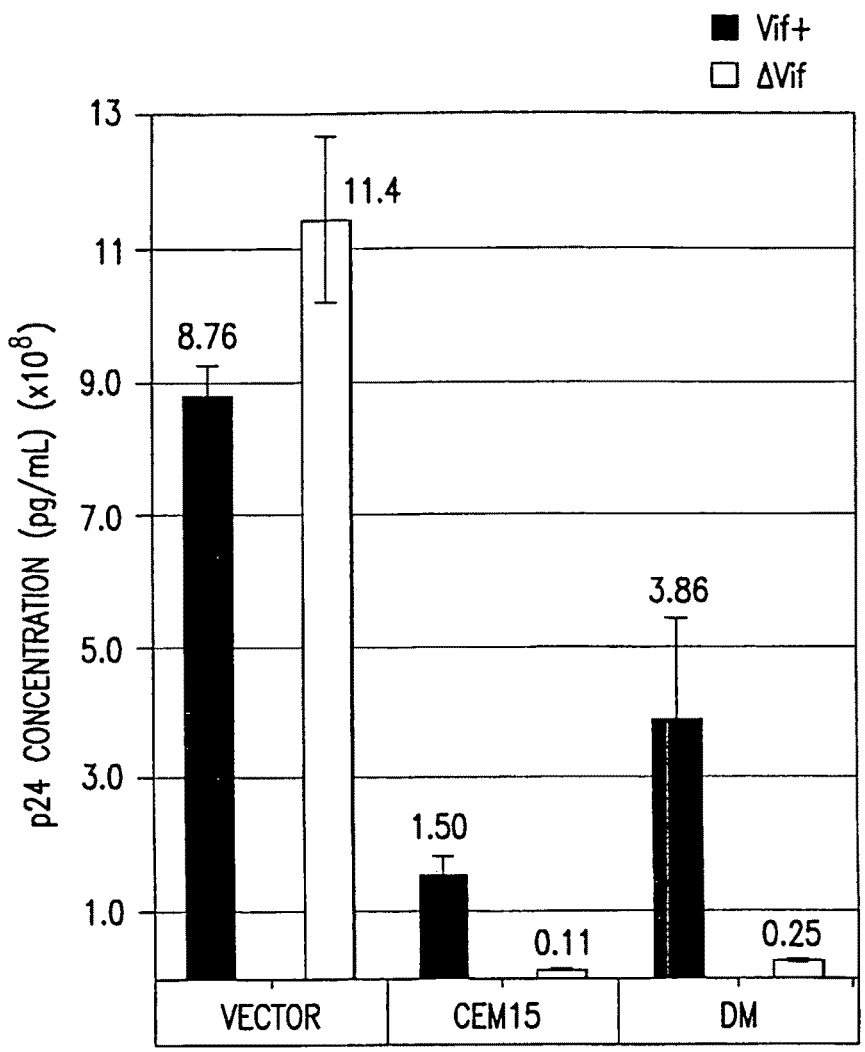
FIG. 4 shows reduced production of pseudotyped HIV-1 viral particles by cells expressing CEM15 or DM. p24 concentration (pg/ml) normalized to % GFP containing cells (as a measure of transfection efficiency) for 293T cells stably expressing pIRES-P vector (n=6), CEM15 (n=6) and DM (n=5), following transfection with wild-type (Vif+) or ΔVif proviral DNA plasmids (black and white bars, respectively). Error bars represent standard deviation calculated from n for each cell line.

Primary sequence alignments (FIG. 3) and the structural constraints relating CDAs to APOBEC-1 indicate that CEM15 evolved from an APOBEC-1-like precursor by gene duplication (Wedekind et al. Trends Genet. 19(4): p. 207-16, 2003). The resulting CEM15 structure exhibits two active sites per polypeptide chain with the topology CD1-PCD1-connector-CD2-PCD2. Knowledge of the structural homology among CDAs and ARPs is sufficient to understand how features of CEM15 contribute to its anti-viral activity.

Vif interacts with CEM15 and induces its poly-ubiquitination and degradation through the proteosome, thereby reducing the abundance of CEM15 and promoting viral infectivity. It has been discovered that Vif homodimers were required for Vif's interaction with CEM15 (Yang et al. J Biol Chem. 278(8): 6596-602 (2003) and U.S. Pat. No. 6,653,443, herein incorporated by reference in their entirety).

Stably expressed CEM15 significantly reduced the level of pseudotyped HIV-1 particles lacking Vif. The reduced viral particle production is the result of a selective suppression of viral RNA leading to reduction in essential HIV-1 proteins. These effects were not observed when Vif was expressed due to the marked reduction of CEM15. Although CEM15 was required to deplete viral particle production its deaminase function was not necessary. The data indicate an antiviral mechanism in producer cells which is potentially significant late during the viral life cycle that involves directly or indirectly the RNA binding ability of CEM15 and does not require virion incorporation of CEM15 deaminase activity during viral replication. Thus, agents that enhance CEM15 selective binding to viral RNA, leading to viral RNA destruction result in a reduction in viral particle production and a reduced viral burden for the subject.

Disclosed herein are methods of predicting the severity of a viral infection in a subject. In one embodiment, the method of predicting the severity of a viral infection in a subject comprises the steps of acquiring a biological sample from the subject; and measuring the level of expression of one or more APOBEC-1 related proteins in the subject, wherein a higher level of expression as compared to a reference level indicates decreased severity. The reference level is a selected control level. Alternatively, the reference level can be from a severely infected subject(s) and a lower level of expression in the test subject would indicate a less severe viral infection.

As disclosed above, greater amounts of APOBEC-1 related proteins can indicate a less severe viral infection. CEM15 contributes to the control of viral replication (Sheehy et al. (2002) Nature 418:646-650; Mariani et al. (2002) Cell 114: 21-31). A number of studies have examined the role of CEM15 in suppressing HIV replication in vitro (Harris et al. (2003) Cell 113:803-809; Zhang et al. (2003) Nature 424:94-98; Mangeat et al. (2003) Nature 424:99-103). Also, CEM15 genetic variants can influence HIV disease progression (An et al. (2004) J. Virol. 78:11070-11076). Increased CEM15 gene expression provides a competitive advantage in that viral Vif is not able to destroy all of the enzyme prior to each round of infection and packaging, and consequently over time mutations in the HIV genome accumulate to the point of debilitating the virus and suppressing infectivity. Consequently, a slower rate of HIV disease progression is observed in patients with elevated CEM15 expression capacity.

In the method described above, the test subject can have a viral infection when the levels of expression are measured. Alternatively, the subject may be free of the viral infection in question, and still be tested to determine the likely response of the subject to a potential viral infection.

Decreased severity can result in an increased longevity in the subject as compared to a control. For example, if greater levels of an APOBEC-1 related protein are found, the individual can be expected to live 1, 2, 3, 4, 5, 6, 7, 8, 9, 10, or 11 months longer, or 1, 2, 3, 4, 5, 6, 7, 8, 9, 10, 11, 12, 13, 14, 15, 16, 17, 18, 19, 20, 21, 22, 23, 24, 25, or more years longer compared to a control. The decreased severity can also comprise a longer asymptomatic period in the subject as compared to a control. For example, the subject can remain asymptomatic for 1, 2, 3, 4, 5, 6, 7, 8, 9, 10, or 11 months longer, or 1, 2, 3, 4, 5, 6, 7, 8, 9, 10, 11, 12, 13, 14, 15, 16, 17, 18, 19, 20, 21, 22, 23, 24, 25, or more years longer compared to a control. Further, the decreased severity can result in reduced symptoms of the viral infection (e.g., reduced fever, reduced inflammation, and reduced secondary infections.)

The decreased severity can be manifest in a number of different ways. For example, the decreased severity can comprise high CD4 counts as compared to a control. The CD4 count has been used as a measurement to determine the strength of the immune system. It can also be used to judge how far a viral infection is advanced (the stage of the disease), and helps predict the risk of complications and opportunistic infections. The CD4 count can be compared with a count obtained from an earlier test in the same subject. The CD4 count can also be used in combination with the viral load test, which measures the level of HIV in the blood, to determine the staging and outlook of the disease. A CD4 count and a viral load test are usually ordered when a subject is diagnosed with a virus, such as HIV, as part of a baseline measurement. Both tests are commonly repeated about four weeks after starting anti-HIV therapy. If treatment is maintained, a CD4 count can be performed every three to four months thereafter, for example.

Normal CD4 counts in adults range from 500 to 1,500 cells per cubic millimeter of blood. In general, the CD4 count goes down as the viral disease progresses. According to public health guidelines, preventive therapy should be started when an HIV-positive person who has no symptoms registers a CD4 count under 350. The Centers for Disease Control and Prevention considers HIV-infected persons who have CD4 counts below 200 to have AIDS, regardless of whether they are symptomatic.

The decreased severity can also comprise lower HIV viremia levels as compared to a control. Quantitative measurements of HIV viremia in peripheral blood have shown that higher virus levels can be correlated with increased risk of clinical progression of HIV disease, and that reductions in plasma virus levels can be associated with decreased risk of clinical progression. Virus levels in the peripheral blood can be quantitated by direct measurement of viral RNA in plasma using nucleic acid amplification technologies, such as the polymerase chain reaction assay, branched DNA assay and nucleic acid sequence-based amplification assay. These assays quantify human immunodeficiency virus (HIV) RNA levels. Plasma viral load (PVL) testing has become a cornerstone of HIV disease management. Initiation of antiretroviral drug therapy is usually recommended when the PVL is 10,000 to 30,000 copies per mL or when CD4+ T-lymphocyte counts are less than 350 to 500 per mm$^3$ (0.35 to 0.50 3 10$^9$ per L). PVL levels usually show a 1- to 2-log reduction within four to six weeks after therapy is started. The goal is no detectable virus in 16 to 24 weeks. Periodic monitoring of PVL is important to promptly identify treatment failure. The same assay can be used for serial PVL testing in the subject. At least two PVL measurements are usually performed before antiretroviral drug therapy is initiated or changed.

Stably expressed CEM15 significantly reduced the level of pseudotyped HIV-1 particles lacking Vif. The reduced viral particle production is the result of a selective suppression of viral RNA leading to reduction in essential HIV-1 proteins. These effects were not observed when Vif was expressed due to the marked reduction of CEM15. The data indicate an antiviral mechanism in producer cells which is potentially significant late during the viral life cycle that involves directly or indirectly the RNA binding ability of CEM15 and does not require virion incorporation of CEM15 deaminase activity during viral replication.

One of ordinary skill in the art at the time of the invention would know how to measure either DNA, mRNA or protein. For example, they can be measured using a blood sample, a cellular extract, or a tissue extract. Urine samples can also be used.

Also disclosed are methods of predicting whether a subject is or will be a long term nonprogressor (LTNP) when infected with a virus. In one embodiment, this method comprises acquiring a biological sample from the subject; and measuring the level of expression of one or more APOBEC-1 related proteins in the subject, wherein a higher level of expression as compared to a reference level (e.g., normal level) indicates the subject is a potential LNTP. If the reference level is that of a rapid progressor, then the difference in the levels may be greater.

A small subset of HIV-infected individuals, known as long-term nonprogressors (LNTPs) have substantially slower rates of disease progression in the absence of therapeutic intervention. Clinically, these LTNPs are usually asymptomatic, maintain high CD4 counts and low HIV viremia levels. The characteristics are therefore of prognostic value in evaluating disease severity. The mechanisms responsible for long-term nonprogression have previously been attributed to defective or less fit HIV variants, strong host immune responses and unique host genetic elements, such as the CCR5 genotype and HLA haplotypes (Buchbinder et al. (1999) Microbes and Infection 1:1113-1120). As disclosed in Example 1, these LTNPs are associated with higher levels of APOBEC-1 related proteins.

As disclosed above, the indication of a LTNP can be manifested in a number of different ways. For example, the decreased severity can comprise high CD4 counts as compared to a control. The decreased severity can also comprise lower HIV viremia levels as compared to a control.

In the methods described above, the subject can have a viral infection when the levels of expression are measured. Alternatively, the subject may be free of the viral infection in question, and still be tested to determine the likely response of the subject as a potential LTNP. The viral infection can be a lentiviral infection, such as HIV-1.

The RNA virus can be selected from the list of viruses consisting of Vesicular stomatitis virus, Hepatitis A virus, Hepatitis C virus, Rhinovirus, Coronavirus, Influenza virus A, Influenza virus B, Measles virus, Respiratory syncytial virus, Adenovirus, Coxsackie virus, Dengue virus, Mumps virus, Poliovirus, Rabies virus, Rous sarcoma virus, Yellow fever virus, Ebola virus, Marburg virus, Lassa fever virus, Eastern Equine Encephalitis virus, Japanese Encephalitis virus, St. Louis Encephalitis virus, Murray Valley fever virus, West Nile virus, Rift Valley fever virus, Rotavirus A, Rotavirus B, Rotavirus C, Sindbis virus, Hantavirus, and Rubella virus.

Also disclosed herein are methods of optimizing antiviral therapy in a subject with a viral infection. In one embodiment, the method comprises the steps of acquiring a biological sample from the subject; detecting the level of expression of one or more APOBEC-1 related proteins in the sample; and adjusting the antiviral therapy according to the levels APOBEC-1 related proteins, thereby optimizing the viral therapy. If the antiviral therapy is associated with high levels of ARP, this is desired.

There are many types of antiviral therapy available. These therapies include, but are not limited to, nucleoside reverse transcriptase inhibitors, non-nucleoside reverse transcriptase inhibitors, nucleotide reverse transcriptase inhibitors, protease inhibitors, fusion inhibitors, integrase inhibitors, or any combination thereof.

The antiviral therapy can be reduced when the expression levels of APOBEC-1 related proteins is high as compared to a reference level. Many of the therapies available to those with a viral infection are expensive and have undesirable side effects. If a subject is expressing high levels of APOBEC-1 related proteins, antiviral therapy can be reduced accordingly, thereby making treatment options customizable to the subject in need thereof. Alternatively, the antiviral therapy can be increased when the expression levels of APOBEC-1 related proteins is low as compared to a reference level. If the levels are found to be below a normal range, or an optimal amount, the treatment can be increased accordingly.

Also disclosed are methods of predicting the level of CD4 cells in a subject, comprising acquiring a biological sample from the subject; and detecting the level of CEM15 expression in the subject, the level of CEM15 correlating with the level of CD4 cells. As disclosed above, the CD4 count has been used as a measurement to determine the strength of the immune system. It can also be used to judge how far a viral infection is advanced (the stage of the disease), and helps predict the risk of complications and opportunistic infections.

Also disclosed is a method of monitoring effectiveness of an antiviral agent in a subject. In one embodiment, these steps comprise detecting expression levels of one or more APOBEC-1 related proteins in a first biological sample from the subject prior to administration of the agent; and detecting expression levels of one or more APOBEC-1 related proteins in a second or any subsequent biological sample from the subject after administration of the agent, an increase in expression levels of the APOBEC-1 related proteins in the second or subsequent sample as compared to the first sample indicating effectiveness of the antiviral agent.

In one example, the agent administered to the subject targets a Vif/CEM15 interaction. The agent can be, for example, a Vif antagonist or a cytidine deaminase activator. The agent can also be selected from the group consisting of nucleoside reverse transcriptase inhibitors, non-nucleoside reverse transcriptase inhibitors, nucleotide reverse transcriptase inhibitors, protease inhibitor, and fusion inhibitors, or a combination thereof.

Also disclosed herein are methods for correlating a specific anti-viral therapy with CEM15 levels in a subject. For example, disclosed is a method of treating a subject infected with a virus with an appropriate antiviral agent, comprising the steps of: identifying a population of subjects with a given range of APOBEC-1 related protein levels; determining which antiviral agent is most effective at the given range of APOBEC-1 related protein levels; and administering an appropriate antiviral agent to the subject in need thereof. Therefore, treatment options can be customized to an individual based on their specific ARP level. By so doing, subjects can be treated based on their specific needs. High levels of CEM15, for example, can dictate that the subject is in need of one type of therapy, while low levels of CEM15 can indicate that a different type of therapy would be more effective. One of ordinary skill in the art is able to determine ARP ranges. These levels can then be coordinated to a given treatment therapy, as disclosed herein.

In the methods disclosed herein, the APOBEC-1 related proteins can be selected from the group consisting of CEM15, APOBEC-3B, APOBEC-3C, APOBEC-3F. APOBEC-3F, has potent activity against virion infectivity factor deficient ($\Delta$vif) human immunodeficiency virus 1 (HIV-1). These enzymes become encapsidated in $\Delta$vif HIV-1 virions and in the next round of infection deaminate the newly synthesized reverse transcripts. APOBEC-3B and APOBEC-3C have potent antiviral activity against simian immuno-deficiency virus (SIV). Both enzymes were encapsidated in SIV virions and were active against $\Delta$vif SIV(mac) and SIV(agm). APOBEC-3B induced abundant G to A mutations in both wild-type and $\Delta$vif SIV reverse transcripts. APOBEC-3C induced substantially fewer mutations. APOBEC-3F was found to be active against SIV and sensitive to SIV(mac) Vif. (Yu et al. J Biol Chem. (2004) Dec. 17; 279(51):53379-86.)

Expression of the APOBEC-1 related protein can be measured by detecting DNA, mRNA or protein levels of the APOBEC-1 related protein. For example, mRNA levels are detected by PCR, such as real time PCR (rtPCR).

PCR is useful for obtaining quantitative information about the expression of many different genes in a sample that can contain as little as a single cell. Since the disclosed methods are quantitative, comparisons of the expression patterns at a quantitative level between a variety of different cell states or cell types can be achieved. In general, total RNA can be isolated from the target sample using any isolation procedure. This RNA can then be used to generate first strand copy DNA (cDNA) using any procedure, for example using random primers or oligo-dt primers or random-oligo-dt primers which are oligo-dT primers coupled, on the 3' end, to short stretches of specific sequence covering all possible combinations, so the primer primes at the junction between the polyA tract and non-poly A tract associated with messenger RNA (mRNA). The cDNA is then used as a template in a PCR reaction. This PCR reaction is performed with primer sets, a forward and a reverse primer, that are specific for the expressed genes, which are to be tracked.

A real time PCR protocol can be used with the methods disclosed herein. These methods, for example, rely on increases in fluorescence at each cycle of PCR through, for example, the release of fluorescein from a quencher sequence while the uniprimer (universal primer) binds to the DNA sequence. Fluorescence approaches used in real-time quantitative PCR are typically based on a fluorescent reporter dye such as SYBR green, FAM, fluorescein, HEX, TET, TAMRA, etc. and a quencher such as DABSYL or Black Hole, for example When the quencher is separated from the probe during the extension phase of PCR, the fluorescence of the reporter can be measured. Systems like Molecular Beacons, Taqman Probes, Scorpion Primers or Sunrise Primers and others use this approach to perform real-time quantitative PCR. Examples of methods and reagents related to real time probes can be found in U.S. Pat. Nos. 5,925,517; 6,103,476; 6,150,097, and 6,037,130, which are incorporated by reference herein at least for material related to detection methods for nucleic acids and PCR methods.

The cDNA sequences of APOBEC-3B (SEQ ID NO: 9), APOBEC-3C (SEQ ID NO: 11), APOBEC-3F (SEQ ID NO: 13) and CEM15 (SEQ ID NO: 5) are highly homologous but have several stretches of non-identity that can be used in the design of specific primers and/or probes for the selective real time PCR quantification of each homolog. APOBEC-3C is half the size of APOBEC-3B, APOBEC-3F and CEM15 and is homologous to only the 3' portion of these transcripts. Consequently, primer and probe combinations within the 5' half of APOBEC-3B, APOBEC-3F and CEM15 does not amplify APOBEC-3C. Importantly APOBEC-3C cDNA sequence between nucleotides 1-194 are not well conserved with comparable regions within the 3' half of APOBEC-3B, APOBEC-3F and CEM15 and therefore can be used in the design of primer and probes for the selective amplification and quantification of APOBEC-3C. For example, SEQ ID NO: 17 discloses nucleotides 1-194 of APOBEC-3C and this sequence, along with fragments or portions thereof, can be used to specifically amplify or detect APOBEC-3C.

Regions of APOBEC-3F sequence with significant divergence that has utility in the selective amplification and quantification this cDNA are apparent from nucleotides 1-60 and 1328-1725 (SEQ ID NOS: 18 and 19). Moreover, APOBEC-3F has a unique 1000 nucleotide long 3' untranslated region that has utility in quantifying this cDNA. SEQ ID NOS: 18 and 19, or fragments or portions thereof, can be used to specifically amplify or detect APOBEC-3F.

APOBEC-3B sequence divergence that has utility in the selective amplification and quantification this cDNA are apparent from nucleotides 1-67 and 910-1007 (SEQ ID NOS 15 and 16). SEQ ID NOS: 15 and 16, or fragments or portions thereof, can be used to specifically amplify or detect APOBEC-3B.

Expression can also be measured by detecting protein levels of APOBEC-1 related proteins. Such detection can occur, for example, by Western blotting. CEM15 protein levels can also be detected using ELISA. Those of skill in the art know how to quantify protein levels using Western blotting or ELISA techniques.

Disclosed herein are methods of screening for an antiviral agent, comprising administering to a subject with a viral infection an agent to be screened; and detecting expression levels of one or more APOBEC-1 related proteins in a biological sample from the subject, an increased expression level indicating an antiviral agent.

As discussed above, an "increased expression level" means an increase in the level of the APOBEC-1 related protein as compared to a control. Therefore, the antiviral agent inhibits or suppresses viral infectivity. An "inhibitor" or "suppressor" can be anything that reduces activity. If the amount of CEM15 is increased in the presence of the composition as compared to the amount of CEM15 in the absence of the composition, the composition can be said to increase the expression level of CEM15.

The screening methods disclosed herein can be used with a high throughput screening assay, for example. The high throughput assay system can comprise an immobilized array of test compounds. Alternatively, the Vif molecule or the cytidine deaminase molecule can be immobilized. There are multiple high throughput screening assay techniques that are well known in the art (for example, but not limited to, those described in Abriola et al., J. Biomol. Screen 4:121-127, 1999; Blevitt et al., J. Biomol. Screen 4:87-91, 2000; Hariharan et al., J. Biomol. Screen 4:187-192, 1999; Fox et al., J. Biomol. Screen 4:183-186, 1999; Burbaum and Sigal, Curr. Opin. Chem. Biol. 1:72-78, 1997; Jayasena, Clin. Chem. 45:1628-1650, 1999; and Famulok and Mayer, Curr. Top. Microbiol. Immunol. 243:123-136, 1999).

Agents with antiviral activity can be identified from large libraries of natural products or synthetic (or semi-synthetic) extracts or chemical libraries according to methods known in the art. Those skilled in the field of drug discovery and development will understand that the precise source of test extracts or compounds is not critical to the screening procedure(s) of the invention. Accordingly, virtually any number of chemical extracts or compounds can be screened using the exemplary methods described herein. Examples of such extracts or compounds include, but are not limited to, plant-, fungal-, prokaryotic- or animal-based extracts, fermentation broths, and synthetic compounds, as well as modification of existing compounds. Numerous methods are also available for generating random or directed synthesis (e.g., semi-synthesis or total synthesis) of any number of chemical compounds, including, but not limited to, saccharide-, lipid-, peptide-, and nucleic acid-based compounds (e.g., but not limited to, antibodies, peptides, and aptamers). Synthetic compound libraries are commercially available, e.g., from Brandon Associates (Merrimack, N.H.) and Aldrich Chemical (Milwaukee, Wis.).

The ability of a test compound to enhance CEM15 expression can be measured by contacting the test compound with a cell in the presence of CEM15, either in vivo or in vitro. The CEM15 function can be, but is not limited to, its cytidine to uridine editing of RNA, or its deoxycytidine to deoxyuridine mutation of DNA, or its suppression of viral activity, or its activity on cancerous or precancerous cells. An "increase in CEM15" is defined as a 10%, 20%, 30%, 40%, 50%, 60%, 70%, 80%, 90%, 100%, 2-fold, 10-fold, 100-fold, or 1000-fold increase in the amount of the CEM15. Also contemplated is an increase in the activity of CEM15.

Disclosed herein are primers, probes, and nucleic acid sequences corresponding to proteins thereof, such as Vif and the ARP family of proteins. For example SEQ ID NOS: 15-16 can be used to amplify APOBEC-3B.

It is understood that as discussed herein the use of the terms homology and identity mean the same thing as similarity. Thus, for example, if the use of the word homology is used between two non-natural sequences it is understood that this is not necessarily indicating an evolutionary relationship between these two sequences, but rather is looking at the similarity or relatedness between their nucleic acid sequences. Many of the methods for determining homology between two evolutionarily related molecules are routinely applied to any two or more nucleic acids or proteins for the purpose of measuring sequence similarity regardless of whether they are evolutionarily related or not.

In general, it is understood that one way to define any known variants and derivatives or those that might arise, of the disclosed genes and proteins herein, is through defining the variants and derivatives in terms of homology to specific known sequences. This identity of particular sequences disclosed herein is also discussed elsewhere herein. In general, variants of genes and proteins herein disclosed typically have at least, about 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99 percent homology to the stated sequence or the native sequence. Those of skill in the art readily understand how to determine the homology of two proteins or nucleic acids, such as genes. For example, the homology can be calculated after aligning the two sequences so that the homology is at its highest level.

Another way of calculating homology can be performed by published algorithms. Optimal alignment of sequences for comparison may be conducted by the local homology algorithm of Smith and Waterman Adv. Appl. Math. 2: 482 (1981), by the homology alignment algorithm of Needleman and Wunsch, J. MoL Biol. 48: 443 (1970), by the search for similarity method of Pearson and Lipman, Proc. Natl. Acad. Sci. U.S.A. 85: 2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by inspection.

The same types of homology can be obtained for nucleic acids by for example the algorithms disclosed in Zuker, M.

Science 244:48-52, 1989, Jaeger et al. *Proc. Natl. Acad. Sci. USA* 86:7706-7710, 1989, Jaeger et al. *Methods Enzymol.* 183:281-306, 1989 which are herein incorporated by reference for at least material related to nucleic acid alignment. It is understood that any of the methods typically can be used and that in certain instances the results of these various methods may differ, but the skilled artisan understands if identity is found with at least one of these methods, the sequences would be said to have the stated identity, and be disclosed herein.

For example, as used herein, a sequence recited as having a particular percent homology to another sequence refers to sequences that have the recited homology as calculated by any one or more of the calculation methods described above. For example, a first sequence has 80 percent homology, as defined herein, to a second sequence if the first sequence is calculated to have 80 percent homology to the second sequence using the Zuker calculation method even if the first sequence does not have 80 percent homology to the second sequence as calculated by any of the other calculation methods. As another example, a first sequence has 80 percent homology, as defined herein, to a second sequence if the first sequence is calculated to have 80 percent homology to the second sequence using both the Zuker calculation method and the Pearson and Lipman calculation method even if the first sequence does not have 80 percent homology to the second sequence as calculated by the Smith and Waterman calculation method, the Needleman and Wunsch calculation method, the Jaeger calculation methods, or any of the other calculation methods. As yet another example, a first sequence has 80 percent homology, as defined herein, to a second sequence if the first sequence is calculated to have 80 percent homology to the second sequence using each of calculation methods (although, in practice, the different calculation methods will often result in different calculated homology percentages).

The term hybridization typically means a sequence driven interaction between at least two nucleic acid molecules, such as a primer or a probe and a gene. Sequence driven interaction means an interaction that occurs between two nucleotides or nucleotide analogs or nucleotide derivatives in a nucleotide specific manner. For example, G interacting with C or A interacting with T are sequence driven interactions. Typically sequence driven interactions occur on the Watson-Crick face or Hoogsteen face of the nucleotide. The hybridization of two nucleic acids is affected by a number of conditions and parameters known to those of skill in the art. For example, the salt concentrations, pH, and temperature of the reaction all affect whether two nucleic acid molecules will hybridize.

Parameters for selective hybridization between two nucleic acid molecules are well known to those of skill in the art. For example, in some embodiments selective hybridization conditions can be defined as stringent hybridization conditions. For example, stringency of hybridization is controlled by both temperature and salt concentration of either or both of the hybridization and washing steps. For example, the conditions of hybridization to achieve selective hybridization may involve hybridization in high ionic strength solution (6×SSC or 6×SSPE) at a temperature that is about 12-25° C. below the Tm (the melting temperature at which half of the molecules dissociate from their hybridization partners) followed by washing at a combination of temperature and salt concentration chosen so that the washing temperature is about 5° C. to 20° C. below the Tm. The temperature and salt conditions are readily determined empirically in preliminary experiments in which samples of reference DNA immobilized on filters are hybridized to a labeled nucleic acid of interest and then washed under conditions of different stringencies. Hybridization temperatures are typically higher for DNA-RNA and RNA-RNA hybridizations. The conditions can be used as described above to achieve stringency, or as is known in the art. (Sambrook et al., Molecular Cloning: A Laboratory Manual, 2nd Ed., Cold Spring Harbor Laboratory, Cold Spring Harbor, N.Y., 1989; Kunkel et al. Methods Enzymol. 1987:154:367, 1987 which is herein incorporated by reference for material at least related to hybridization of nucleic acids). A preferable stringent hybridization condition for a DNA:DNA hybridization can be at about 68° C. (in aqueous solution) in 6×SSC or 6×SSPE followed by washing at 68° C. Stringency of hybridization and washing, if desired, can be reduced accordingly as the degree of complementarity desired is decreased, and further, depending upon the G-C or A-T richness of any area wherein variability is searched for. Likewise, stringency of hybridization and washing, if desired, can be increased accordingly as homology desired is increased, and further, depending upon the G-C or A-T richness of any area wherein high homology is desired, all as known in the art.

Another way to define selective hybridization is by looking at the amount (percentage) of one of the nucleic acids bound to the other nucleic acid. For example, in some embodiments selective hybridization conditions would be when at least about, 60, 65, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 percent of the limiting nucleic acid is bound to the non-limiting nucleic acid. Typically, the non-limiting primer is in for example, 10 or 100 or 1000 fold excess. This type of assay can be performed at under conditions where both the limiting and non-limiting primer are for example, 10 fold or 100 fold or 1000 fold below their $k_d$, or where only one of the nucleic acid molecules is 10 fold or 100 fold or 1000 fold or where one or both nucleic acid molecules are above their $k_d$.

Another way to define selective hybridization is by looking at the percentage of primer that gets enzymatically manipulated under conditions where hybridization is required to promote the desired enzymatic manipulation. For example, in some embodiments selective hybridization conditions would be when at least about, 60, 65, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 percent of the primer is enzymatically manipulated under conditions which promote the enzymatic manipulation, for example if the enzymatic manipulation is DNA extension, then selective hybridization conditions would be when at least about 60, 65, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 percent of the primer molecules are extended. Preferred conditions also include those suggested by the manufacturer or indicated in the art as being appropriate for the enzyme performing the manipulation.

Just as with homology, it is understood that there are a variety of methods herein disclosed for determining the level of hybridization between two nucleic acid molecules. It is understood that these methods and conditions may provide different percentages of hybridization between two nucleic acid molecules, but unless otherwise indicated meeting the parameters of any of the methods would be sufficient. For example if 80% hybridization was required and as long as hybridization occurs within the required parameters in any one of these methods it is considered disclosed herein.

It is understood that those of skill in the art understand that if a composition or method meets any one of these criteria for determining hybridization either collectively or singly it is a composition or method that is disclosed herein.

There are a variety of molecules disclosed herein that are nucleic acid based, including for example the nucleic acids that encode primers and probes. The disclosed nucleic acids are made up of for example, nucleotides, nucleotide analogs, or nucleotide substitutes. Non-limiting examples of these and other molecules are discussed herein. It is understood that for example, when a vector is expressed in a cell, that the expressed mRNA will typically be made up of A, C, G, and U. Likewise, it is understood that if, for example, an antisense molecule is introduced into a cell or cell environment through for example exogenous delivery, it is advantageous that the antisense molecule be made up of nucleotide analogs that reduce the degradation of the antisense molecule in the cellular environment.

A nucleotide is a molecule that contains a base moiety, a sugar moiety and a phosphate moiety. Nucleotides can be linked together through their phosphate moieties and sugar moieties creating an internucleoside linkage. The base moiety of a nucleotide can be adenin-9-yl (A), cytosin-1-yl (C), guanin-9-yl (G), uracil-1-yl (U), and thymin-1-yl (T). The sugar moiety of a nucleotide is a ribose or a deoxyribose. The phosphate moiety of a nucleotide is pentavalent phosphate. An non-limiting example of a nucleotide would be 3'-AMP (3'-adenosine monophosphate) or 5'-GMP (5'-guanosine monophosphate).

A nucleotide analog is a nucleotide which contains some type of modification to either the base, sugar, or phosphate moieties. Modifications to nucleotides are well known in the art and would include for example, 5-methylcytosine (5-me-C), 5-hydroxymethyl cytosine, xanthine, hypoxanthine, and 2-aminoadenine as well as modifications at the sugar or phosphate moieties.

Nucleotide substitutes are molecules having similar functional properties to nucleotides, but which do not contain a phosphate moiety, such as peptide nucleic acid (PNA). Nucleotide substitutes are molecules that will recognize nucleic acids in a Watson-Crick or Hoogsteen manner, but which are linked together through a moiety other than a phosphate moiety. Nucleotide substitutes are able to conform to a double helix type structure when interacting with the appropriate target nucleic acid.

It is also possible to link other types of molecules (conjugates) to nucleotides or nucleotide analogs to enhance for example, cellular uptake. Conjugates can be chemically linked to the nucleotide or nucleotide analogs. Such conjugates include but are not limited to lipid moieties such as a cholesterol moiety. (Letsinger et al., Proc. Natl. Acad. Sci. USA, 1989, 86, 6553-6556), A Watson-Crick interaction is at least one interaction with the Watson-Crick face of a nucleotide, nucleotide analog, or nucleotide substitute. The Watson-Crick face of a nucleotide, nucleotide analog, or nucleotide substitute includes the C2, N1, and C6 positions of a purine based nucleotide, nucleotide analog, or nucleotide substitute and the C2, N3, C4 positions of a pyrimidine based nucleotide, nucleotide analog, or nucleotide substitute.

A Hoogsteen interaction is the interaction that takes place on the Hoogsteen face of a nucleotide or nucleotide analog, which is exposed in the major groove of duplex DNA. The Hoogsteen face includes the N7 position and reactive groups (NH2 or O) at the C6 position of purine nucleotides.

Sequences

There are a variety of sequences related to, for example, CEM15 as well as any other protein disclosed herein that are disclosed on Genbank, and these sequences and others are herein incorporated by reference in their entireties as well as for individual subsequences contained therein.

A variety of sequences are provided herein and these and others can be found in Genbank, at www.pubmed.gov. Those of skill in the art understand how to resolve sequence discrepancies and differences and to adjust the compositions and methods relating to a particular sequence to other related sequences. Primers and/or probes can be designed for any sequence given the information disclosed herein and known in the art.

Disclosed are compositions including primers and probes, which are capable of interacting with the genes disclosed herein. In certain embodiments the primers are used to support DNA amplification reactions. Typically the primers will be capable of being extended in a sequence specific manner. Extension of a primer in a sequence specific manner includes any methods wherein the sequence and/or composition of the nucleic acid molecule to which the primer is hybridized or otherwise associated directs or influences the composition or sequence of the product produced by the extension of the primer. Extension of the primer in a sequence specific manner therefore includes, but is not limited to, PCR, DNA sequencing, DNA extension, DNA polymerization, RNA transcription, or reverse transcription. Techniques and conditions that amplify the primer in a sequence specific manner are preferred. In certain embodiments the primers are used for the DNA amplification reactions, such as PCR or direct sequencing. It is understood that in certain embodiments the primers can also be extended using non-enzymatic techniques, where for example, the nucleotides or oligonucleotides used to extend the primer are modified such that they will chemically react to extend the primer in a sequence specific manner. Typically the disclosed primers hybridize with the nucleic acid or region of the nucleic acid or they hybridize with the complement of the nucleic acid or complement of a region of the nucleic acid.

Disclosed is an isolated nucleic acid sequence comprising a sequence at least 80% identical to SEQ ID NO: 1 (5' CGCAGCCTGTGTCAGAAAAG3'). The nucleic acid sequence comprising the nucleotide sequence of SEQ ID NO: 1, or variants or fragments thereof, wherein the variant or fragment comprises a specific CEM15 primer. Also contemplated is an isolated nucleic acid sequence comprising at least five consecutive nucleotides of SEQ ID NO: 1, wherein the nucleic acid sequence comprises a specific CEM15 primer. Also contemplated is an isolated nucleic acid sequence comprising the sequence of SEQ ID NO: 1.

Disclosed herein is an isolated nucleic acid sequence comprising a sequence at least 80% identical to SEQ ID NO: 2 (5' CCAACAGTGCTGAAATTCGTCATA3'). Contemplated herein is an isolated nucleic acid sequence comprising the nucleotide sequence of SEQ ID NO: 2, or variants or fragments thereof, wherein the variant or fragment comprises a specific CEM15 primer. Described herein is an isolated nucleic acid sequence comprising at least five consecutive nucleotides of SEQ ID NO: 2, wherein the nucleic acid sequence comprises a specific CEM15 primer. Further disclosed is an isolated nucleic acid sequence comprising SEQ ID NO: 2.

Disclosed herein is an isolated nucleic acid sequence comprising a sequence at least 80% identical to SEQ ID NO: 3 (5' GTGCCACCATGAAGA3'). Described herein is an isolated nucleic acid sequence comprising the nucleotide sequence of SEQ ID NO: 3, or variants or fragments thereof, wherein the variant or fragment comprises a specific CEM15 probe. Also described is an isolated nucleic acid sequence comprising at least five consecutive nucleotides of SEQ ID NO: 3, wherein the nucleic acid sequence comprises a specific CEM15 probe.

Disclosed are antiviral agents identified by the screening methods disclosed herein. The antiviral agent can increase the expression level of CEM15 in a subject. Alternatively, the antiviral agent can bind, or otherwise interact, with a cytidine deaminase or deoxycytidine deaminase, thereby enhancing the normal activity of the cytidine deaminase or deoxycytidine deaminase. For example, a cytidine deaminase activator can interact with CEM15 and enhance the binding of CEM15 to a virus. Conversely, a cytidine deaminase activator can interact with the binding of Vif to a CEM15 molecule, thereby suppressing the activity of Vif, and indirectly enhancing CEM15 binding to HIV.

In the methods disclosed herein, molecules such as CEM15 and Vif can be used in assays. These molecules can be, for example, chimeric proteins. By "chimeric protein" is meant any single polypeptide unit that comprises two distinct polypeptide domains joined by a peptide bond, optionally by means of an amino acid linker, or a non-peptide bond, wherein the two domains are not naturally occurring within the same polypeptide unit. Typically, such chimeric proteins are made by expression of a cDNA construct but could be made by protein synthesis methods known in the art. These chimeric proteins are useful in screening compounds, as well as with the compounds identified by the methods disclosed herein.

Figures 1, 2B:
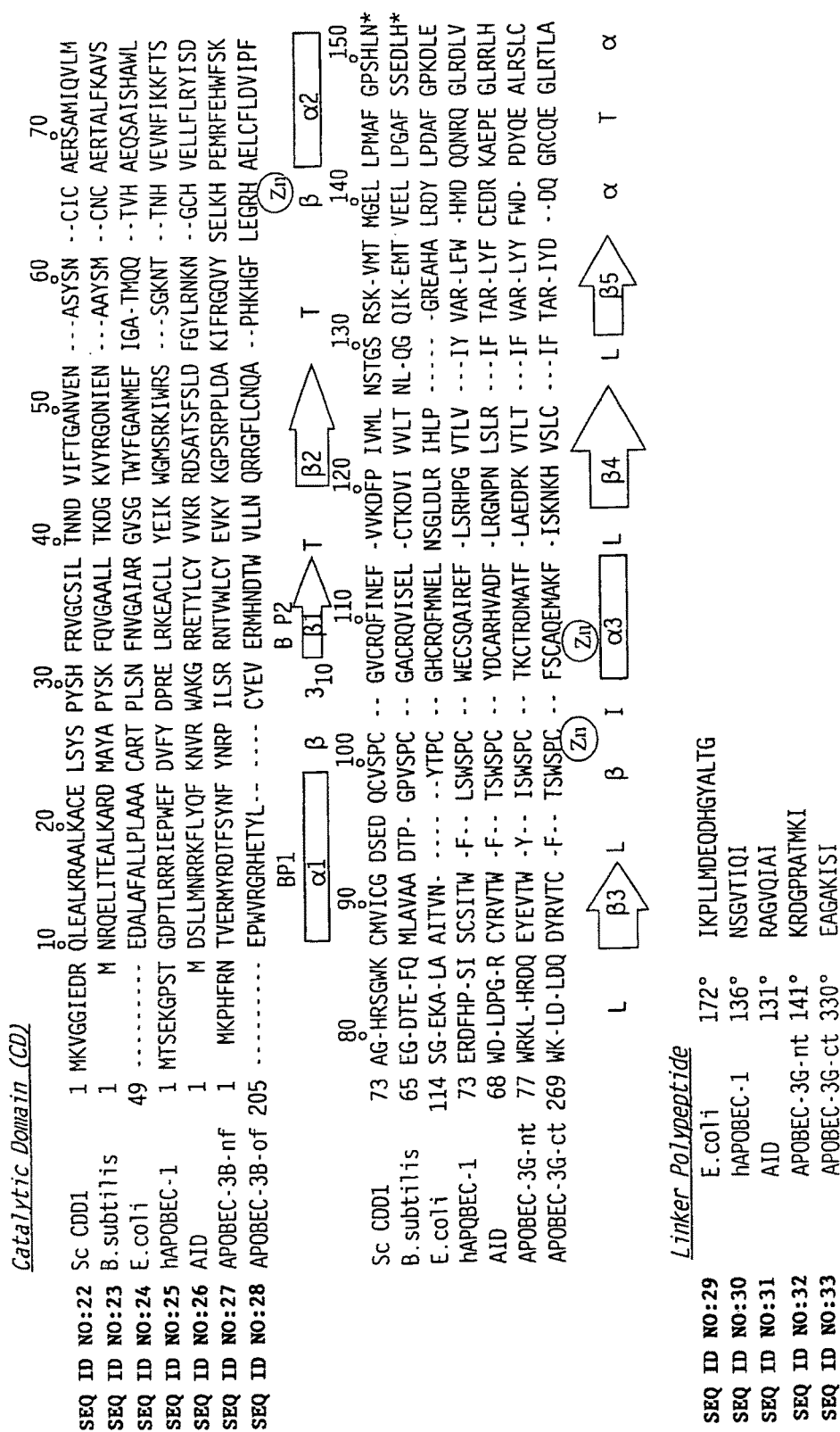
FIG. 2b depicts the structure based sequence alignment for ARPs. Sequences from human APOBEC-1, AID, and APOBEC-3G were aligned based upon a main-chain alpha-carbon least-squares superposition of the known cytidine deaminase three dimensional crystal structures from *E. coli*, *B. subtilis* and *S. cerevisiae* (FIG. 2c). Amino acid sequence alignments were optimized to minimize gaps in major secondary structure elements, which are depicted as tubes ($\alpha$-helices) and arrows ($\beta$-strands) in FIG. 2b. Additionally, loops, turns, and insertions of FIG. 2b are marked L and T and i, respectively. L-C1 and L-C2 represent distinct loop structures in the dimeric versus tetrameric cytidine deaminases. Sections of basic residues that overlap the bipartite NLS of APOBEC-1 are marked BP-1 and BP-2.
Figure 2C:
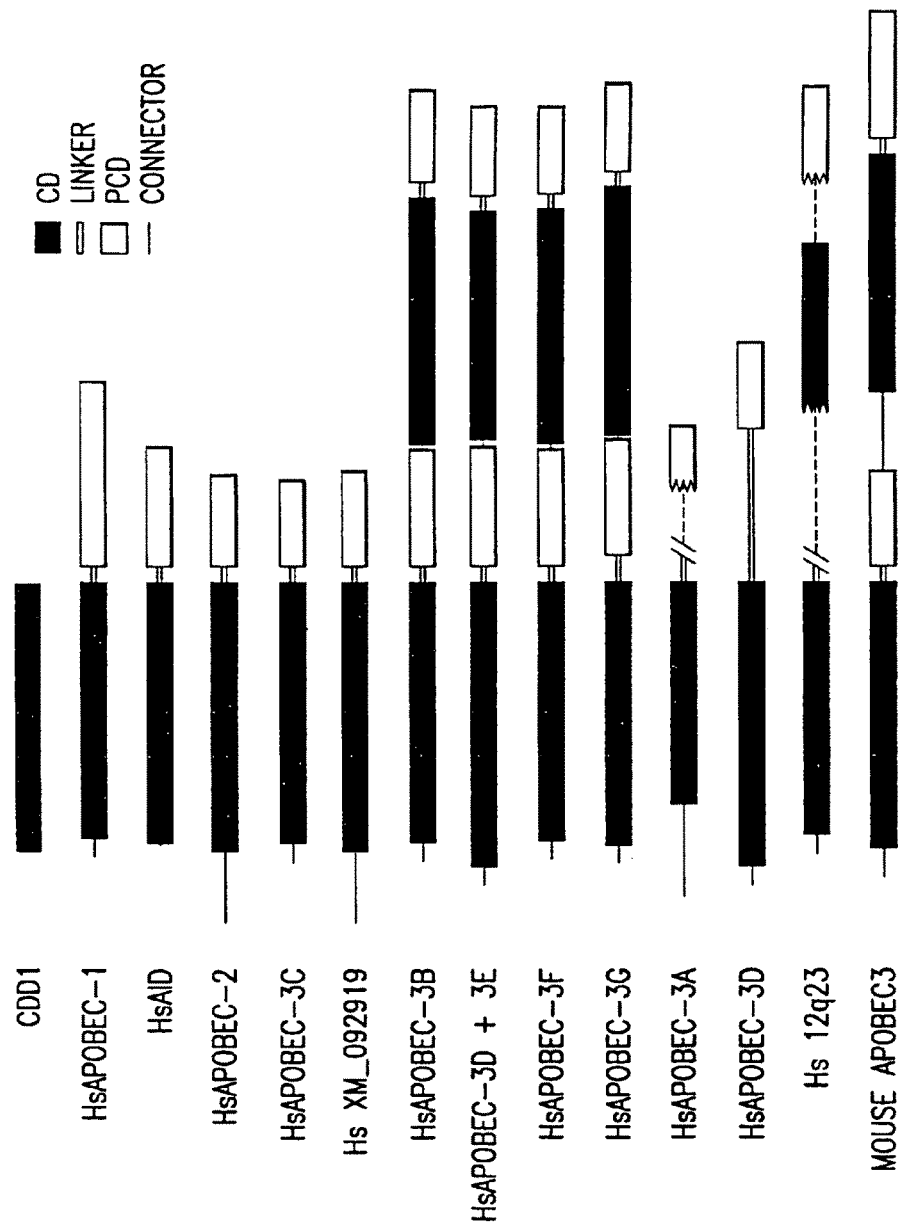

The compositions disclosed herein can also be fragments or derivatives of a naturally occurring deaminase or viral infectivity factor. A "fragment" is a polypeptide that is less than the full length of a particular protein or functional domain. By "derivative" or "variant" is meant a polypeptide having a particular sequence that differs at one or more positions from a reference sequence. The fragments or derivatives of a full length protein preferably retain at least one function of the full length protein. For example, a fragment or derivative of a deaminase includes a fragment of a deaminase or a derivative deaminase that retains at least one binding or deaminating function of the full length protein. By way of example, the fragment or derivative can include a Zinc-Dependent Cytidine Deaminase domain or can include 20, 30, 40, 50, 60, 70 80, 90% similarity with the full length deaminase. The fragment or derivative can include conservative or non-conservative amino acid substitutions. The fragment or derivative can include a linker sequence joining a catalytic domain (CD) to a pseudo-catalytic domain (PCD) and can have the domain structure CD-PCD-CD-PCD or any repeats thereof. The fragment or derivative can comprise a CD. Other fragments or derivatives are identified by structure-based sequence alignment (SBSA) as shown herein. See FIG. 2b that reveals the consensus structural domain attributes of APOBEC-1 and ARPs (FIG. 2c). The fragment or derivative optionally can form a homodimer or a homotetramer. Also disclosed are chimeric proteins, wherein the deaminase domain is a fragment or derivative of CEM15 having deaminase function.

"Deaminases" include deoxycytidine deaminase, cytidine deaminase, adenosine deaminase, RNA deaminase, DNA deaminase, and other deaminases. Optionally, the deaminase is APOBEC-1 (see international patent application designated PCT/US02/05824, which is incorporated herein by reference in its entirety for APOBEC-1, chimeric proteins related thereto, and uses thereof) (Gen Bank Accession # NP_001635), REE (see U.S. Pat. No. 5,747,319, which is incorporated herein by reference in its entirety for REE and uses thereof), or REE-2 (see U.S. Pat. No. 5,804,185, which is incorporated herein by reference in its entirety for REE-2 and uses thereof). Deaminases as described herein can include the following structural features: three or more CDD-1 repeats, two or more functional CDD-1 repeats, one or more zinc binding domains (ZBDs), binding site(s) for mooring sequences, or binding sites for auxiliary RNA binding proteins. Deaminases optionally edit viral RNA, host cell mRNA, viral DNA, host cell DNA or any combination thereof. One deaminase described herein is CEM15. CEM15 is homologous to Phorbolin or APOBEC-3G (see, for example, Accession #NP_068594). The names CEM15 and APOBEC-3G can be used interchangeably. CEM15 reduces retroviral infectivity as an RNA or DNA editing enzyme.

By "deaminating function" is meant a deamination of a nucleotide (e.g., cytidine, deoxycytidine, adenosine, or deoxyadenosine). Deaminating function is detected by measuring the amount of deaminated nucleotide, according to the methods taught herein, wherein such levels are above background levels (preferably at least 1.5-2.5 times the background levels of the assay.)

Protein variants and derivatives are well understood to those of skill in the art and in can involve amino acid sequence modifications. For example, amino acid sequence modifications typically fall into one or more of three classes: substitutional, insertional or deletional variants. Insertions include amino and/or carboxyl terminal fusions as well as intrasequence insertions of single or multiple amino acid residues. Insertions ordinarily will be smaller insertions than those of amino or carboxyl terminal fusions, for example, on the order of one to four residues. Immunogenic fusion protein derivatives, such as those described in the examples, are made by fusing a polypeptide sufficiently large to confer immunogenicity to the target sequence by crosslinking in vitro or by recombinant cell culture transformed with DNA encoding the fusion. Deletions are characterized by the removal of one or more amino acid residues from the protein sequence. Typically, no more than about from 2 to 6 residues are deleted at any one site within the protein molecule. These variants ordinarily are prepared by site specific mutagenesis of nucleotides in the DNA encoding the protein, thereby producing DNA encoding the variant, and thereafter expressing the DNA in recombinant cell culture. Techniques for making substitution mutations at predetermined sites in DNA having a known sequence are well known, for example M13 primer mutagenesis and PCR mutagenesis. Amino acid substitutions are typically of single residues, but can occur at a number of different locations at once; insertions usually will be on the order of about from 1 to 10 amino acid residues; and deletions will range about from 1 to 30 residues. Deletions or insertions preferably are made in adjacent pairs, i.e. a deletion of 2 residues or insertion of 2 residues. Substitutions, deletions, insertions or any combination thereof may be combined to arrive at a final construct. The mutations must not place the sequence out of reading frame and preferably will not create complementary regions that could produce secondary mRNA structure. Substitutional variants are those in which at least one residue has been removed and a different residue inserted in its place. Such substitutions generally are made in accordance with the following Table 2 and are referred to as conservative substitutions.

Substantial changes in function or immunological identity are made by selecting substitutions that are less conservative, i.e., selecting residues that differ more significantly in their effect on maintaining (a) the structure of the polypeptide backbone in the area of the substitution, for example as a sheet or helical conformation, (b) the charge or hydrophobicity of the molecule at the target site or (c) the bulk of the side chain. The substitutions which in general are expected to produce the greatest changes in the protein properties will be those in which (a) a hydrophilic residue, e.g. seryl or threonyl, is substituted for (or by) a hydrophobic residue, e.g. leucyl, isoleucyl, phenylalanyl, valyl or alanyl; (b) a cysteine or proline is substituted for (or by) any other residue; (c) a residue having an electropositive side chain, e.g., lysyl, arginyl, or histidyl, is substituted for (or by) an electronegative residue, e.g., glutamyl or aspartyl; or (d) a residue having a bulky side chain, e.g., phenylalanine, is substituted for (or by) one not having a side chain, e.g., glycine, in this case, (e) by increasing the number of sites for sulfation and/or glycosylation.

TABLE 2

Amino Acid Substitutions

| Original Residue | Exemplary Substitutions |
| --- | --- |
| Ala | Ser |
| Arg | Lys |
| Asn | Gln |
| Asp | Glu |
| Cys | Ser |
| Gln | Asn |
| Glu | Asp |
| Gly | Pro |
| His | Gln |
| Ile | Leu; Val |
| Leu | Ile; Val |
| Lys | Arg; Gln |
| Met | Leu; Ile |
| Phe | Met; Leu; Tyr |
| Pro | Gly |
| Ser | Thr |
| Thr | Ser |
| Trp | Tyr |
| Tyr | Trp; Phe |
| Val | Ile; Leu |

For example, the replacement of one amino acid residue with another that is biologically and/or chemically similar is known to those skilled in the art as a conservative substitution. For example, a conservative substitution would be replacing one hydrophobic residue for another, or one polar residue for another. The substitutions include combinations such as, for example, Gly, Ala; Val, Ile, Leu; Asp, Glu; Asn, Gln; Ser, Thr; Lys, Arg; and Phe, Tyr. Such conservatively substituted variations of each explicitly disclosed sequence are included within the mosaic polypeptides provided herein.

Substitutional or deletional mutagenesis can be employed to insert sites for N-glycosylation (Asn-X-Thr/Ser) or O-glycosylation (Ser or Thr). Deletions of cysteine or other labile residues also may be desirable. Deletions or substitutions of potential proteolysis sites, e.g. Arg, is accomplished for example by deleting one of the basic residues or substituting one by glutaminyl or histidyl residues.

Certain post-translational derivatizations are the result of the action of recombinant host cells on the expressed polypeptide. Glutaminyl and asparaginyl residues are frequently post-translationally deamidated to the corresponding glutamyl and asparyl residues. Alternatively, these residues are deamidated under mildly acidic conditions. Other post-translational modifications include hydroxylation of proline and lysine, phosphorylation of hydroxyl groups of seryl or threonyl residues, methylation of the o-amino groups of lysine, arginine, and histidine side chains (T. E. Creighton, Proteins: Structure and Molecular Properties, W. H. Freeman & Co., San Francisco pp 79-86 [1983]), acetylation of the N-terminal amine and, in some instances, amidation of the C-terminal carboxyl.

The compositions disclosed herein can be used as targets in combinatorial chemistry protocols or other screening protocols to isolate molecules that possess desired functional properties related to increasing the level of an ARPs in a subject.

As disclosed above, the disclosed compositions, such as cytidine deaminases or deoxycytidine deaminases (e.g., CEM15 and other ARPs) or Vif can be used as targets for any combinatorial technique to identify molecules or macromolecular molecules that interact with the disclosed compositions in a desired way or mimic their function. The nucleic acids, peptides, and related molecules disclosed herein can be used as targets for the combinatorial approaches.

It is understood that when using the disclosed compositions in combinatorial techniques or screening methods, molecules, such as macromolecular molecules, will be identified that have particular desired properties such as stimulation or the target molecule's function. The molecules identified and isolated when using the disclosed compositions, such as, CEM15, other ARPs, or Vif, are also disclosed. Thus, the products produced using the combinatorial or screening approaches that involve the disclosed compositions, such as, CEM15, other ARPs, or Vif are also disclosed. Such molecules include Vif antagonists and cytidine deaminase activators.

Combinatorial chemistry includes but is not limited to all methods for isolating small molecules or macromolecules that are capable of binding either a small molecule or another macromolecule like Vif or cytidine deaminase (e.g., CEM15), typically in an iterative process. Proteins, oligonucleotides, and sugars are examples of macromolecules. For example, oligonucleotide molecules with a given function, catalytic or ligand-binding, can be isolated from a complex mixture of random oligonucleotides in what has been referred to as "in vitro genetics" (Szostak, TIBS 19:89, 1992). One synthesizes a large pool of molecules bearing random and defined sequences and subjects that complex mixture, for example, approximately 1015 individual sequences in 100 mg of a 100 nucleotide RNA, to some selection and enrichment process. Through repeated cycles of affinity chromatography and PCR amplification of the molecules bound to the ligand on the column, Ellington and Szostak (1990) estimated that 1 in 1010 RNA molecules folded in such a way as to bind a small molecule dyes. DNA molecules with such ligand-binding behavior have been isolated as well (Ellington and Szostak, 1992; Bock et al, 1992). Techniques aimed at similar goals exist for small organic molecules, proteins, antibodies and other macromolecules known to those of skill in the art. Screening sets of molecules for a desired activity whether based on small organic libraries, oligonucleotides, or antibodies is broadly referred to as combinatorial chemistry. Combinatorial techniques are particularly suited for defining binding interactions between molecules and for isolating molecules that have a specific binding activity, often called aptamers when the macromolecules are nucleic acids.

As used herein combinatorial methods and libraries include traditional screening methods and libraries as well as methods and libraries used in interactive processes.

The disclosed compositions can be used as targets for any molecular modeling technique to identify either the structure of the disclosed compositions or to identify potential or actual molecules, such as small molecules, which interact in a desired way with the disclosed compositions. The compounds disclosed herein can be used as targets in any molecular modeling program or approach.

It is understood that when using the disclosed compositions in modeling techniques, molecules, such as macromolecular molecules, will be identified that have particular desired properties such as inhibition, suppression, or stimulation or the target molecule's function.

One way to isolate molecules that bind a molecule of choice is through rational design. This is achieved through structural information and computer modeling. Computer modeling technology allows visualization of the three-dimensional atomic structure of a selected molecule and the rational design of new compounds that will interact with the molecule. The three-dimensional construct typically depends on data from x-ray crystallographic analyses or NMR imaging of the selected molecule. The molecular dynamics require force field data. The computer graphics systems enable prediction of how a new compound will link to the target molecule and allow experimental manipulation of the structures of the compound and target molecule to perfect binding specificity. Prediction of what the molecule-compound interaction will be when small changes are made in one or both requires molecular mechanics software and computationally intensive computers, usually coupled with user-friendly, menu-driven interfaces between the molecular design program and the user.

Examples of molecular modeling systems are the CHARMm and QUANTA programs, Polygen Corporation, Waltham, Mass. CHARMm performs the energy minimization and molecular dynamics functions. QUANTA performs the construction, graphic modeling and analysis of molecular structure. QUANTA allows interactive construction, modification, visualization, and analysis of the behavior of molecules with each other.

A number of articles review computer modeling of drugs interactive with specific proteins, such as Rotivinen, et al., 1988 Acta Pharmaceutica Fennica 97, 159-166; Ripka, New Scientist 54-57 (Jun. 16, 1988); McKinaly and Rossmann, 1989 Annu. Rev. Pharmacol. Toxiciol. 29, 111-122; Perry and Davies, QSAR: Quantitative Structure-Activity Relationships in Drug Design pp. 189-193 (Alan R. Liss, Inc. 1989); Lewis and Dean, 1989 Proc. R. Soc. Lond. 236, 125-140 and 141-162; and, with respect to a model enzyme for nucleic acid components, Askew, et al., 1989 J. Am. Chem. Soc. 111, 1082-1090. Other computer programs that screen and graphically depict chemicals are available from companies such as BioDesign, Inc., Pasadena, Calif., Allelix, Inc, Mississauga, Ontario, Canada, and Hypercube, Inc., Cambridge, Ontario. Although these are primarily designed for application to drugs specific to particular proteins, they can be adapted to design of molecules specifically interacting with specific regions of DNA or RNA, once that region is identified.

Although described above with reference to design and generation of compounds which can alter binding, one can also screen libraries of known compounds, including natural products or synthetic chemicals, and biologically active materials, including proteins, for compounds which alter substrate binding or enzymatic activity.

Also described is a compound that is identified or designed as a result of any of the disclosed methods can be obtained (or synthesized) and tested for its biological activity, e.g., competitive stimulation of CEM15 or inhibition or suppression of viral infectivity.

Disclosed herein are computer systems and databases containing information related to APOBEC-1 Related Proteins and subjects. Since subjects will vary depending on numerous parameters including, but not limited to, race, age, weight, medical history etc., as more information is gathered on populations, the database can contain information classified by race, age, weight, medical history etc., such that one of skill in the art can assess the subject's risk of developing AIDS, the subject's susceptibility to a viral infection, the subject's ability to mount an immune response and/or the subject's responsiveness to a therapeutic agent based on information more closely associated with the subject's demographic profile.

The analysis of complex systems such as biological organisms is aided by the use of relational database systems for storing and retrieving large amounts of biological data. The advent of high-speed wide area networks and the Internet, together with the client/server based model of relational database management systems, is particularly well-suited for allowing researchers to access and meaningfully analyze large amounts of biological data given the appropriate hardware and software computing tools.

The present invention provides a computer system comprising a) a database including records comprising a plurality of reference information comprising the ARP level and associated diagnosis and therapy data; and b) a user interface capable of receiving a selection of one or more sets of information related to the subject's demographic profile.

Computer readable media include magnetically readable media, optically readable media, electronically readable media and magnetic/optical media. For example, the computer readable media may be a hard disc, a floppy disc, a magnetic tape, CD-ROM, DVD, RAM, or ROM as well as other types of other media known to those skilled in the art.

Embodiments of the present invention include systems, particularly computer systems which contain the population information described herein. As used herein, "a computer system" refers to the hardware components, software components, and data storage components used to store and/or analyze the information of the present invention or other relevant information. The computer system preferably includes the computer readable media described above, and a processor for accessing and manipulating the data.

Preferably, the computer is a general purpose system that comprises a central processing unit (CPU), one or more data storage components for storing data, and one or more data retrieving devices for retrieving the data stored on the data storage components. A skilled artisan can readily appreciate that any one of the currently available computer systems are suitable.

In one particular embodiment, the computer system includes a processor connected to a bus which is connected to a main memory, preferably implemented as RAM, and one or more data storage devices, such as a hard drive and/or other computer readable media having data recorded thereon. In some embodiments, the computer system further includes one or more data retrieving devices for reading the data stored on the data storage components. The data retrieving device may represent, for example, a floppy disk drive, a compact disk drive, a magnetic tape drive, a hard disk drive, a CD-ROM drive, a DVD drive, etc. In some embodiments, the data storage component is a removable computer readable medium such as a floppy disk, a compact disk, a magnetic tape, etc. containing control logic and/or data recorded thereon. The computer system may advantageously include or be programmed by appropriate software for reading the control logic and/or the data from the data storage component once inserted in the data retrieving device. Software for accessing and processing the information of the invention (such as search tools, compare tools, modeling tools, etc.) may reside in main memory during execution.

Another aspect of the present invention is a method for determining whether a given data point from a subject differs from a point, comprising the steps of reading the information through use of a computer program which identifies differences between the test subject's information and the reference information with the computer program.

EXAMPLES

Example 1

APOBEC3G/CEM15/hA3G mRNA Levels Associates Inversely with HIV Viremia

PBMCs were obtained from consenting human subjects and cryopreserved. Prior to RNA isolation, cyropreserved PBMCs were thawed, washed with PBS, and stimulated with 1 µg each of anti-CD3 and anti-CD28 antibodies for 18-20 hours. 2-5×10$^6$ cells were resuspended in 1 ml of TriReagent (MRC), and total cellular RNA isolated according to standard protocols. PolyA+ RNA was isolated using the MicroPoly (A) Purist kit (Ambion) stored in RNase-free water (Ambion) at −80° C. Purified polyA+ RNA was quantified by OD 260 and 280, and all RNAs were found to have a 260/280 ratio of 1.95 or greater. hA3G gene expression was examined by using Taqman chemistry with probes and primers designed to uniquely amplify hA3G/APOBECEG (NM_0218220). The primers used were (FWD: 5' CGCAGCCTGTGTCA-GAAAAG3' (SEQ ID NO: 1, nucleotides 637-657), RVSE: 5' CCAACAGTGCTGAAATTCGTCATA3' (SEQ ID NO: 2, nucleotide 714-691) and Probe: FAM-5' GTGCCACCAT-GAAGA3'-BHQ1 (SEQ ID NO: 3, nucleotide 668-682). The following dye combinations for probe generation were used for detection and data normalization: FAM (for the genes of interest), HEX (for normalize genes, see below) and BHQ1 (non-fluorescent quencher) and ROX. Validation experiments were performed to determine the specificity and efficiency of the primers and probes designed to selectively amplify hA3G mRNA over closely related APOBEC3B (hA3B) and APOBEC3F (hA3F) (Wedekind et al 2003). A commercially available primer/probe combination was used to quantify GAPDH as a normalizing control sequence for the number of cell equivalents in polyA+ mRNA starting material used for the quantification of hA3G mRNA. Following probe and primer optimization, all reverse transcriptase, first strand cDNA products were diluted and used in a 10 µl PCR reaction containing: 5 µl of ABI 2× Universal Master Mix, 1.25 µl of each forward and reverse primers (final stock concentrations ranging from 200-900 nM depending on the primer set), 1 µl of probe (stock ranging from 50-200 nM) and RNase/DNase free water. All reactions were run in an ABI 7900 with 1 cycle of 50° C. (2 min) followed by 95° C. (10 min.) and 40 cycles of 95° C. (15 sec) followed by 60° C. (1 min). Data were collected and analyzed using Sequence Detection Software (ABI, Foster City Calif.), relative quantitation determined using the comparative threshold cycle (CT) method performed in Microsoft Excel (ABI Technote #2: Relative Gene Expression Quantitation).

Figure 7:
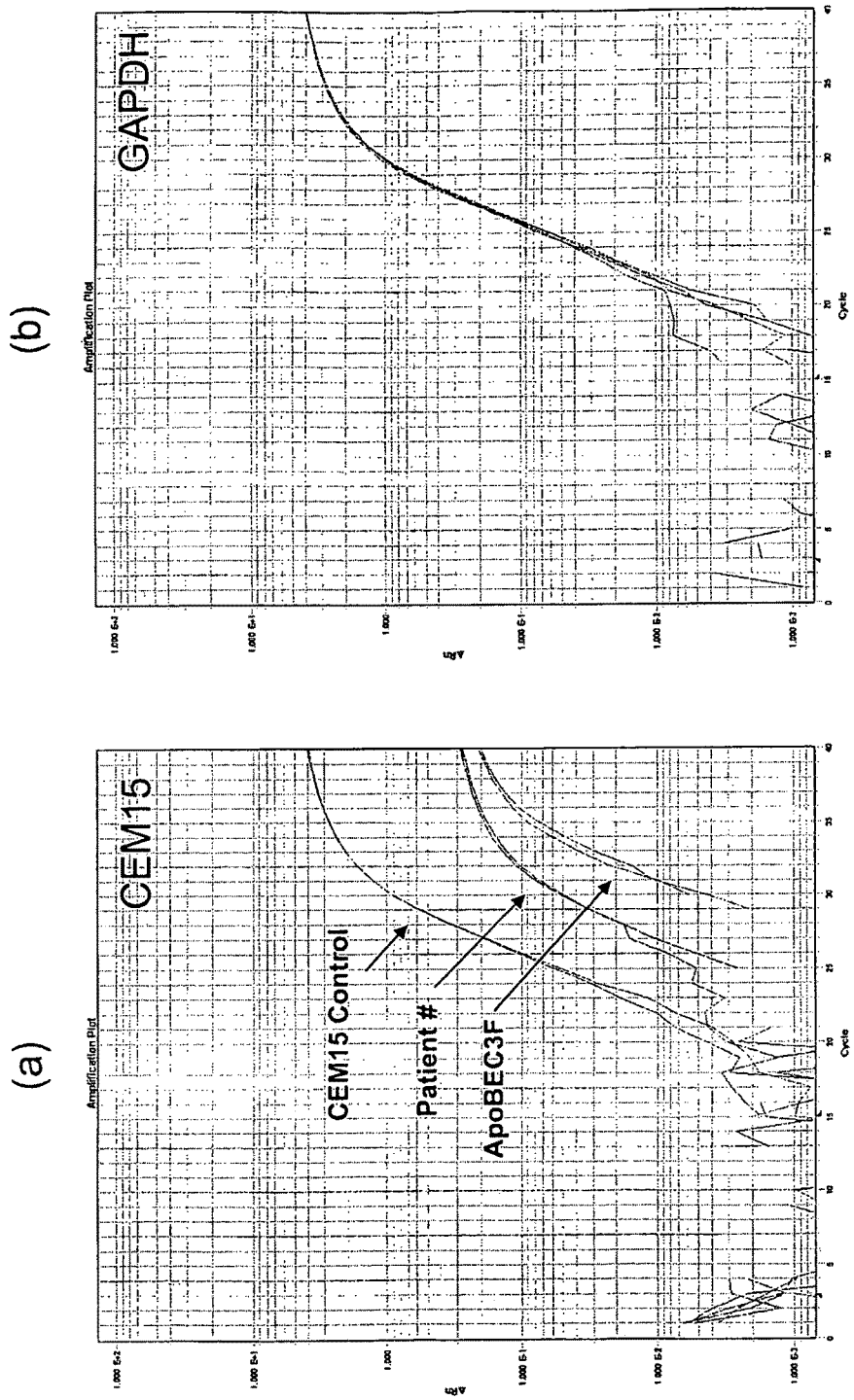
FIG. 7 shows real-time PCR assay for CEM15 gene expression. Samples of polyA+ mRNA were amplified from a positive control (CEM15 plasmid patient samples (patient #7 is shown) and internal control of GAPDH (inset) from reverse transcribed cDNA using the real-time PCR as described in Example 1. Results showed linear amplification of CEM15 and GAPDH mRNAs from human PBMC. Using this assay, CEM15 and GAPDH mRNAs were quantified in each patient sample (Table 3).

FIG. 7 is an example of this assay. Real-time PCR assays were performed using samples from a subject with HIV infection, a positive control (CEM15 control, a plasmid encoding hA3G cDNA) and a negative control (APOBEC3F, a plasmid encoding hA3F cDNA) (FIG. 7a); and GAPDH from the human sample in a separate reaction (FIG. 7b) as a control for cell number that were used to normalize the hA3G quantification. Each sample was tested in duplicates. These results indicated that hA3G quantification was within the reliable detection limits of the assay. Importantly, GAPDH mRNA was expressed at a similar level in each patient sample (FIG. 7b).

Using this method, six HIV-uninfected and twenty-five antiretroviral naïve, chronically HIV-infected subjects, including eight LTNPs whose average viral load was 18×10$^3$ (±1.1×10$^3$) copies/ml, and whose average CD4 count was 755 (±284)/µl; and seventeen progressors whose average viral load was 1.5×10$^3$ (±2.5×10$^5$) copies/ml, and whose average CD4 count was 324 (±208)/µl were studied (Table 3). HIV-1 RNA levels were quantified using the Amplicor HIV-1 Monitor assay (Roche Molecular Systems, Branchburg, N.J.), which has a detection limit of 50 HIV-1 RNA copies/ml. The CD4 counts and percentages were determined using whole blood and the MultiSet program (Becton Dickinson, San Jose, Calif.) by flow cytometer techniques in a CLIA certified laboratory. PBMCs from these subjects were stimulated and samples were coded and sent to another lab for polyA+ mRNA extraction. The samples were recoded and sent for cDNA synthesis and real-time PCR assays. The amounts of hA3G mRNA were standardized against the GAPDH levels in each sample, and calculated as copies of mRNA/µg cDNA. The hA3G mRNA levels in each subject were determined, and the average values (standard deviation) in HIV-uninfected subjects were 132 (±23) copies/µg cDNA, 189 (±59) in LTNPs, and 105 (±15) in progressors. In all HIV-infected subjects, it was 132 (±53) (Table 3). By the Mann-Whitney test, the hA3G mRNA levels in LTNPs are significantly higher than that in progressors (p≤0.001) and HIV-uninfected controls (p≤0.020). In addition, the hA3G levels in HIV-uninfected controls is also higher than that in progressors (p≤0.008).

Figure 8:
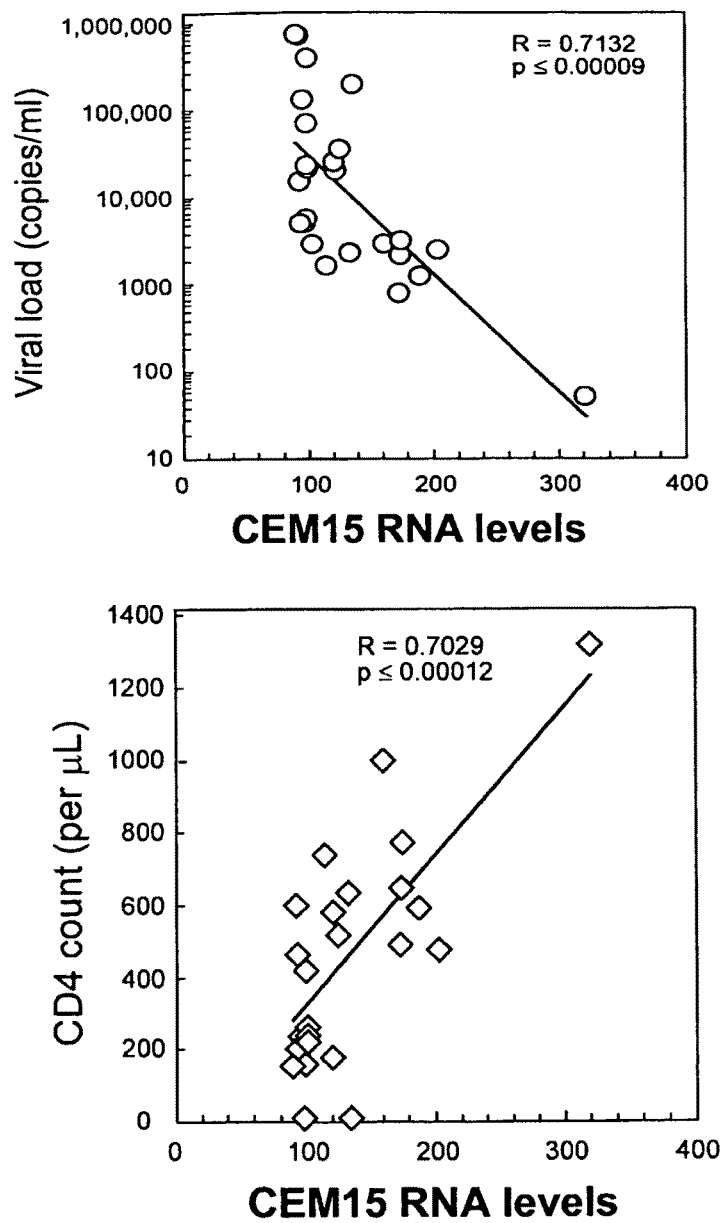
FIG. 8 shows the protective effects of increased CEM15 gene expression. Single linear regression analysis between GAPDH normalized CEM15 mRNA levels and HIV viremia or CD4 counts in eight HIV-infected individuals. Results showed a strong inversed correlation between CEM15 gene expression and viremia levels (a), and a significant positive correlation between CEM15 gene expression and CD4 counts (b).

To determine if the augmented hA3G gene expression had any functional implications, Rank Correlation Test between hA3G mRNA levels and HIV viremia and CD4 counts in the twenty-five HIV-infected individuals was performed. There was a striking inverse correlation between hA3G mRNA levels and viral loads (R=−0.7132, p≤0.00009) (FIG. 8a) and a highly significant positive correlation between hA3G mRNA levels and CD4 counts (R=0.7029, p≤0.00012) (FIG. 8b). Moreover, these correlations remain even after removing the one LTNP (#1) who has the highest CEM15 value (R=−0.5988, p≤0.0022 for viral load, and R=0.4962, p≤0.014 for CD4 count).

TABLE 3

CEM15 mRNA levels in HIV-infected and -uninfected study subjects

| Subject group or patient no. | Viremia (copies/ml) | CD4 count/µl | Yr of HIV infection | CEM15 mRNA copies/µg of cDNA |
|---|---|---|---|---|
| HIV-uninfected[a] | | | | |
| Mean | | | | 132 |
| SD | | | | 23 |
| HIV-infected | | | | |
| LTNPs | | | | |
| 1 | 5.0E±01 | 1,320 | 8 | 321 |
| 2 | 8.1E±02 | 492 | 18 | 173 |
| 3 | 1.3E±03 | 591 | 9 | 189 |
| 4 | 1.7E±03 | 737 | 12 | 114 |
| 5 | 2.2E±03 | 648 | 16 | 175 |
| 6 | 2.6E±03 | 478 | 15 | 204 |
| 7 | 3.0E±03 | 1,000 | 18 | 161 |
| 8 | 3.1E±03 | 775 | 14 | 176 |
| Mean | 1.8E±03 | 755 | | 189 |
| SD | 1.1E±03 | 284 | | 59 |
| Progressors | | | | |
| 9 | 2.4E±03 | 637 | 2 | 133 |
| 10 | 3.0E±03 | 237 | 19 | 103 |
| 11 | 5.3E±03 | 247 | 12 | 98 |
| 12 | 5.3E±03 | 600 | 4 | 93 |
| 13 | 5.8E±03 | 418 | NA[b] | 99 |
| 14 | 1.6E±04 | 462 | 1 | 93 |
| 15 | 2.1E±04 | 582 | 3 | 121 |

TABLE 3-continued

CEM15 mRNA levels in HIV-infected and -uninfected study subjects

| Subject group or patient no. | Viremia (copies/ml) | CD4 count/μl | Yr of HIV infection | CEM15 mRNA copies/μg of cDNA |
|---|---|---|---|---|
| 16 | 2.3E+04 | 263 | 17 | 100 |
| 17 | 2.4E+04 | 166 | NA | 98 |
| 18 | 2.7E+04 | 177 | 6 | 120 |
| 19 | 3.7E+04 | 516 | 3 | 125 |
| 20 | 7.3E+04 | 209 | NA | 98 |
| 21 | 1.4E+05 | 599 | 10 | 94 |
| 22 | 2.1E+05 | 17 | 7 | 135 |
| 23 | 4.1E+05 | 11 | 11 | 98 |
| 24 | 7.5E+05 | 211 | 12 | 92 |
| 25 | 7.5E+05 | 157 | 10 | 89 |
| Mean | 1.5E+05 | 324 | | 105 |
| SD | 2.5E+05 | 208 | | 15 |
| LTNPs + progressors | | | | |
| Mean | 1.0E+05 | 462 | | 132 |
| SD | 2.2E+05 | 307 | | 53 |

[a] n = 6.
[b] NA, not available.

Although it has been shown that hA3G contributes to the control of HIV and SIV replication in cell cultures and animal experiments (Mariani 2003; Sheehy 2002), these results are the first to demonstrate correlations between hA3G mRNA levels and HIV viral load and CD4 count, both of which are predictors of HIV disease progression in patients who have not received antiretroviral drugs or other forms of therapeutic intervention. In addition, as disclosed herein, LTNPs have significantly higher hA3G mRNA levels than did HIV-uninfected controls and the progressors, whose hA3G mRNA levels are significantly lower that of HIV-uninfected controls.

REFERENCES

Alberts, B., D. Bray, J. Lewis, M. Raff, K. Roberts and J. D. Watson Molecular Biology of the Cell. (3rd ed.) Garland Pub. Inc. NY, N.Y. (1994).

An, P., G. Bleiber, P. Duggal, G. Nelson, M. May, B. Mangeat, I. Alobwede, D. Trono, D. Vlahov, S. Donfield, J. J. Goedert, J. Phair, S. Buchbinder, S. J. O'Brien, A. Telenti, and C. A. Winkler: 2004. APOBEC3G genetic variants and their influence on the progression to AIDS. J Virol 78:11070-6.

Anant, S, and N. O. Davidson, Molecular mechanisms of apolipoprotein B mRNA editing. Curr Opin Lipidol. 12(2): 159-65 (2001).

Anant, S. G., Giannoni, F., Antic, D., DeMaria, C. T., Keene, J. D., Brewer, G. and Davidson, N. O. AU-rich RNA binding proteins Hel-N1 and AUF1 bind apolipoprotein B mRNA and inhibit posttranscriptional C to U editing. Nucleic Acids Symp. Ser. 36, 115-118 (1997).

Anant, S., et al., ARCD-1, an apobec-1-related cytidine deaminase, exerts a dominant negative effect on C to U RNA editing. Am J Physiol Cell Physiol. 281:C1904-16 (2001).

Anant, S., et al., Evolutionary origins of the mammalian apolipoproteinB RNA editing enzyme, apobec-1: structural homology inferred from analysis of a cloned chicken small intestinal cytidine deaminase. Biol Chem. 379:1075-81 (1998).

Anant, S., MacGinnitie, A. J. and Davidson, N. O. APOBEC-1, the catalytic subunit of the mammalian apoB B mRNA editing enzyme, is a novel RNA-binding protein. J. Biol. Chem. 270, 14762-14767 (1995).

Andersson, T., C. Furebring, C. A. Borrebaeck and S. Pettersson, Temporal expression of a V(H) promoter-Cmu transgene linked to the IgH HS1,2 enhancer. Mol Immunol, 36(1):19-29 (1999).

Arakawa, H., J. Hauschild and J. M. Buerstedde, Requirement of the activation-induced deaminase (AID) gene for immunoglobulin gene conversion. Science, 295(5558): p. 1301-6 (2002).

Arulampalam, V., C. Furebring, A. Samuelsson, U. Lendahl, C. Borrebaeck, I. Lundkvist and S. Pettersson, Elevated expression levels of an Ig transgene in mice links the IgH 3' enhancer to the regulation of IgH expression. Int Immunol. 8(7):1149-57 (1996).

Baba, T. W., V. Liska, R. Hofmann-Lehmann, J. Vlasak, W. Xu, S. Ayehunie, L. A. Cavacini, M. R. Posner, H. Katinger, G. Stiegler, B. J. Bernacky, T. A. Rizvi, R. Schmidt, L. R. Hill, M. E. Keeling, Y. Lu, J. E. Wright, T. C. Chou, and R. M. Ruprecht. 2000. Human neutralizing monoclonal antibodies of the IgG1 subtype protect against mucosal simian-human immunodeficiency virus infection. Nat Med 6:200-6.

Backus, J. W. and Smith, H. C. Apolipoprotein B mRNA sequences 3' of the editing site are necessary and sufficient for editing and editosome assembly. Nucleic Acids Res. 19(24):6781-6786 (1991).

Backus, J. W. and Smith, H. C. Specific 3' sequences flanking a minimal apoB mRNA editing 'cassette' are critical for efficient editing in vitro. Biochim. Biophys. Acta 1217, 65-73 (1994).

Backus, J. W. and Smith, H. C. Three distinct RNA sequence elements are required for efficient apoB RNA editing in vitro. Nucleic Acids Res. 22, 6007-6014 (1992).

Backus, J. W., Schock, D. and Smith, H. C. Only cytidines 5' of the apoB mRNA mooring sequence are edited. Biochim. Biophys. Acta 1219(1):1-14 (1994).

Barat, C., V. Lullien, O, Schatz, G. Keith, M. T. Nugeyre, F. Gruninger-Leitch, F. Barre-Sinoussi, S. F. LeGrice, and J. L. Darlix, HIV-1 reverse trarscriptase specifically interacts with the anticodon domain of its cognate primer tRNA. Embo J. 8(11):3279-85 (1989).

Baum, C. L., Teng, B. B. and Davidson, N. O. Apolipoprotein B messenger RNA editing in the rat liver: modulation by fasting and refeeding a high carbohydrate diet. J. Biol. Chem. 265, 19263-19270 (1990).

Berkhout, B., A. T. Das, and N. Beerens, HIV-1 RNA editing, hypermutation, and error-prone reverse transcription. Science 292(5514):7 (2001).

Bernstein, E., A. M. Denli and G. J. Hannon, The rest is silence. RNA 7(11):1509-21 (2001).

Betts L., Xiang S, Short S A, Wolfenden R, Carter C W Cytidine deaminase. The 2.3 A crystal structure of an enzyme: transition-state analog complex. J Mol Biol. 235, 635-56 (1994).

Bishop, K. N., R. K. Holmes, A. M. Sheehy, N. O. Davidson, S. J. Cho, and M. H. Malim. 2004. Cytidine deamination of retroviral DNA by diverse APOBEC proteins. Curr Biol 14:1392-6.

Blanc, V., et al. Mutagenesis of apobec-1 complementation factor reveals distinct domains that modulate RNA binding, protein-protein interaction with apobec-1, and complementation of C to U RNA-editing activity. J Biol Chem. 276(49):46386-93 (2001).

Blanc. V., Navaratnam, N., Henderson, J. O., Anant, S., Kennedy, S., Jarmuz, A., Scott, J. and Davidson, N. O. Identification of GRY-RBP as an apo B mRNA binding protein that interacts with both apobec-1 and with apobec-1 complementation factor (ACF) to modulate C to U editing. J. Biol. Chem. 276(13):10272-10283 (2001).

Bogerd, H. P., B. P. Doehle, H. L. Wiegand, and B. R Cullen. 2004. A single amino acid difference in the host APOBEC3G protein controls the primate species specificity of HIV type 1 virion infectivity factor. Proc Natl Acad Sci USA 101:3770-4.

Borman, A. M., C. Quillent, P. Charneau, K. M. Kean, and F. Clavel. 1995. A highly defective HIV-1 group O provirus: evidence for the role of local sequence determinants in G→A hypermutation during negative-strand viral DNA synthesis. Virology 208:601-9.

Borrow, P., H. Lewicki, B. H. Hahn, G. M. Shaw, and M. B. Oldstone. 1994. Virus-specific CD8+ cytotoxic T-lymphocyte activity associated with control of viremia in primary human immunodeficiency virus type I infection. Journal of Virology 68:6103-10.

Borrow, P., H. Lewicki, X. Wei, M. S. Horwitz, N. Peffer, H. Meyers, J. A. Nelson, J. E. Gairin, B. H. Hahn, M. B. Oldstone, and G. M. Shaw. 1997. Antiviral pressure exerted by HIV-1-specific cytotoxic T lymphocytes (CTLs) during primary infection demonstrated by rapid selection of CTL escape virus. Nature Medicine 3:205-11.

Bostrom, K., Garcia, Z., Poksay, K. S., Johnson, D. F., Lusis, A. J. and Innerarity, T. L. Apolipoprotein B mRNA editing. Direct determination of the edited base and occurrence in non-apolipoprotein B producing cell lines. J. Biol. Chem. 265, 22446-22452 (1990).

Bouhamdan, M., S. Benichou, F. Rey, J. M. Navarro, I. Agostini, B. Spire, J. Camonis, G. Slupphaug, R. Vigne, R. Benarous, and J. Sire, Human immunodeficiency virus type 1 Vpr protein binds to the uracil DNA glycosylase DNA repair enzyme. J. Virol. 70(2):697-704 (1996).

Bourara, K., S. Litvak, and A. Araya, Generation of G-to-A and C-to-U changes in HIV-1 transcripts by RNA editing. Science. 289(5484):1564-6 (2000).

Bowie, J. U., R. Luthy, and D. Eisenberg, A method to identify protein sequences that fold into a known three-dimensional structure. Science. 253(5016):164-70 (1991).

Bransteitter, R., P. Pham, M. D. Scharff, and M. F. Goodman, Activation-induced cytidine deaminase deaminates deoxycytidine on single-stranded DNA but requires the action of RNase. Proc Natl Acad Sci USA. 100(7): p. 4102-7 (2003).

Bross, L., M. Muramatsu, K. Kinoshita, T. Honjo and H. Jacobs, DNA Double-Strand Breaks: Prior to but not Sufficient in Targeting Hypermutation. J Exp Med 195(9): 1187-1192 (2002).

Buchbinder, S., and Vittinghoff, E. 1999. HIV-infected long-term nonprogressors: epidemiology, mechanisms of delayed progression, and clinical and research implications. Microbes and Infection 1:1113-1120.

Burley, S. K. An overview of structural genomics. Nature Struct. Biol. 7, 932-934 (2000).

Camaur, D. and D. Trono, Characterization of human immunodeficiency virus type 1 Vif particle Liu, H., X. Wu, M. Newman, G. M. Shaw, B. H. Hahn, and J. C. Kappes, The Vif protein of human and simian immunodeficiency viruses is packaged into virions and associates with viral core structures. J Virol, 69(12): p. 7630-8 incorporation. J. Virol. 70(9):6106-11 (1996).

Cao, Y., L. Qin, L. Zhang, J. Safrit, and D. D. Ho. 1995. Virologic and immunologic characterization of long-term survivors of human immunodeficiency virus type 1 infection. N Engl J Med 332:201-8.

Cao, Y., L. Qin, L. Zhang, J. Safrit, and D. D. Ho. 1995. Virologic and immunologic characterization of long-term survivors of human immunodeficiency virus type 1 infection. N Engl J Med 332:201-8.

Carlow, D. C., A. A. Smith, C. C. Yang, S. A. Short, and R. Wolfenden, Major contribution of a carboxymethyl group to transition-state stabilization by cytidine deaminase: mutation and rescue. Biochemistry. 34(13):4220-4 (1995).

Carrington, M., G. W. Nelson, M. P. Martin, T. Kissner, D. Vlahov, J. J. Goedert, R. Kaslow, S. Buchbinder, K. Hoots, and S. J. O'Brien. 1999. HLA and HIV-1: heterozygote advantage and B*35-Cw*04 disadvantage. Science 283: 1748-52.

Cartegni, L., S. L. Chew and A. R. Krainer, Listening to silence and understanding nonsense: exonic mutations that affect splicing. Nat Rev Genet. 3(4):285-98 (2002).

Casellas, R., A. Nussenzweig, R. Wuerffel, R. Pelanda, A. Reichlin, H. Suh, X. F. Qin, E. Besmer, A. Kenter, K. Rajewsky and M. C. Nussenzweig, Ku80 is required for immunoglobulin isotype switching. Embo J 17(8):2404-11 (1998).

Cattaneo, R. Biased (A→I) hypermutation of animal RNA virus genomes. Curr Opin Genet Dev 4(6): 895-900 (1994).

Chaudhuri, J., M. Tian, C. Khuong, K. Chua, E. Pinaud, and F. W. Alt, Transcription-targeted DNA deamination by the AID antibody diversification enzyme. Nature. 422(6933): 726-30 (2003).

Chen, J., R. Lansford, V. Stewart, F. Young and F. W. Alt, RAG-2-deficient blastocyst complementation: an assay of gene function in lymphocyte development. Proc Natl Acad Sci USA. 90(10): 4528-32 (1993).

Chen, R., H. Wang, and L. M. Mansky, Roles of uracil-DNA glycosylase and dUTPase in virus replication. J Gen Virol. 83(Pt 10):2339-45 (2002).

Chen, S. H., Habib, G., Yang, C. Y., Gu, Z. W., Lee, B. R., Weng, S. A., Silberman, S. R., Cai, S. J., Deslypere, J. P., Rosseneu, M., Gotto, A. M. J. R., Li, W. H. and Chan, L. Apolipoprotein B-48 is the product of a messenger RNA with an organ-specific in-frame stop codon. Science 238, 363-366 (1987).

Chothia, C. and A. M. Lesk, The relation between the divergence of sequence and structure in proteins. Embo J. 5(4): 823-6 (1986).

Chua, K. F., F. W. Alt and J. P. Manis, The Function of AID in Somatic Mutation and Class Switch Recombination Upstream or Downstream of DNA Breaks. J Exp Med 195(9): F37-41 (2002).

Clerici, M., N. I. Stocks, R. A. Zajac, R. N. Boswell, D. R. Lucey, C. S. Via, and G. M. Shearer. 1989. Detection of three distinct patterns of T helper cell dysfunction in asymptomatic, human immunodeficiency virus-seropositive patients. Independence of CD4+ cell numbers and clinical staging. The Journal of Clinical Investigation 84:1892-9.

Courcoul, M., C. Patience, F. Rey, D. Blanc, A. Harmiache, J. Sire, R. Vigne, and B. Spire, Peripheral blood mononuclear cells produce normal amounts of defective Vif-human immunodeficiency virus type 1 particles which are restricted for the preretrotranscription steps. J. Virol. 69(4): 2068-74 (1995).

Dance, G. S. C., Sowden, M. P., Yang, Y. and Smith, H. C. APOBEC-1 dependent cytidine to uridine editing of apolipoprotein B RNA in yeast. Nucleic Acids Res. 28, 424-429 (2000).

Dance, G. S. C., Beemiller, P., Yang, Y., Van Mater, D. Mian, S. I. and Smith, H. C. Identification of the yeast cytidine deaminase CDD1 as an orphan C to U RNA editase. Nucleic Acids Res. 29, 1772-1780 (2001).

Dance, G. S. C., Sowden, M. P., Cartegni, L., Cooper, E., Krainer, A. R., Smith, H. C., Two proteins essential for apolipoprotein B mRNA editing are expressed from a single gene through alternative splicing. J. Biol. Chem., 277:12703-09 (2002).

Davidson, N. O., Powell, L. M., Wallis, S. C. and Scott, J. Thyroid hormone modulates the introduction of a stop codon in rat liver apolipoprotein B messenger RNA. J. Biol. Chem. 263, 13482-13485 (1988)

Deacon, N. J., A. Tsykin, A. Solomon, K. Smith, M. Ludford-Menting, D. J. Hooker, D. A. McPhee, A. L. Greenway, A. Ellett, C. Chatfield, and et al. 1995. Genomic structure of an attenuated quasi species of HIV-1 from a blood transfusion donor and recipients. Science 270:988-91.

Dettenhofer, M., S. Cen, B. A. Carlson, L. Kleiman, and X. F. Yu, Association of human immunodeficiency virus type 1 Vif with RNA and its role in reverse transcription. J Virol, 74(19):893845 (2000).

Doi, T., K. Kinoshita, M. Ikegawa, M. Muramatsu, and T. Honjo, Inaugural Article: De novo protein synthesis is required for the activation-induced cytidine deaminase function in class-switch recombination. Proc Natl Acad Sci USA 100(5):2634-8 (2003).

Driscoll, D. M., Lakhe-Reddy, S., Oleksa, L. M. and Martinez, D. Induction of RNA editing at heterologous sites by sequences in apolipoprotein B mRNA. Mol. Cell. Biol. 13, 7288-7294 (1993).

Driscoll, D. M. and E. Casanova, Characterization of the apolipoprotein B mRNA editing activity in enterocyte extracts. J Biol Chem. 265(35):21401-3 (1990).

Economidis, I. V. and T. Pederson, In vitro assembly of a pre-messenger ribonucleoprotein. Proc Natl Acad Sci USA, 80(14):4296-300 (1983).

Egebjerg, J., Kukekov, V. and Heinemann, S. F. Intron sequence directs RNA editing of the glutamate receptor subunit GluR2 coding sequence. Proc. Natl. Acad. Sci. U.S.A. 91, 10270-10274 (1994).

Ehrenstein, M. R. and M. S. Neuberger Deficiency in Msh2 affects the efficiency and local sequence specificity of immunoglobulin class-switch recombination: parallels with somatic hypermutation. Embo J, 18(12): p. 3484-90 (1999).

Eisenberg, D., R. Luthy, and J. U. Bowie, VERIFY3D: assessment of protein models with three-dimensional profiles. Methods Enzymol. 277:396-404 (1997).

Faham, M., S. Baharloo, S. Tomitaka, J. DeYoung and N. B. Freimer, Mismatch repair detection (MRD): high-throughput scanning for DNA variations. Hum Mol Genet. 10(16): 1657-64 (2001).

Fauci, A. S. 1993. Multifactorial nature of human immunodeficiency virus disease: implications for therapy. Science 262:1011-8.

Fisher, A. G., B. Ensoli, L. Ivanoff, M. Chamberlain, S. Petteway, L. Ratner, R. C. Gallo, and F. Wong-Staal, The sor gene of HIV-1 is required for efficient virus transmission in vitro. Science. 237(4817):888-93 (1987).

Fisher, C. L. and Pei, K. P. Modification of a PCR-based site-directed mutagenesis method. BioTechniques 23, 570-574 (1997).

Fugmann, S. D. and Schatz, D. G. Immunology. One AID to unite them all. Science. 295:1244-5 (2002).

Funahashi, T., Giannoni, F., DePaoli, A. M., Skarosi, S. F. and Davidson, N. O. Tissue-specific, developmental and nutritional regulation of the gene encoding the catalytic subunit of the rat apoB mRNA editing enzyme: functional role in the modulation of apoB mRNA editing. J. Lipid Res. 36:414-428 (1995).

Gaddis, N. C., A. M. Sheehy, K. M. Ahmad, C. M. Swanson, K. N. Bishop, B. E. Beer, P. A. Marx, F. Gao, F. Bibollet-Ruche, B. H. Hahn, and M. H. Malim. 2004. Further investigation of simian immunodeficiency virus Vif function in human cells. J Virol 78:12041-6.

Gaddis, N. C., Certova, E., Sheehy, A. M., Henderson, L. E. and Malim, M. H. Comprehensive investigation of the molecular defect in vif-deficient human immunodeficiency virus type 1 virions. J. Virol. 77(10): 5810-5820 (2003).

Gerber, A., H. Grosjean, T. Melcher, and W. Keller Tad1p, a yeast tRNA-specific adenosine deaminase, is related to the mammalian pre-mRNA editing enzymes ADAR1 and ADAR2. Embo J. 17(16):4780-9 (1998).

Gerber, A. P. and Keller, W. RNA editing by base deamination: more enzymes, more targets, new mysteries. TIBS 26:376-384 (2001).

Gerber, A. P. and W. Keller An adenosine deaminase that generates inosine at the wobble position of tRNAs. Science 286(5442):1146-9 (1999).

Giannoni, F., Bonen, D. K., Funaashi, T., Hadjiagapiou, C., Burant, C. F. and Davidson, N. O. Complementation of apolipoprotein B mRNA editing by human liver accompanied by secretion of apolipoprotein B47. J. Biol. Chem. 269:5932-5936 (1994).

Giannoni, F., Chou, S. C., Skarosi, S. F., Verp, M. S., Field, F. J., Coleman, R. A. and Davidson, N. O. Developmental regulation of the catalytic subunit of the apoB mRNA editing enzyme (APOBEC-1) in human small intestine. J. Lipid Res. 36:1664-1675 (1995).

Gott, J. M. and Emeson, R. B. Functions and mechanisms of RNA editing. Annu. Rev. Genet. 34, 499-531 (2000).

Goulder, P. J., R. E. Phillips, R. A. Colbert, S. McAdam, G. Ogg, M. A. Nowak, P. Giangrande, G. Luzzi, B. Morgan, A. Edwards, A. J. McMichael, and S. Rowland-Jones. 1997. Late escape from an immunodominant cytotoxic T-lymphocyte response associated with progression to AIDS. Nat Med 3:212-7.

Goulder, P. J., Y. Tang, S. I. Pelton, and B. D. Walker. 2000. HLA-B57-restricted cytotoxic T-lymphocyte activity in a single infected subject toward two optimal epitopes, one of which is entirely contained within the other. Journal of Virology 74:5291-9.

Greeve, J., Altkemper, I., Dieterich, J-H., Greten, H. and Winder, E. (1993) Apolipoprotein B mRNA editing in 12 different mammalian species: hepatic expression is reflected in low concentrations of apoB-containing plasma lipoproteins. J. Lipid Res. 34:1367-1383 (2000).

Greeve, J., Lellek, H., Rautenberg, P. and Greten, H. Inhibition of the apolipoprotein B mRNA editing enzyme-complex by hnRNP C1 protein and 40S hnRNP complexes. Biol. Chem. 379:1063-1073 (1998).

Grosjean, H. and Benne, R. Modification and Editing of RNA. ASM Press, Washington D.C. (1998)

Hader, S. L., T. W. Hodge, K. A. Buchacz, R. A. Bray, N. S. Padian, A. Rausa, S. A. Slaviniski, and S. D. Holmberg. 2002. Discordance at human leukocyte antigen-DRB3 and protection from human immunodeficiency virus type 1 transmission. J Infect Dis 185:1729-35.

Harris, R. S., Bishop, K. N., Sheehy, A. M., Craig, H. M., Petersen-Mahrt, S. K., Watt, I. N., Neuberger, M. S., and Malim, M. H. DNA deamination mediates innate immunity to retroviral infection. Cell. 113:803-809 (2003).

Harris, R. S., S. K. Petersen-Mahrt, and M. S. Neuberger, RNA editing enzyme APOBEC1 and some of its homologs can act as DNA mutators. Mol Cell. 10(5):1247-53 (2002).

Harris, S. G., Sabio, I., Mayer, E., Steinburg, M. F., Backus, J. W., Sparks, J. D., Sparks, C. E. and Smith, H. C. Extract-specific heterogeneity in high-order complexes containing apolipoprotein B mRNA editing activity and RNA-binding proteins. J. Biol. Chem. 268(10):7382-7392 (1993).

Harris, S. G. and Smith, H. C. In vitro apoB mRNA editing activity can be modulated by fasting and refeeding rats with a high carbohydrate diet. Biochem. Biophys. Res. Commun. 183(2):899-903 (1992).

Hendel, H., S. Caillat-Zucman, H. Lebuanec, M. Carrington, S. O'Brien, J. M. Andrieu, F. Schachter, D. Zagury, J. Rappaport, C. Winkler, G. W. Nelson, and J. F. Zagury. 1999. New class I and II HLA alleles strongly associated with opposite patterns of progression to AIDS. J Immunol 162:6942-6.

Henzler, T., Harmache, A., Herrmann, H., Spring, H., Suzan, M., Audoly, G., Panek, T. and Bosch, V. Fully functional, naturally occurring and C-terminally truncated variant human immunodeficiency virus (HIV) Vif does not bind to HIV Gag but influences intermediate filament structure. J. Gen Virol. 82:561-573 (2001).

Hersberger, M. and Innerarity, T. L. Two efficiency elements flanking the editing site of cytidine 6666 in the apolipoprotein B mRNA support mooring dependent editing. J. Biol. Chem. 273:9435-9442 (1998).

Hersberger, M., Patarroyo-White, S., Arnold, K. S, and Innerarity, T. L. Phylogenetic analysis of the apolipoprotein B mRNA editing region. Evidence for a secondary structure between the mooring sequence and the 3' efficiency element. J. Biol. Chem. 274, 34590-34597 (1999).

Higuchi, M., Maas, S., Single, F. N., Hartner, J., Rozov, A., Burnashev, N., Feldmeyer, D., Sprengel, R. and Seeburg, P. H. Point mutation in an AMPA receptor gene rescues lethality in mice deficient in the RNA editing enzyme ADAR2. Nature (London) 405:78-81 (2000).

Higuchi, M., Single, F. N., Köhler, M., Sommer, B., Sprengel, R. and Seeburg, P. H. RNA editing of AMPA receptor subunit GluR-B: a base-paired intron-exon structure determines position and efficiency. Cell 75:1361-1370 (1993).

Hilleren, P. and R. Parker, mRNA surveillance in eukaryotes: kinetic proofreading of proper translation termination as assessed by mRNP domain organization? RNA. 5(6):711-9 (1999).

Hirano, K. I., Young, S. G., Farese, R. V., Ng, J., Sande, E., Warburton, C., Powell-Braxton, L. M. and Davidson, N. O. Targeted disruption of the mouse apobec-1 gene abolishes apoB mRNA editing and eliminates ApoB48. J. Biol. Chem., 271, 9887-9890 (1996).

Honjo, T., et al. Molecular Mechanism of Class Switch Recombination: Linkage with Somatic Hypermutation. Annu Rev Immunol. 20:165-96 (2002).

Hu, B. T., S. C. Lee, E. Marin, D. H. Ryan and R. A. Insel, Telomerase is up-regulated in human germinal center B cells in vivo and can be re-expressed in memory B cells activated in vitro. J Immunol. 159(3):1068-71 (1997).

Huang, Y., L. Zhang, and D. D. Ho. 1998. Characterization of gag and pol Sequences from Long-Term Survivors of Human Immunodeficiency Virus Type 1 Infection. Virology 240:36.

Hwang, J. T., K. A. Tallman, and M. M. Greenberg, The reactivity of the 2-deoxyribonolactone lesion in single-stranded DNA and its implication in reaction mechanisms of DNA damage and repair. Nucleic Acids Res, 27(19): 3805-10 (1999).

Inui, Y., Giannoni, F., Funahashi, T. and Davidson, N. O. REPR and complementation factor(s) interact to modulate rat apolipoprotein B mRNA editing in response to alterations in cellular cholesterol flux. J. Lipid Res. 35, 1477-1489 (1994).

Janini, M., M. Rogers, D. R. Birx, and F. E. McCutchan. 2001. Human immunodeficiency virus type 1 DNA sequences genetically damaged by hypermutation are often abundant in patient peripheral blood mononuclear cells and may be generated during near-simultaneous infection and activation of CD4(+) T cells. J Virol 75:7973-86.

Jarmuz, A., A. Chester, J. Bayliss, J. Gisbourne, I. Dunham, J. Scott, and N. Navaratnam. 2002. An Anthropoid-Specific Locus of Orphan C to U RNA-Editing Enzymes on Chromosome 22. Genomics 79:285-96.

Jin, X., G. Ogg, S. Bonhoeffer, J. Safrit, M. Vesanen, D. Bauer, D. Chen, Y. Cao, M. A. Demoitie, L. Zhang, M. Markowitz, D. Nixon, A. McMichael, and D. D. Ho. 2000. An antigenic threshold for maintaining human immunodeficiency virus type 1-specific cytotoxic T lymphocytes. Molecular Medicine 6:803-9.

Johansson E, Mejlhede N, Neuhard J, Larsen S. Crystal structure of the tetrameric cytidine deaminase from *Bacillus subtilis* at 2.0 Å resolution. Biochem. 41(8):2563-70 (2002)

Jones, T. A., J. Y. Zou, S. W. Cowan, and Kjeldgaard, Improved methods for building protein models in electron density maps and the location of errors in these models. Acta Crystallogr A. 47 (Pt 2):110-9 (1991).

Kabsch, W., A solution for the best rotation to relate two sets of vectors. Acta. Crystallogr., A32:922-923 (1976).

Kao, S., E. Miyagi, M. A. Khan, H. Takeuchi, S. Opi, R. Goila-Gaur, and K. Strebel. 2004. Production of infectious human immunodeficiency virus type 1 does not require depletion of APOBEC3G from virus-producing cells. Retrovirology 1:27.

Kaslow, R. A., M. Carrington, R. Apple, L. Park, A. Munoz, A. J. Saah, J. J. Goedert, C. Winkler, S. J. O'Brien, C. Rinaldo, R. Detels, W. Blattner, J. Phair, H. Erlich, and D. L. Mann. 1996. Influence of combinations of human major histocompatibility complex genes on the course of HIV-1 infection. Nat Med 2:405-11.

Kataoka, N., Yong, J., Kim, V. N., Velazquez, F., Perkinson, R. A., Wang, F. and Dreyfuss, G. Pre-mRNA splicing imprints mRNA in the nucleus with a novel RNA-binding protein that persists in the cytoplasm. Mol. Cell. 6:673-682 (2000).

Kaul, R., F. A. Plummer, J. Kimani, T. Dong, P. Kiama, T. Rostron, E. Njagi, K. S. MacDonald, J. J. Bwayo, A. J. McMichael, and S. L. Rowland-Jones. 2000. HIV-1-specific mucosal CD8+ lymphocyte responses in the cervix of HIV-1-resistant prostitutes in Nairobi. J Immunol 164:1602-11.

Kaushik, N. and V. N. Pandey, PNA targeting the PBS and A-loop sequences of HIV-1 genome destabilizes packaged tRNA3(Lys) in the virions and inhibits HIV-1 replication. Virology. 303(2):297-308 (2002).

Keegan, L. P., A. P. Gerber, J. Brindle, R. Leemans, A. Gallo, W. Keller, and M. A. O'Connell, The properties of a tRNA-specific adenosine deaminase from *Drosophila melanogaster* support an evolutionary link between pre-mRNA editing and tRNA modification. Mol Cell Biol 20(3):825-33 (2000).

Keegan, L. P., et al. The many roles of an RNA editor. Nat Rev Genet. 2:869-78 (2001).

Keller, W., J. Wolf, and A. Gerber, Editing of messenger RNA precursors and of tRNAs by adenosine to inosine conversion. FEBS Lett, 452(1-2):71-6. (1999).

Khan, M. A., Aberham, C., Kao, S., Akari, H., Gorelick, R., Bour, S, and Strebel, K. Human immunodeficiency virus type 1 Vif protein is packaged into the nucleoprotein complex through an interaction with viral genomic RNA. J. Virol. 75(16):7252-7265 (2001).

Kleiman, L., tRNA(Lys3): the primer tRNA for reverse transcription in HIV-1. IUBMB Life 53(2):107-14 (2002).

Kohler, M., Burnashev, N., Sakmann, B. and Seeburg, P. H. Determinants of Ca 2+ permeability in both TM1 and TM2 of high affinity kainate receptor channels: diversity by RNA editing. Neuron 10:491-500 (1993).

Koup, R. A., C. A. Pikora, K. Luzuriaga, D. B. Brettler, E. S. Day, G. P. Mazzara, and J. L. Sullivan. 1991. Limiting dilution analysis of cytotoxic T lymphocytes to human immunodeficiency virus gag antigens in infected persons: in vitro quantitation of effector cell populations with p17 and p24 specificities. The Journal of Experimental Medicine 174:1593-600.

Koup, R. A., J. T. Safrit, Y. Cao, C. A. Andrews, G. McLeod, W. Borkowsky, C. Farthing, and D. D. Ho. 1994. Temporal association of cellular immune responses with the initial control of viremia in primary human immunodeficiency virus type 1 syndrome. Journal of Virology 68:4650-5.

Krogh, A., Brown, M., Mian, I. S., Sjolander, K. and Haussler, D. Hidden Markov models in computational biology. Applications to protein modeling, J Mol Biol. 235:1501-31 (1994).

Kumar, M. and G. G. Carmichael Nuclear antisense RNA induces extensive adenosine modifications and nuclear retention of target transcripts. Proc Natl Acad Sci USA. 94(8):3542-7 (1997).

Kuyper, L. F. and C. W. Carter, Resolving crystal polymorphism by finding 'stationary points' from quantitative analysis of crystal growth response surfaces. J. Crystal Growth. 168:135-169 (1996).

Kuzin, I. I., J. E. Snyder, G. D. Ugine, D. Wu, S. Lee, T. J. Bushnell, R. A. Insel, F. M. Young, Bottaro, A., Tetracyclines inhibit activated B cell function. Int. Immunol. 12:921-931 (2001).

Kuzin, I. I., G. D. Ugine, D. Wu, F. Young, J. Chen and A. Bottaro, Normal isotype switching in B cells lacking the I mu exon splice donor site: evidence for multiple I mu-like germline transcripts. J. Immunol. 164(3):1451-7 (2000).

Lanier, L. L. 1998. NK cell receptors. Annu Rev Immunol 16:359-93.

Lau, P. P., Xiong, W. J., Zhu, H. J., Chen, S. H. and Chan, L. Apolipoprotein B mRNA editing is an intranuclear event that occurs post-transcriptionally coincident with splicing and polyadenylation. J. Biol. Chem. 266:20550-20554 (1991).

Lau, P. P, Chang, B. H. J. and Chan, L. Two-hybrid cloning identifies an RNA-binding protein GRY-RBP, as a component of apobec-1 editosome. Biochem. Biophys. Res. Commun. 282(4):977-983 (2001).

Lau, P. P., Cahill, D. J., Zhu, H. J. and Chan, L. Ethanol modulates apoB mRNA editing. J. Lipid Res. 36:2069-2078 (1995).

Lau, P. P., Villanueva, H., Kobayashi, K., Nakamuta, M., Chang, H. J., Chan, L., A DnaJ protein, Apobec-1-binding protein-2, modulates apolipoprotein B mRNA editing. J. Biol. Chem. 276:46445-46452 (2001).

Lau, P. P., Zhu, H. J., Baldini, A., Charnsangavej, C. and Chan, L. Dimeric structure of a human apolipoprotein B mRNA editing protein and cloning and chromosomal localization of its gene. Proc. Natl. Acad. Sci. USA 91:8522-8526 (1994).

Lau, P. P., Zhu, H. J., Nakamuta, M. and Chan, L. Cloning of an Apobec-1-binding protein that also interacts with apolipoprotein B mRNA and evidence for its involvement in RNA editing. J. Biol. Chem. 272(3):1452-1455 (1997).

Le Hir, H., Izaurralde, E., Maquat, L. E. and Moore, M. J. (2000) The spliceosome deposits multiple proteins 20-24 nucleotides upstream of mRNA exon-exon junctions. EMBO J. 19, 6860-6869.

Lecossier, D., Bouchonnet, F., Clavel, F. and Hance, A. J. (2003) Science 300: 1112.

Lee, R. M., et al., (1998) An alternatively spliced form of apobec-1 messenger RNA is overexpressed in human colon cancer. Gastroenterology. 115:1096-103.

Lellek, H., Kirsten, R., Diehl, I., Apostel, F., Buck, F. and Greeve, J. (2000) Purification and Molecular cloning of a novel essential component of the apolipoprotein B mRNA editing Enzyme-complex. J. Biol. Chem., 275, 19848-19856.

Lesk, A. M. and C. Chothia, How different amino acid sequences determine similar protein structures: the structure and evolutionary dynamics of the globins. J Mol Biol 136(3):225-70 (1980).

Lewis, J. D. and Tollervey, D. (2000) Like attracts like: getting RNA processing together in the nucleus. Science 288, 1385-1389.

Liao, W., Hong, S. H., Chan, B. H. J., Rudolph, F. B., Clark, S. C. and Chan, L. (1999) APOBEC-2, a cardiac- and skeletal muscle-specific member of the cytidine deaminase supergene family. Biochem. Biophys. Res. Commun. 260, 398-404.

Liddament, M. T., W. L. Brown, A. J. Schumacher, and R. S. Harris. 2004. APOBEC3F properties and hypermutation preferences indicate activity against HIV-1 in vivo. Curr Biol 14:1385-91.

Liu, B., X. Yu, K. Luo, Y. Yu, and X. F. Yu. 2004. Influence of primate lentiviral Vif and proteasome inhibitors on human immunodeficiency virus type 1 virion packaging of APOBEC3G. J Virol 78:2072-81.

Liu, H., X. Wu, M. Newman, G. M. Shaw, B. H. Hahn, and J. C. Kappes, The Vif protein of human and simian immunodeficiency viruses is packaged into virions and associates with viral core structures. J. Virol. 69(12):7630-8 (1995).

Liu, H. X., L. Cartegni, M. Q. Zhang and A. R. Krainer, A mechanism for exon skipping caused by nonsense or missense mutations in BRCA1 and other genes. Nat Genet, 27(1):55-8 (2001).

Liu, H. X., M. Zhang and A. R. Krainer, Identification of functional exonic splicing enhancer motifs recognized by individual SR proteins. Genes Dev, 12(13):1998-2012 (1998).

Liu, Y. and C. E. Samuel, Mechanism of interferon action: functionally distinct RNA-binding and catalytic domains in the interferon-inducible, double-stranded RNA-specific adenosine deaminase. J. Virol. 70(3):1961-8 (1996).

Liu, Y., R. B. Emeson, and C. E. Samuel, Serotonin-2C receptor pre-mRNA editing in rat brain and in vitro by splice site variants of the interferon-inducible double-stranded RNA-specific adenosine deaminase ADAR1. J Biol Chem. 274 (26):8351-8 (1999).

Long, E. O. 1999. Regulation of immune responses through inhibitory receptors. Annu Rev Immunol 17:875-904.

Longacre, A. and U. Storb, A novel cytidine deaminase affects antibody diversity. Cell 102(5): 541-4 (2000).

Lum, J. J., O. J. Cohen, Z. Nie, J. G. Weaver, T. S. Gomez, X. J. Yao, D. Lynch, A. A. Pilon, N. Hawley, J. E. Kim, Z. Chen, M. Montpetit, J. Sanchez-Dardon, E. A. Cohen, and A. D. Badley. 2003. Vpr R77Q is associated with long-term nonprogressive HIV infection and impaired induction of apoptosis. J Clin Invest 111:1547-54.

Maas, S. and Rich, A. (2000) Changing genetic information through RNA editing. BioEssays 22, 790-802.

Maas, S., Melcher, T. and Seeburg, P. H. (1997) Mammalian RNA-dependent deaminases and edited mRNAs. Curr. Opin: Cell. Biol. 9, 343-349.

Maas, S., Melcher, T., Herb, A., Seeburg, P. H., Keller, W., Krause, S., Higuchi, M. and O'Connell, M. A. (1996). Structural requirements for RNA editing in glutamate receptor pre-mRNA by recombinant double-stranded RNA adenosine deaminase. J. Biol. Chem. 271, 12221-12226.

MacGinnitie, A. J., Anant, S, and Davidson, N. O. (1995) Mutagenesis of APOBEC-1, the catalytic subunit of the mammalian apolipoprotein B mRNA editing enzyme, reveals distinct domains that mediate cytosine nucleoside deaminase, RNA-binding, and RNA editing activity. J. Biol. Chem. 270, 14768-14775.

Madani, N. and D. Kabat, An endogenous inhibitor of human immunodeficiency virus in human lymphocytes is overcome by the viral Vif protein. J. Virol. 72(12):10251-5 (1998).

Madsen P., Anant S., Rasmussen, H. H., Gromov, P., Vorum, H., Dumanski, J. P., Tommerup, N., Collins, J. E., Wright, C. L., Dunham, I., MacGinnitie, A. J., Davidson, N. O. and Celis, J. E. Psoriasis upregulated phorbolin-1 shares structural but not functional similarity to the mRNA-editing protein apobec-1. J. Invest. Dermatol. 113(2):162-169 (1999).

Mangeat, B., P. Turelli, G. Caron, M. Friedli, L. Perrin, and D. Trono. 2003. Broad antiretroviral defence by human APOBEC3G through lethal editing of nascent reverse transcripts. Nature 424:99-103.

Mangeat, B., P. Turelli, S. Liao, and D. Trono. 2004. A single amino acid determinant governs the species-specific sensitivity of APOBEC3G to Vif action. J Biol Chem 279: 14481-3.

Manis, J. P., Y. Gu, R. Lansford, E. Sonoda, R. Ferrini, L. Davidson, K. Rajewsky and F. W. Alt, Ku70 is required for late B cell development and immunoglobulin heavy chain class switching. J Exp Med. 187(12):2081-9 (1998).

Mansky, L. M., S. Preveral, L. Selig, R. Benarous, and S. Benichou, The interaction of vpr with uracil DNA glycosylase modulates the human immunodeficiency virus type 1 in vivo mutation rate. 74(15):7039-47 (2000).

Maquat, L. and Carmichael, G. G. Quality control of mRNA function. Cell 104(2):173-176 (2001).

Mariani, R., D. Chen, B. Schrofelbauer, F. Navarro, R. Konig, B. Bollman, C. Munk, H. Nymark-McMahon, and N. R. Landau. 2003. Species-specific exclusion of APOBEC3G from HIV-1 virions by Vif. Cell 114:21-31.

Marinettii, G. V., Disorders of Lipid Metabolism. New York: Plenum Press (1990).

Martin, A. and M. D. Scharff, AID and mismatch repair in antibody diversification. Nat Rev Immunol. 2(8):605-14 (2002).

Martin, A., P. D. Bardwell, C. J. Woo, M. Fan, M. J. Shulman and M. D. Scharff, Activation-induced cytidine deaminase turns on somatic hypermutation in hybridomas. Nature. 415(6873): 802-6, (2002).

Mascola, J. R., G. Stiegler, T. C. VanCott, H. Katinger, C. B. Carpenter, C. E. Hanson, H. Beary, D. Hayes, S. S. Frankel, D. L. Birx, and M. G. Lewis. 2000. Protection of macaques against vaginal transmission of a pathogenic HIV-1/SIV chimeric virus by passive infusion of neutralizing antibodies. Nat Med 6:207-10.

McCahill, A., Lankester, D. J., Park, S., Price, N. T. and Zammit, V. A. (2000) Acute modulation of the extent of apoB mRNA editing and relative rates of synthesis of apoB48 and apoB100 in cultured rat hepatocytes by osmotic and other stresses. Molec. Cell. Biochem. 208, 77-87.

Mehta, A., Driscoll, D. M. Identification of Domains in APOBEC-1 Complementation Factor Required for RNA Binding and Apolipoprotein B mRNA editing. RNA. 8:69-82 (2002).

Mehta, A., Kinter, M. T., Sherman, N. E. and Driscoll, D. M. Molecular cloning of apobec-1 complementation factor, a novel RNA-binding protein involved in the editing of apolipoprotein B mRNA, Mol Cell Biol. 20:1846-54 (2000).

Mian, I. S., Moser, M. J., Holley, W. R. and Chatterjee, A. Statistical modeling and phylogenetic analysis of a deaminase domain, J. Comput. Biol. 5: 57-72 (1998).

Migueles, S. A., A. C. Laborico, H. Imamichi, W. L. Shupert, C. Royce, M. McLaughlin, L. Ehler, J. Metcalf, S. Liu, C. W. Hallahan, and M. Connors. 2003. The differential ability of HLA B*5701+ long-term nonprogressors and progressors to restrict human immunodeficiency virus replication is not caused by loss of recognition of autologous viral gag sequences. Journal of Virology 77:6889-98.

Minegishi, Y., A. Lavoie, et al. (2000). "Mutations in activation-induced cytidine deaminase in patients with hyper IgM syndrome." Clin Immunol 97(3): 203-10.

Morrison, J. R., Paszty, C., Stevens, M. E., Hughes, S. D., Forte, T. and Scott, J. (1996) ApoB RNA editing enzyme-deficient mice are viable despite alterations in lipoprotein metabolism. Proc. Natl. Acad. Sci. USA 93, 7154-7159.

Mukhopadhyay, D., S. Anant, R. M. Lee, S. Kennedy, D. Viskochil and N. O. Davidson, C→U editing of neurofibromatosis.I mRNA occurs in tumors that express both the type II transcript and apobec-1, the catalytic subunit of the apolipoprotein B mRNA-editing enzyme. Am J Hum Genet. 70(1):38-50 (2002).

Muramatsu, M., K. Kinoshita, et al. (2000). "Class switch recombination and hypermutation require activation-induced cytidine deaminase (AID), a potential RNA editing enzyme." Cell 102(5): 553-63.

Muramatsu, M., V. S. Sankaran and, et al. (1999). "Specific expression of activation-induced cytidine deaminase (AID), a novel member of the RNA-editing deaminase family in germinal center B cells." J Biol Chem 274(26): 18470-6.

Muschen, M., K. Rajewsky, M. Kronke and R. Kuppers, The origin of CD95-gene mutations in B-cell lymphoma. Trends Immunol, 2002. 23(2): p. 75-80.

Muto, T., M. Muramatsu, et al. (2000). "Isolation, tissue distribution, and chromosomal localization of the human activation-induced cytidine deaminase (AID) gene." Genomics 68(1): 85-8.

Nagaoka, H., M. Muramatsu, N. Yamamura, K. Kinoshita and T. Honjo, Activation-induced deaminase (AID)-directed hypermutation in the immunoglobulin Smu region: implication of AID involvement in a common step of class switch recombination and somatic hypermutation. J Exp Med, 2002. 195(4): p. 529-34.

Nakamuta, M., Chang, B. H. J., Zsigmond, E., Kobayashi, K., Lei, H., Ishida, B. Y., Oka, K., Li, E. and Chan, L. (1996) Complete phenotypic characterization of apobec-1 knockout mice with a wild-type genetic background and a human apoB transgenic background, and restoration of apoB mRNA editing by somatic gene transfer of APOBEC-1. J. Biol. Chem. 271, 25981-25988.

Navaratnam, N., Bhattacharya, S., Fujino, T., Patel, D., Jarmuz, A. L. and Scott, J. Evolutionary origins of apoB mRNA editing: catalysis by a cytidine deaminase that has acquired a novel RNA-binding motif at its active site. Cell 81, 187-195 (1995).

Navaratnam, N., D., Patel, R. R., Shah, J. C., Greeve L. M., Powell, T. J., Knott, J., Scott, An additional editing site is present in apolipoprotein B mRNA. Nucleic Acids Res., 19:1741-1744 (1991).

Navaratnam, N., Fujino, T., Bayliss, J., Jarmuz, A., How, A. Richardson, N., Somasekaram, A. Bhattacharya, S., Carter, C. & Scott, J. *Escherichia coli* cytidine deaminase provides a molecular model for ApoB RNA editing and a mechanism for RNA substrate recognition JMB 275:695-714 (1998).

Navaratnam, N., R. Shah, D. Patel, V. Fay and J. Scott, Apolipoprotein B mRNA editing is associated with UV crosslinking of proteins to the editing site. Proc Natl Acad Sci USA. 90(1):222-6 (1993).

Neuberger, M. S., Harris, R. S., Di Noia, J., and Petersen-Mahrt, S. K. Immunity through DNA deamination. Trends in Biochemical Sciences. Advanced online publication, in press (2003).

Neumann, J. R., Morency, C. A. and Russian, K. O. A novel rapid assay for chloramphenicol acetyltransferase gene expression. BioTechniques 5: 444-448 (1987).

Nixon, D. F., A. R. Townsend, J. G. Elvin, C. R. Rizza, J. Gallwey, and A. J. McMichael. 1988. HIV-1 gag-specific cytotoxic T lymphocytes defined with recombinant vaccinia virus and synthetic peptides. Nature 336:484-7.

O'Brien, S. J., and J. P. Moore. 2000. The effect of genetic variation in chemokines and their receptors on HIV transmission and progression to AIDS. Immunol Rev 177:99-111.

O'Brien, S. J., X. Gao, and M. Carrington. 2001. HLA and AIDS: a cautionary tale. Trends Mol Med 7:379-81.

O'Connell, M. A. RNA Editing: Rewriting Receptors. Current Biology 7:R437-R439 (1997).

Ohagen, A. and D. Gabuzda, Role of Vif in stability of the human immunodeficiency virus type 1 core. J Virol, 74(23):11055-66 (2000).

Oka, K., Kobayashi, K., Sullivan, M., Martinez, J., Teng, B. B., Ishimura-Oka, K. and Chan, L. Tissue-specific inhibition of apoB B mRNA editing in the liver by adenovirus-mediated transfer of a dominant negative mutant APOBEC-1 leads to increased low density lipoprotein in mice. J. Biol. Chem. 272(3):1456-1460 (1997).

Okazaki, I. M., et al. The AID enzyme induces class switch recombination in fibroblasts. Nature. 416:340-5 (2002).

Paddison, P. J., A. A. Caudy, E. Bernstein, G. J. Hannon and D. S. Conklin, Short hairpin RNAs (shRNAs) induce sequence-specific silencing in mammalian cells. Genes Dev, 2002. 16(8):948-58.

Paddison, P. J., A. A. Caudy and G. J. Hannon, Stable suppression of gene expression by RNAi in mammalian cells. Proc Natl Acad Sci. USA, 2002. 99(3): p. 1443-8.

Pantaleo, G., and R. A. Koup. 2004. Correlates of immune protection in HIV-1 infection: what we know, what we don't know, what we should know. Nat Med 10:806-10.

Pantaleo, G., and R. A. Koup. 2004. Correlates of immune protection in HIV-1 infection: what we know, what we don't know, what we should know. Nat Med 10:806-10.

Pantaleo, G., S. Menzo, M. Vaccarezza, C. Graziosi, O. J. Cohen, J. F. Demarest, D. Montefiori, J. M. Orenstein, C. Fox, and L. K. Schrager. 1995. Studies in subjects with long-term nonprogressive human immunodeficiency virus infection. The New England Journal of Medicine 332:209-16.

Papavasiliou, F. N. and D. G. Schatz Cell-cycle-regulated DNA double-stranded breaks in somatic hypermutation of immunoglobulin genes. Nature 408(6809):216-21 (2000).

Papavasiliou, F. N. and D. G. Schatz The Activation-induced Deaminase Functions in a Postcleavage Step of the Somatic Hypermutation Process. J Exp Med 195(9):1193-1198 (2002).

Petersen-Mahrt, S. K., et al., AID mutates *E. coli* suggesting a DNA deamination mechanism for antibody diversification. Nature 418:99-104 (2002).

Pham, P., Bransteitter, R., Petruska, J. and Goodman, M. F. Processive AID-catalyzed cytosine deamination on single-stranded DNA simulates somatic hypermutation. Nature Advanced online publication, in press.

Phillips, R. E., S. Rowland_Jones, D. F. Nixon, F. M. Gotch, J. P. Edwards, A. O. Ogunlesi, J. G. Elvin, J. A. Rothbard, C. R. Bangham, and C. R. Rizza. 1991. Human immunodeficiency virus genetic variation that can escape cytotoxic T cell recognition. Nature 354:453-9.

Phung, T. L., Sowden, M. P., Sparks, J. D., Sparks, C. E. and Smith, H. C. (1996) Regulation of hepatic apoB RNA editing in the genetically obese Zucker rat. Metabolism 45, 1056-1058.

Polson, A. G., B. L. Bass, and J. L. Casey, RNA editing of hepatitis delta virus antigenome by dsRNA-adenosine deaminase. Nature 380(6573):454-6 (1996).

Potterton, E., S. McNicholas, E. Krissinel, K. Cowtan, and M. Noble, The CCP4 molecular-graphics project. Acta Crystallogr D Biol Crystallogr. 58(Pt 11):1955-7 (2002).

Powell, L. M., Wallis, S. C., Pease, R. J., Edwards, Y. H., Knott, T. J. and Scott, J. (1987) A novel form of tissue-specific RNA processing produces apolipoprotein-B48 in intestine. Cell 50, 831-840.

Puck, J. M., A disease gene for autosomal hyper-IgM syndrome: more genes associated with more immunodeficiencies. Clin Immunol, (2000). 97(3): p. 191-2

Rada, C., et al., (2002) AID-GFP chimeric protein increases hypermutation of Ig genes with no evidence of nuclear localization. Proc. Natl. Acad. Sci. USA. 99:7003-7008

Ramiro, A. R., P. Stavropoulos, M. Jankovic, and M. C. Nussenzweig, Transcription enhances AID-mediated cytidine deamination by exposing single-stranded DNA on the nontemplate strand. Nat Immunol (2003).

Renda, M. J., J. D. Rosenblatt, E. Klimatcheva, L. M. Demeter, R. A. Bambara, and V. Planelles, Mutation of the methylated tRNA(Lys)(3) residue A58 disrupts reverse transcription and inhibits replication of human immunodeficiency virus type 1. J Virol 75(20):9671-8 (2001).

Revy, P, Muto, R., Levy, Y., Geissmann, f., Plebani, A., Sanal, O., Catalan, N., Forveille, M., Dufourcq-Lagelouse, R., Gennery, A., Tezcan, I., Ersoy, F., Kayserili, H., Ugazio, A. G., Brousse, N., Muramatsu, M., Notarangelo, L. D., Kinoshita, K., Honjo, T., Fisher, A. and Durandy, A. Activation-induced cytidine deaminase (AID) deficiency causes the autosomal recessive form of the hyper-IgM syndrome (HIGM2). Cell 102, (5):565-576 (2000).

Richardson, N., Navaratnam, N. and Scott, J. (1998) Secondary structure for the apolipoprotein B mRNA editing site. AU binding proteins interact with a stem loop. J. Biol Chem. 273, 31707-31717.

Rinaldo, C., X. L. Huang, Z. F. Fan, M. Ding, L. Beltz, A. Logar, D. Panicali, G. Mazzara, J. Liebmann, and M. Cottrill. 1995. High levels of anti-human immunodeficiency virus type 1 (HIV-1) memory cytotoxic T-lymphocyte activity and low viral load are associated with lack of disease in HIV-1-infected long-term nonprogressors. Journal of Virology 69:5838-42.

Robberson, B. L., Cote, G. J. and Berget, S. M. (1990) Exon definition may facilitate splice site selection in RNAs with multiple exons. Mol. Cell. Biol. 10, 1084-1094.

Rolink, A., F. Melchers and J. Andersson, The SCID but not the RAG-2 gene product is required for S mu-S epsilon heavy chain class switching. Immunity, 1996. 5(4): p. 319-30.

Rosenberg, E. S., J. M. Billingsley, A. M. Caliendo, S. L. Boswell, P. E. Sax, S. A. Kalams, and B. D. Walker. 1997. Vigorous HIV-1-specific CD4+ T cell responses associated with control of viremia. Science 278:1447-50.

Rowland_Jones, S., J. Sutton, K. Ariyoshi, T. Dong, F. Gotch, S. McAdam, D. Whitby, S. Sabally, A. Gallimore, and T. Corrah. 1995. HIV-specific cytotoxic T-cells in HIV-exposed but uninfected Gambian women. Nature Medicine 1:59-64.

Rueter, S. M. and Emeson, R. B. (1998) Adenosine-to-inosine conversion in mRNA. In Modification and Editing of RNA (Grosjean, H. and Benne, R., eds.), pp. 343-361, American Society for Microbiology Press, Washington.

Rueter, S. M., Dawson, T. R. and Emeson, R. B. (1999) Regulation of alternative splicing by RNA editing, Nature 399, 75-80.

Sakashita, E. and H. Sakamoto, Protein-RNA and protein-protein interactions of the *Drosophila* sex-lethal mediated by its RNA-binding domains. Journal of Biochemistry, 1996. 120(5): p. 1028-33.

Sale, J. E., D. M. Calandrini, M. Takata, S. Takeda and M. S. Neuberger, Ablation of XRCC2/3 transforms immunoglobulin V gene conversion into somatic hypermutation. Nature, 2001. 412(6850): p. 921-6.

Sali, A., L. Potterton, F. Yuan, H. van Vlijmen, and M. Karplus, Evaluation of comparative protein modeling by MODELLER. Proteins. 23(3): p. 318-26 (1995).

Schock, D., Kuo, S. R., Steinburg, M. F., Bolognino, M., Sparks, J. D., Sparks, C. E. and Smith, H. C. (1996). An auxiliary factor containing a 240 kDa protein is involved in apoB RNA editing. Proc. Natl. Acad. Sci. USA 93, 1097-1102.

Schrofelbauer, B., Chen, D., and Landau, N. R. 2004. A single amino acid of APOBEC3G controls its species-specific interaction with virion infectivity factor (Vif). Proc Natl Acad Sci USA 101:3927-3932.

Scott, J. (1989) The molecular and cell biology of apolipoprotein-B. J. Mol. Med. 6, 65-80.

Seeburg, P. H., Higuchi, M. and Sprengel, R. (1998) RNA editing of brain glutamate receptor channels: mechanism and physiology. Brain Res. Rev. 26, 217-229.

Selig, L., S. Benichou, M. E. Rogel, L. I. Wu, M. A. Vodicka, J. Sire, R. Benarous, and M. Emerman, Uracil DNA glycosylase specifically interacts with Vpr of both human immunodeficiency virus type 1 and simian immunodeficiency virus of sooty mangabeys, but binding does not correlate with cell cycle arrest. J Virol. 71(6):4842-6. (1997).

Shah, R. R., Knott, T. J., Legros, J. E., Navaratnam, N., Greeve, J. C. and Scott, J. Sequence requirements for the editing of apolipoprotein B mRNA. J. Biol. Chem. 266, 16301-16304 (1991).

Sheehy, A. M., Gaddis, N. C., Choi, J. D., Malim, M. H. 2002. Isolation of a human gene that inhibits HIV-1 infection and is suppressed by the viral Vif protein. Nature 418:646-650.

Shibata, R., T. Igarashi, N. Haigwood, A. Buckler-White, R. Ogert, W. Ross, R. Willey, M. W. Cho, and M. A. Martin. 1999. Neutralizing antibody directed against the HIV-1 envelope glycoprotein can completely block HIV-1/SIV chimeric virus infections of macaque monkeys. Nat Med 5:204-10.

Shindo, K., A. Takaori-Kondo, M. Kobayashi, A. Abudu, K. Fukunaga, and T. Uchiyama. 2003. The enzymatic activity of CEM15/Apobec-3G Is essential for the regulation of the infectivity of HIV-1 Virion, but not a sole determinant of Its antiviral activity. J Biol Chem. 278:44412-6.

Siddiqui, J. F. M., Van Mater, D., Sowden, M. P. and Smith, H. C. (1999) Disproportionate relationship between APOBEC-1 expression and apolipoprotein B mRNA editing activity. Exp. Cell Res. 252(1):154-164.

Simon, J. H. and M. H. Malim. The human immunodeficiency virus type 1 Vif protein modulates the postpenetration stability of viral nucleoprotein complexes. J. Virol. 70(8): 5297-305 (1996).

Simon, J. H., N. C. Gaddis, R. A. Fouchier, and M. H. Malim, Evidence for a newly discovered cellular anti-HIV-1 phenotype. Nat. Med. 4(12):1397-400 (1998).

Simpson, L. and Emeson, R. B. (1996) RNA editing. Annu. Rev. Neurosci. 19, 27-52.

Skuse, G. R., A. J. Cappione, M. Sowden, L. J. Metheny and H. C. Smith, The neurofibromatosis type I messenger RNA undergoes base-modification RNA editing. Nucleic Acids Res, 1996. 24(3): p. 478-85

Smith, H. C., Kuo, S. R., Backus, J. W., Harris, S. G., Sparks, C. E. and Sparks, J. D. (1991) In vitro mRNA editing: identification of a 27 S editing complex. Proc. Natl. Acad. Sci. U.S.A. 88, 1489-1493.

Smith, H. C. (1993) Apo B mRNA editing: the sequence to the event. Seminars in Cell Biology (Stuart, K., ed.) Saunders Sci. Publications/Academic Press, London, 4, 267-278.

Smith, H. C. and Sowden, M. P. (1996) Base modification RNA editing Trends in Genetics 12, 418-424.

Smith, H. C., Analysis of protein complexes assembled on apolipoprotein B mRNA for mooring sequence-dependent RNA editing. Methods, 1998. 15(1): p. 27-39.

Smith, H. C., Gott, J. M. and Hanson, M. R. (1997) A guide to RNA editing. RNA, 3, 1105-1123.

Sohail, A., Klapacz, J., Samaranayake, M., Ullah, A. and Bhagwat, A. Human activation-induced cytidine deaminase causes transcript-dependent, strand-biased C to U deaminations. Nucleic Acids. Res. 31(12):2990-2994 (2003).

Sova, P. and D. J. Volsky, Efficiency of viral DNA synthesis during infection of permissive and nonpermissive cells with vif-negative human immunodeficiency virus type 1. J. Virol. 67(10): 6322-6 (1993).

Sowden, M. P., Hamm, J. K. and Smith, H. C. (1996) Overexpression of APOBEC-1 results in mooring sequence dependent promiscuous RNA editing. J. Biol. Chem. 271 (6):3011-3017.

Sowden, M. P., Harrison, S. M., Ashfield, R. A., Kingsman, A. J. and Kingsman, S. M. (1989) Multiple cooperative interactions constrain BPV-1 E2 dependent activation of transcription. Nucleic Acids Res. 17, 2959-2972.

Sowden, M. P. and H. C. Smith, Commitment of apolipoprotein B RNA to the splicing pathway regulates cytidine-to-uridine editing-site utilization. Biochem J, 2001. 359(Pt 3): p. 697-705.

Sowden, M. P., Ballatori, N., de Mesy Jensen, K. L., Hamilton Reed, L., Smith, H. C., The editosome for cytidine to uridine mRNA editing has a native complexity of 27S: identification of intracellular domains containing active and inactive editing factors. J. Cell Science, 2002. 115: p. 1027-1039

Sowden, M. P., Eagleton, M. J. and Smith, H. C. (1998). ApoB RNA sequence 3' of the mooring sequence and cellular sources of auxiliary factors determine the location and extent of promiscuous editing. Nucleic Acids Res. 26, 1644-1652.

Sowden, M. P., Hamm, J. K., Spinelli, S, and Smith, H. C. (1996) Determinants involved in regulating the proportion of edited apolipoprotein B RNAs. RNA 2(3):274-288.

Spector, D. (1993) Macromolecular domains within the cell nucleus. Annu. Rev. Cell Biol. 9, 265-315.

Steinburg, M. F., Schock, D., Backus, J. W. and Smith, H. C. (1999) Tissue-specific differences in the role of RNA 3' of the apolipoprotein B mRNA mooring sequence in editosome assembly. Biochem. Biophys. Res. Commun. 263 (1):81-86.

Stopak, K., De Noronha, C., Yonemoto, W., and Greene, W. C. 2003. HIV-1 Vif Blocks the Antiviral Activity of APOBEC3G by Impairing both Its Translation and Intracellular Stability. Mol Cell 12:591-601.

Strebel, K., D. Daugherty, K. Clouse, D. Cohen, T. Folks, and M. A. Martin, The HIV 'A' (sor) gene product is essential for virus infectivity. Nature. 328(6132): p. 728-30 (1987).

Svarovskaia, E. S., H. Xu, J. L. Mbisa, R. Barr, R. J. Gorelick, A. Ono, E. O. Freed, W. S. Hu, and V. K. Pathak. 2004. Human APOBEC3G is incorporated into HIV-1 virions through interactions with viral and nonviral RNAs. J Biol Chem. 279:35822-8.

Taagepera, S., McDonald, D., Loeb, J. E., Whitaker, L. L., McElroy, A. K., Wang, J. Y. J. and Hope, T. J. (1998) Nuclear-cytoplasmic shuttling of C-ABL tyrosine kinase. Proc. Natl. Acad. Sci. U.S.A. 95, 7457-7462.

Teng, B. and N. O. Davidson, Evolution of intestinal apolipoprotein B mRNA editing. Chicken apolipoprotein B mRNA is not edited, but chicken enterocytes contain in vitro editing enhancement factor(s). J Biol Chem, 267(29): 21265-72 1992.

Teng, B., Burant, C. F. and Davidson, N. O. Molecular cloning of an apolipoprotein B messenger RNA editing protein, Science, 260:1816-1819 (1993).

Teng, B. B., S. Ochsner, Q. Zhang, K. V. Soman, P. P. Lau, and L. Chan, Mutational analysis of apolipoprotein B mRNA editing enzyme (APOBEC1). structure-function relationships of RNA editing and dimerization. J Lipid Res, 40(4): 623-35 (1999).

Van Mater, D., Sowden, M. P., Clanci, J., Sparks, J. D., Sparks, C. E., Ballitori, N. and Smith, H. C. (1998). Ethanol increases apoB mRNA editing in rat primary hepatocyte and McArdle cells. Biochem. Biophys. Res. Commun. 252, 334-339.

Van Parijs, L., Y. Refaeli, J. D. Lord, B. H. Nelson, A. K. Abbas and D. Baltimore, Uncoupling IL-2 signals that regulate T cell proliferation, survival, and Fas-mediated activation-induced cell death. Immunity, 1999. 11(3): p. 281-8.

Vartanian, J. P., A. Meyerhans, B. Asjo, and S. Wain-Hobson. 1991. Selection, recombination, and G----A hypermutation of human immunodeficiency virus type 1 genomes. J Virol 65:1779-88.

Vartanian, J. P., A. Meyerhans, M. Sala, and S. Wain-Hobson. 1994. G→A hypermutation of the human immunodeficiency virus type 1 genome: evidence for dCTP pool imbalance during reverse transcription. Proc Natl Acad Sci USA 91:3092-6.

Vartanian, J. P., M. Henry, and S. Wain-Hobson. 2002. Sustained G→A hypermutation during reverse transcription of an entire human immunodeficiency virus type 1 strain Vau group O genome. J Gen Virol 83:801-5.

von Schwedler, U., J. Song, C. Aiken, and D. Trono, Vif is crucial for human immunodeficiency virus type 1 proviral DNA synthesis in infected cells. J. Virol. 67(8): 4945-55 (1993).

von Wronski, M. A., Hirano, K. I., Cagen, L. M., Wilcox, H. G., Raghow, R., Thorngate, F. E., Heimberg, M., Davidson, N. O. and Elam, M. B. (1998). Insulin increases expression of apobec-1, the catalytic subunit of the apoB B mRNA editing complex in rat hepatocytes. Metabolism Clinical & Exp. 7, 869-873.

Walker, B. D., S. Chakrabarti, B. Moss, T. J. Paradis, T. Flynn, A. G. Durno, R. S. Blumberg, J. C. Kaplan, M. S. Hirsch, and R. T. Schooley. 1987. HIV-specific cytotoxic T lymphocytes in seropositive individuals. Nature 328:345-8.

Walker, C. M., D. J. Moody, D. P. Stites, and J. A. Levy. 1986. CD8+ lymphocytes can control HIV infection in vitro by suppressing virus replication. Science 234:1563-6.

Wedekind, J. E., G. S. Dance, M. P. Sowden, and H. C. Smith. 2003. Messenger RNA editing in mammals: new members of the APOBEC family seeking roles in the family business. Trends Genet. 19:207-16.

Wedekind, J. E., X. Kefang, G. S. Dance, M. P. Sowden, and H. C. Smith, The structure of yeast Cdd1 provides insight into the molecular details of the mRNA editase APOBEC-1. (2003—In preparation).

Wiegand, H. L., B. P. Doehle, H. P. Bogerd, and B. R. Cullen. 2004. A second human antiretroviral factor, APOBEC3F, is suppressed by the HIV-1 and HIV-2 Vif proteins. Embo J 23:2451-8.

Winn, M. D. An overview of the CCP4 project in protein crystallography: an example of a collaborative project. J Synchrotron Radiat. 10(Pt 1):23-5 (2003).

Wu, J. H., Semenkovish, C. F., Chen, S. H., Li, W. H. and Chan, L. (1990). ApoB mRNA editing: validation of a sensitive assay and developmental biology of RNA editing in the rat. J. Biol. Chem. 265, 12312-12316.

Xie, K., M. P. Sowden, G. S. Dance, A. T. Torelli, H. C. Smith, and J. E. Wedekind. 2004. The structure of a yeast RNA-editing deaminase provides insight into the fold and function of activation-induced deaminase and APOBEC-1. Proc Natl Acad Sci USA 101:8114-9.

Xu, H., E. S. Svarovskaia, R. Barr, Y. Zhang, M. A. Khan, K. Strebel, and V. K. Pathak. 2004. A single amino acid substitution in human APOBEC3G antiretroviral enzyme confers resistance to HIV-1 virion infectivity factor-induced depletion. Proc Natl Acad Sci USA 101:5652-7.

Yamanaka, S., Balestra, M., Ferrell, L., Fan, J., Arnold, K. S., Taylor, S., Taylor, J. M. and Innerarity, T. L. (1995). Apolipoprotein B mRNA-editing protein induces hepatocellular carcinoma and dysplasia in transgenic animals. Proc. Natl. Acad. Sci. USA 92, 8483-8487.

Yamanaka, S., K. S. Poksay, D. M. Driscoll, Innerarity, T. L., Hyperediting of multiple cytidines of apolipoprotein B mRNA by APOBEC-1 requires auxiliary protein(s) but not a mooring sequence motif. J. Biol. Chem. 271:11506-11510 (1996).

Yamanaka, S., Poksay, K. S., Balestra, M. E., Zeng, G. Q. and Innerarity, T. L. (1994). Cloning and mutagenesis of the rabbit apoB mRNA editing protein. J. Biol. Chem. 269, 21725-21734.

Yamanaka, S., Poksay, K. S., Arnold, K. S. and Innerarity, T. L. A novel translational repressor mRNA is edited extensively in livers containing tumors caused by the transgene expression of the apoB mRNA-editing enzyme. Genes Dev., 11, 321-33 (1997).

Yang, B., Gao, L., Li, L., Lu, Z., Fan, X., Patel, C. A., Pomerantz, R. J., DuBois, G. C. and Zhang, H. Potent suppression of viral infectivity by the peptides that inhibit multimerizations of human immunodeficiency virus type I (HIV-1) vifproteins. J. Biol Chem. 278(8):6596-6602 (2002).

Yang, O. O., S. A. Kalams, A. Trocha, H. Cao, A. Luster, R. P. Johnson, and B. D. Walker. 1997. Suppression of human immunodeficiency virus type I replication by CD8+ cells: evidence for HLA class I-restricted triggering of cytolytic and noncytolytic mechanisms. Journal of Virology 71:3120-8.

Yang, Y. and Smith, H. C. (1996) In vitro reconstitution of apolipoprotein B RNA editing activity from recombinant APOBEC-1 and McArdle cell extracts. Biochem. Biophys. Res. Commun. 218, 797-801.

Yang, Y., Ballatori, N., Smith, H. C., Synthesis and secretion of the atherogenic risk factor apoB100 is reduced through TAT-mediated protein transduction of an mRNA editase into hepatocytes. Molec. Pharm. 61:269-276 (2002).

Yang, Y., Kovalski, K. and Smith, H. C. (1997) Partial characterization of the auxiliary factors involved in apoB mRNA editing through APOBEC-1 affinity chromatography, J Biol. Chem., 272, 27700-27706.

Yang, Y., M. P., Sowden Y., Yang, H. C., Smith, Intracellular Trafficking Determinants in APOBEC-1, the Catalytic Subunit for Cytidine to Uridine Editing of Apolipoprotein B mRNA. Exp. Cell Res. 267:153-164 (2001).

Yang, Y., Sowden, M. P. and Smith, H. C. (2000) Induction of cytidine to uridine editing on cytoplasmic apolipoprotein B mRNA by overexpressing APOBEC-1. J. Biol. Chem. 275 (30):22663-22669.

Yang, Y., Yang, Y. and Smith, H. C. (1997) Multiple protein domains determine the cell type-specific nuclear distribution of the catalytic subunit required for apolipoprotein B mRNA editing. Proc. Natl. Acad. Sci. U.S.A. 94, 13075-13080.

Yoshikawa, K., Okazaki, I. M., Eto, T., Kinoshita, K., Muramatsu, M., Nagaoka, H., Honjo, T. (2002). "AID enzyme-induced hypermutation in an actively transcribed gene in fibroblasts." Science 296: 2033-2036.

Yu, Q. and C. D. Morrow, Essential regions of the tRNA primer required for HIV-1 infectivity. Nucleic Acids Res. 28(23):4783-9 (2000).

Yu, Q., D. Chen, R. Konig, R. Mariani, D. Unutmaz, and N. R. Landau. 2004. APOBEC3B and APOBEC3C are potent inhibitors of simian immunodeficiency virus replication. J Biol. Chem. 279 (51):53379-86

Yu, Q., Konig, R., Pillai, S., Chiles, K., Kearney, M., Palmer, S., Richman, D., Coffin, J. M., and Landau, N. R. 2004. Single-strand specificity of APOBEC3G accounts for minus-strand deamination of the HIV genome. Nat Struct Mol Biol 11:435-442.

Yu, X., Yu, Y., Liu, B., Luo, K., Kong, W., Mao, P., and Yu, X. F. 2003. Induction of APOBEC3G ubiquitination and degradation by an HIV-1 Vif-Cu15-SCF complex. Science 302:1056-1060.

Zhang, H., B. Yang, R. J. Pomerantz, C. Zhang, S. C. Arunachalam, and L. Gao. 2003. The cytidine deaminase CEM15 induces hypermutation in newly synthesized HIV-1 DNA. Nature 424:94-98.

Zhang, H., Pomerantz, Roger J. and Yang, Bin; Thomas Jefferson University. Multimerization of HIV-1 Vif protein as a therapeutic target. US Patent Application Publication No. 20030013844 Jan. 16, 2003.

Zhang, J., and D. M. Webb. 2004. Rapid evolution of primate antiviral enzyme APOBEC3G. Hum Mol Genet. 13:1785-91.

Zheng, Y. H., Irwin, D., Kurosu, T., Tokunaga, K., Sata, T., Peterlin, B. M. (2004) Human APOBEC3F is Another Host Factor that Blocks Human Immunodeficiency Virus Type 1 Replication. J. Virol. 78:6073-6076.

SEQUENCE LISTING

```
<160> NUMBER OF SEQ ID NOS: 63

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequences; note =
      synthetic construct

<400> SEQUENCE: 1
cgcagcctgt gtcagaaaag                                                   20

<210> SEQ ID NO 2
<211> LENGTH: 24
<212> TYPE: DNA
<213> ORGANISM: Artificial Sequence
<220> FEATURE:
<223> OTHER INFORMATION: Description of Artificial Sequences; note =
      synthetic construct

<400> SEQUENCE: 2
ccaacagtgc tgaaattcgt cata                                              24

<210> SEQ ID NO 3
<211> LENGTH: 15
<212> TYPE: DNA
<213> ORGANISM: Artificial Sequence
<220> FEATURE:
<223> OTHER INFORMATION: Description of Artificial Sequences; note =
``` synthetic construct

<400> SEQUENCE: 3
gtgccaccat gaaga                                                                          15

<210> SEQ ID NO 4
<211> LENGTH: 384
<212> TYPE: PRT
<213> ORGANISM: Artificial Sequence
<220> FEATURE:
<223> OTHER INFORMATION: Description of Artificial Sequences; note = synthetic construct

<400> SEQUENCE: 4

```
Met Lys Pro His Phe Arg Asn Thr Val Glu Arg Met Tyr Arg Asp Thr
 1               5                  10                  15

Phe Ser Tyr Asn Phe Tyr Asn Arg Pro Ile Leu Ser Arg Asn Thr
                20                  25                  30

Val Trp Leu Cys Tyr Glu Val Lys Thr Lys Gly Pro Ser Arg Pro Pro
         35                  40                  45

Leu Asp Ala Lys Ile Phe Arg Gly Gln Val Tyr Ser Glu Leu Lys Tyr
     50                  55                  60

His Pro Glu Met Arg Phe Phe His Trp Phe Ser Lys Trp Arg Lys Leu
 65                  70                  75                  80

His Arg Asp Gln Glu Tyr Glu Val Thr Trp Tyr Ile Ser Trp Ser Pro
                 85                  90                  95

Cys Thr Lys Cys Thr Arg Asp Met Ala Thr Phe Leu Ala Glu Asp Pro
            100                 105                 110

Lys Val Thr Leu Thr Ile Phe Val Ala Arg Leu Tyr Tyr Phe Trp Asp
        115                 120                 125

Pro Asp Tyr Gln Glu Ala Leu Arg Ser Leu Cys Gln Lys Arg Asp Gly
    130                 135                 140

Pro Arg Ala Thr Met Lys Ile Met Asn Tyr Asp Glu Phe Gln His Cys
145                 150                 155                 160

Trp Ser Lys Phe Val Tyr Ser Gln Arg Glu Leu Phe Glu Pro Trp Asn
                165                 170                 175

Asn Leu Pro Lys Tyr Tyr Ile Leu Leu His Ile Met Leu Gly Glu Ile
            180                 185                 190

Leu Arg His Ser Met Asp Pro Pro Thr Phe Thr Phe Asn Phe Asn Asn
        195                 200                 205

Glu Pro Trp Val Arg Gly Arg His Glu Thr Tyr Leu Cys Tyr Glu Val
    210                 215                 220

Glu Arg Met His Asn Asp Thr Trp Val Leu Leu Asn Gln Arg Arg Gly
225                 230                 235                 240

Phe Leu Cys Asn Gln Ala Pro His Lys His Gly Phe Leu Glu Gly Arg
                245                 250                 255

His Ala Glu Leu Cys Phe Leu Asp Val Ile Pro Phe Trp Lys Leu Asp
            260                 265                 270

Leu Asp Gln Asp Tyr Arg Val Thr Cys Phe Thr Ser Trp Ser Pro Cys
        275                 280                 285

Phe Ser Cys Ala Gln Glu Met Ala Lys Phe Ile Ser Lys Asn Lys His
    290                 295                 300

Val Ser Leu Cys Ile Phe Thr Ala Arg Ile Tyr Asp Asp Gln Gly Arg
305                 310                 315                 320

Cys Gln Glu Gly Leu Arg Thr Leu Ala Glu Ala Gly Ala Lys Ile Ser
                325                 330                 335
```

```
Ile Met Thr Tyr Ser Glu Phe Lys His Cys Trp Asp Thr Phe Val Asp
            340                 345                 350

His Gln Gly Cys Pro Phe Gln Pro Trp Asp Gly Leu Asp Glu His Ser
        355                 360                 365

Gln Asp Leu Ser Gly Arg Leu Arg Ala Ile Leu Gln Asn Gln Glu Asn
    370                 375                 380

<210> SEQ ID NO 5
<211> LENGTH: 1717
<212> TYPE: DNA
<213> ORGANISM: Artificial Sequence
<220> FEATURE:
<223> OTHER INFORMATION: Description of Artificial Sequences; note =
      synthetic construct

<400> SEQUENCE: 5
ctgccagggg gagggcccca gagaaaacca gaaagagggt gagagactga ggaagataaa      60
gcgtcccagg gcctcctaca ccagcgcctg agcaggaagc ggagggggcc atgactacga     120
ggccctggga ggtcacttta ggagggctg tcctaaaacc agaagcttgg agcagaaagt     180
gaaaccctgg tgctccagac aaagatctta gtcgggacta ccggccaag gatgaagcct      240 cacttcagaa acacagtgga gcgaatgtat cgagacacat tctcctacaa cttttataat     300
agacccatcc tttctcgtcg aataccgtc tggctgtgct acgaagtgaa aacaaagggt      360
ccctcaaggc ccccttggga cgcaaagatc tttcgaggcc aggtgtattc cgaacttaag     420
taccacccag agatgagatt cttccactgg ttcagcaagt ggaggaagct gcatcgtgac     480
caggagtatg aggtcacctg gtacatatcc tggagcccct gcacaaagtg tacaagggat     540
atggccacgt cctggccga ggacccgaag gttaccctga ccatcttcgt tgcccgcctc      600
tactacttct gggacccaga ttaccaggag gcgcttcgca gcctgtgtca gaaaagagac     660
ggtccgcgtg ccaccatgaa gatcatgaat tatgacgaat tcagcactg ttggagcaag      720 ttcgtgtaca gccaaagaga gctatttgag ccttggaata atctgcctaa atattatata     780
ttactgcaca tcatgctggg ggagattctc agacactcga tggatccacc cacattcact     840
ttcaacttta caatgaacc ttgggtcaga ggacggcatg agacttacct gtgttatgag      900
gtggagcgca tgcacaatga cacctgggtc ctgctgaacc agcgcagggg ctttctatgc     960
aaccaggctc acataaaca cggtttcctt gaaggccgcc atgcagagct gtgcttcctg     1020
gacgtgattc ccttttggaa gctggacctg gaccaggact acagggttac ctgcttcacc     1080
tcctggagcc cctgcttcag ctgtgcccag gaaatggcta aattcatttc aaaaaacaaa     1140
cacgtgagcc tgtgcatctt cactgcccgc atctatgatg atcaaggaag atgtcaggag     1200
gggctgcgca ccctggccga ggctgggcc aaaatttcaa taatgacata cagtgaattt     1260
aagcactgct gggacaccct tgtggaccac cagggatgtc ccttccagcc ctgggatgga     1320
ctagatgagc acagccaaga cctgagtggg aggctgcggg ccattctcca gaatcaggaa     1380
aactgaagga tgggcctcag tctctaagga aggcagagac ctgggttgag cctcagaata     1440
aaagatcttc ttccaagaaa tgcaaacagg ctgttcacca ccatctccag ctgatcacag     1500
acaccagcaa agcaatgcac tcctgaccaa gtagattctt ttaaaaatta gagtgcatta     1560
ctttgaatca aaaatttatt tatatttcaa gaataaagta ctaagattgt gctcaataca     1620
cagaaaagtt tcaaacctac taatccagcg acaatttgaa tcggttttgt aggtagagga     1680
ataaaatgaa atactaaatc tttctgtaaa aaaaaaa                              1717
```

<210> SEQ ID NO 6
<211> LENGTH: 384
<212> TYPE: PRT
<213> ORGANISM: Artificial Sequence
<220> FEATURE:
<223> OTHER INFORMATION: Description of Artificial Sequences; note = synthetic construct

<400> SEQUENCE: 6

Met Lys Pro His Phe Arg Asn Thr Val Glu Arg Met Tyr Arg Asp Thr
1               5                   10                  15

Phe Ser Tyr Asn Phe Tyr Asn Arg Pro Ile Leu Ser Arg Arg Asn Thr
            20                  25                  30

Val Trp Leu Cys Tyr Glu Val Lys Thr Lys Gly Pro Ser Arg Pro Pro
        35                  40                  45

Leu Asp Ala Lys Ile Phe Arg Gly Gln Val Tyr Ser Glu Leu Lys Tyr
    50                  55                  60

His Pro Glu Met Arg Phe Phe His Trp Phe Ser Lys Trp Arg Lys Leu
65                  70                  75                  80

His Arg Asp Gln Glu Tyr Glu Val Thr Trp Tyr Ile Ser Trp Ser Pro
                85                  90                  95

Cys Thr Lys Cys Thr Arg Asp Met Ala Thr Phe Leu Ala Glu Asp Pro
            100                 105                 110

Lys Val Thr Leu Thr Ile Phe Val Ala Arg Leu Tyr Tyr Phe Trp Asp
        115                 120                 125

Pro Asp Tyr Gln Glu Ala Leu Arg Ser Leu Cys Gln Lys Arg Asp Gly
    130                 135                 140

Pro Arg Ala Thr Met Lys Ile Met Asn Tyr Asp Glu Phe Gln His Cys
145                 150                 155                 160

Trp Ser Lys Phe Val Tyr Ser Gln Arg Glu Leu Phe Glu Pro Trp Asn
                165                 170                 175

Asn Leu Pro Lys Tyr Tyr Ile Leu Leu His Ile Met Leu Gly Glu Ile
            180                 185                 190

Leu Arg His Ser Met Asp Pro Pro Thr Phe Thr Phe Asn Phe Asn Asn
        195                 200                 205

Glu Pro Trp Val Arg Gly Arg His Glu Thr Tyr Leu Cys Tyr Glu Val
    210                 215                 220

Glu Arg Met His Asn Asp Thr Trp Val Leu Leu Asn Gln Arg Arg Gly
225                 230                 235                 240

Phe Leu Cys Asn Gln Ala Pro His Lys His Gly Phe Leu Glu Gly Arg
                245                 250                 255

His Ala Glu Leu Cys Phe Leu Asp Val Ile Pro Phe Trp Lys Leu Asp
            260                 265                 270

Leu Asp Gln Asp Tyr Arg Val Thr Cys Phe Thr Ser Trp Ser Pro Cys
        275                 280                 285

Phe Ser Cys Ala Gln Glu Met Ala Lys Phe Ile Ser Lys Asn Lys His
    290                 295                 300

Val Ser Leu Cys Ile Phe Thr Ala Arg Ile Tyr Asp Asp Gln Gly Arg
305                 310                 315                 320

Cys Gln Glu Gly Leu Arg Thr Leu Ala Glu Ala Gly Ala Lys Ile Ser
                325                 330                 335

Ile Met Thr Tyr Ser Glu Phe Lys His Cys Trp Asp Thr Phe Val Asp
            340                 345                 350

His Gln Gly Cys Pro Phe Gln Pro Trp Asp Gly Leu Asp Glu His Ser
        355                 360                 365

Gln Asp Leu Ser Gly Arg Leu Arg Ala Ile Leu Gln Asn Gln Glu Asn
    370                 375                 380

<210> SEQ ID NO 7
<211> LENGTH: 1155
<212> TYPE: DNA
<213> ORGANISM: Artificial Sequence
<220> FEATURE:
<223> OTHER INFORMATION: Description of Artificial Sequences; note = synthetic construct

<400> SEQUENCE: 7

```
atgaagcctc acttcagaaa cacagtggag cgaatgtatc gagacacatt ctcctacaac    60
tttttataata gacccatcct ttctcgtcgg aataccgtct ggctgtgcta cgaagtgaaa   120
acaaagggtc cctcaaggcc ccctttggac gcaaagatct tcgaggcca ggtgtattcc    180
gaacttaagt accacccaga tgagattc ttccactggt tcagcaagtg gaggaagctg     240
catcgtgacc aggagtatga ggtcacctgg tacatatcct ggagccctg cacaaagtgt    300
acaagggata tggccacgtt cctggccgag gacccgaagg ttaccctgac catcttcgtt   360
gcccgcctct actacttctg ggacccagat taccaggagg cgcttcgcag cctgtgtcag   420
aaaagagacg gtccgcgtgc caccatgaag atcatgaatt atgacgaatt tcagcactgt   480
tggagcaagt tcgtgtacag ccaaagagag ctatttgagc cttggaataa tctgcctaaa   540
tattatatat tactgcacat catgctgggg gagattctca gacactcgat ggatccaccc   600
acattcactt tcaactttaa caatgaacct tgggtcagag acggcatga acttacctg     660
tgttatgagg tggagcgcat gcacaatgac acctgggtcc tgctgaacca gcgcagggc    720
tttctatgca accaggctcc acataaacac ggtttccttg aaggccgcca tgcagagctg   780
tgcttcctgg acgtgattcc cttttggaag ctggacctgg accaggacta cagggttacc   840
tgcttcacct cctggagccc ctgcttcagc tgtgcccagg aaatggctaa attcatttca   900
aaaaacaaac acgtgagcct gtgcatcttc actgcccgca tctatgatga tcaaggaaga   960
tgtcaggagg ggctgcgcac cctggccgag gctggggcca aaatttcaat aatgacatac  1020
agtgaattta gcactgctgg gacacccttt gtggaccacc agggatgtcc cttccagccc  1080
tgggatggac tagatgagca cagccaagac ctgagtggga ggctgcgggc cattctccag  1140
aatcaggaaa actga                                                   1155
```

<210> SEQ ID NO 8
<211> LENGTH: 382
<212> TYPE: PRT
<213> ORGANISM: Artificial Sequence
<220> FEATURE:
<223> OTHER INFORMATION: Description of Artificial Sequences; note = synthetic construct

<400> SEQUENCE: 8

Met Asn Pro Gln Ile Arg Asn Pro Met Glu Arg Met Tyr Arg Asp Thr
1               5                   10                  15

Phe Tyr Asp Asn Phe Glu Asn Glu Pro Ile Leu Tyr Gly Arg Ser Tyr
                20                  25                  30

Thr Trp Leu Cys Tyr Glu Val Lys Ile Lys Arg Gly Arg Ser Asn Leu
            35                  40                  45

Leu Trp Asp Thr Gly Val Phe Arg Gly Gln Val Tyr Phe Lys Pro Gln
        50                  55                  60

Tyr His Ala Glu Met Cys Phe Leu Ser Trp Phe Cys Gly Asn Gln Leu

```
            65                  70                  75                  80
Pro Ala Tyr Lys Cys Phe Gln Ile Thr Trp Phe Val Ser Trp Thr Pro
                     85                  90                  95

Cys Pro Asp Cys Val Ala Lys Leu Ala Glu Phe Leu Ser Glu His Pro
                100                 105                 110

Asn Val Thr Leu Thr Ile Ser Ala Ala Arg Leu Tyr Tyr Tyr Trp Glu
            115                 120                 125

Arg Asp Tyr Arg Arg Ala Leu Cys Arg Leu Ser Gln Ala Gly Ala Arg
        130                 135                 140

Val Thr Ile Met Asp Tyr Glu Glu Phe Ala Tyr Cys Trp Glu Asn Phe
145                 150                 155                 160

Val Tyr Asn Glu Gly Gln Gln Phe Met Pro Trp Tyr Lys Phe Asp Glu
                165                 170                 175

Asn Tyr Ala Phe Leu His Arg Thr Leu Lys Glu Ile Leu Arg Tyr Leu
            180                 185                 190

Met Asp Pro Asp Thr Phe Thr Phe Asn Phe Asn Asn Asp Pro Leu Val
        195                 200                 205

Leu Arg Arg Arg Gln Thr Tyr Leu Cys Tyr Glu Val Glu Arg Leu Asp
210                 215                 220

Asn Gly Thr Trp Val Leu Met Asp Gln His Met Gly Phe Leu Cys Asn
225                 230                 235                 240

Glu Ala Lys Asn Leu Leu Cys Gly Phe Tyr Gly Arg His Ala Glu Leu
                245                 250                 255

Arg Phe Leu Asp Leu Val Pro Ser Leu Gln Leu Asp Pro Ala Gln Ile
            260                 265                 270

Tyr Arg Val Thr Trp Phe Ile Ser Trp Ser Pro Cys Phe Ser Trp Gly
        275                 280                 285

Cys Ala Gly Glu Val Arg Ala Phe Leu Gln Glu Asn Thr His Val Arg
            290                 295                 300

Leu Arg Ile Phe Ala Ala Arg Ile Tyr Asp Tyr Asp Pro Leu Tyr Lys
305                 310                 315                 320

Glu Ala Leu Gln Met Leu Arg Asp Ala Gly Ala Gln Val Ser Ile Met
                325                 330                 335

Thr Tyr Asp Glu Phe Glu Tyr Cys Trp Asp Thr Phe Val Tyr Arg Gln
            340                 345                 350

Gly Cys Pro Phe Gln Pro Trp Asp Gly Leu Glu His Ser Gln Ala
        355                 360                 365

Leu Ser Gly Arg Leu Arg Ala Ile Leu Gln Asn Gln Gly Asn
    370                 375                 380

<210> SEQ ID NO 9
<211> LENGTH: 1536
<212> TYPE: DNA
<213> ORGANISM: Artificial Sequence
<220> FEATURE:
<223> OTHER INFORMATION: Description of Artificial Sequences; note =
      synthetic construct

<400> SEQUENCE: 9
acagagcttc aaaaaaagag cgggacaggg acaagcgtat ctaagaggct gaacatgaat     60
ccacagatca gaaatccgat ggagcggatg tatcgagaca cattctacga caactttgaa    120
aacgaaccca tcctctatgg tcggagctac acttggctgt gctatgaagt gaaaataaag    180
aggggccgct caaatctcct ttgggacaca ggggtctttc gaggccaggt gtatttcaag    240
cctcagtacc acgcagaaat gtgcttcctc tcttggttct gtggcaacca gctgcctgct    300
```

```
tacaagtgtt tccagatcac ctggtttgta tcctggaccc cctgcccgga ctgtgtggcg      360
aagctggccg aattcctgtc tgagcacccc aatgtcaccc tgaccatctc tgccgcccgc      420
ctctactact actgggaaag agattaccga agggcgctct gcaggctgag tcaggcagga      480
gcccgcgtga cgatcatgga ctatgaagaa tttgcatact gctgggaaaa ctttgtgtac      540
aatgaaggtc agcaattcat gccttggtac aaattcgatg aaaattatgc attcctgcac      600
cgcacgctaa aggagattct cagatacctg atggatccag acacattcac tttcaacttt      660
aataatgacc ctttggtcct tcgacggcgc cagacctact tgtgctatga ggtggagcgc      720
ctggacaatg caccggggt cctgatggac agcacatgg gctttctatg caacgaggct      780
aagaatcttc tctgtggctt ttacggccgc catgcggagc tgcgcttctt ggacctggtt      840
ccttctttgc agttggaccc ggcccagatc tacagggtca cttggttcat ctcctggagc      900
ccctgcttct cctggggctg tgccggggaa gtgcgtgcgt tccttcagga gaacacacac      960
gtgagactgc gcatcttcgc tgcccgcatc tatgattacg accccctata taggaggcg     1020 ctgcaaatgc tgcgggatgc tggggcccaa gtctccatca tgacctacga tgagtttgag     1080
tactgctggg acacctttgt gtaccgccag ggatgtccct tccagccctg ggatggacta     1140
gaggagcaca gccaagccct gagtgggagg ctgcgggcca ttctccagaa tcagggaaac     1200
tgaaggatgg gcctcagtct ctaaggaagg cagagacctg ggttgagcag cagaataaaa     1260
gatcttcttc caagaaatgc aaacagaccg ttcaccacca tctccagctg ctcacagaca     1320
ccagcaaagc aatgtgctcc tgatcaagta gatttttaa aaatcagagt caattaattt     1380
taattgaaaa tttctcttat gttccaagtg tacaagagta agattatgct caatattccc     1440
agaatagttt tcaatgtatt aatgaagtga ttaattggct ccatatttag actaataaaa     1500
cattaagaat cttccataat tgtttccaca aacact                                1536
```

<210> SEQ ID NO 10
<211> LENGTH: 190
<212> TYPE: PRT
<213> ORGANISM: Artificial Sequence
<220> FEATURE:
<223> OTHER INFORMATION: Description of Artificial Sequences; note = synthetic construct

<400> SEQUENCE: 10

```
Met Asn Pro Gln Ile Arg Asn Pro Met Lys Ala Met Tyr Pro Gly Thr
 1               5                  10                  15

Phe Tyr Phe Gln Phe Lys Asn Leu Trp Glu Ala Asn Asp Arg Asn Glu
            20                  25                  30

Thr Trp Leu Cys Phe Thr Val Glu Gly Ile Lys Arg Arg Ser Val Val
        35                  40                  45

Ser Trp Lys Thr Gly Val Phe Arg Asn Gln Val Asp Ser Glu Thr His
    50                  55                  60

Cys His Ala Glu Arg Cys Phe Leu Ser Trp Phe Cys Asp Asp Ile Leu
65                  70                  75                  80

Ser Pro Asn Thr Lys Tyr Gln Val Thr Trp Tyr Thr Ser Trp Ser Pro
                85                  90                  95

Cys Pro Asp Cys Ala Gly Glu Val Ala Glu Phe Leu Ala Arg His Ser
            100                 105                 110

Asn Val Asn Leu Thr Ile Phe Thr Ala Arg Leu Tyr Tyr Phe Gln Tyr
        115                 120                 125

Pro Cys Tyr Gln Glu Gly Leu Arg Ser Leu Ser Gln Glu Gly Val Ala
```

```
                  130                 135                 140
Val Glu Ile Met Asp Tyr Glu Asp Phe Lys Tyr Cys Trp Glu Asn Phe
145                 150                 155                 160

Val Tyr Asn Asp Asn Glu Pro Phe Lys Pro Trp Lys Gly Leu Lys Thr
                165                 170                 175

Asn Phe Arg Leu Leu Lys Arg Arg Leu Arg Glu Ser Leu Gln
            180                 185                 190

<210> SEQ ID NO 11
<211> LENGTH: 1127
<212> TYPE: DNA
<213> ORGANISM: Artificial Sequence
<220> FEATURE:
<223> OTHER INFORMATION: Description of Artificial Sequences; note =
      synthetic construct

<400> SEQUENCE: 11
ttaaagaggg ctgctcaact gcaaggacgc tgtaagcagg aagagaagcc acagcgcttc      60
agaaaagagt gggacaggga caagcatatc taagaggctg aacatgaatc cacagatcag    120
aaacccgatg aaggcaatgt atccaggcac attctacttc caatttaaaa acctatggga    180
agccaacgat cggaacgaaa cttggctgtg cttcaccgtg gaaggtataa agcgccgctc    240
agttgtctcc tggaagacgg gcgtcttccg aaaccaggtg gattctgaga cccattgtca    300
tgcagaaagg tgcttcctct cttggttctg cgacgacata ctgtctccta acacaaagta    360
ccaggtcacc tggtacacat cttggagccc ttgcccagac tgtgcagggg aggtggccga    420
gttcctggcc aggcacagca acgtgaatct caccatcttc accgcccgcc tctactactt    480
ccagtatcca tgttaccagg aggggctccg cagcctgagt caggaagggg tcgctgtgga    540
gatcatggac tatgaagatt ttaaatattg ttgggaaaac tttgtgtaca atgataatga    600
gccattcaag ccttggaagg gattaaaaac caactttcga cttctgaaaa gaaggctacg    660
ggagagtctc cagtgagggg tctccctggg cctcatggtc tgtctcctct agcctcctgc    720
tcatgctgca cgggcctccc ctccaccctg acccgctct gtttctgcct ggtcatcctg    780
agcccctcct ggcctcaggg ccattccaca gtgctcccct gcctcaccgc ttcctcctcg    840
ctcttccaga ctcttcctgc agaggctcct ttctgcctcc atggctatcc atccaccccc    900
acagaccccg ttcctccagc ctgcgtgccc ctaacctggc ttttcccatc tccccagcat    960
aaccaaatct tactaaactc atcctaggct gggcatggtg actcacgcct gtaatccccc   1020
agcaatttgg gaggcaaagg tgggagaatc gcgtgagccc aggagttcca gaccaggctg   1080
ggtcacatga caaagcccca tctctacaaa aaaaaaaaaa aaaaaa                   1127

<210> SEQ ID NO 12
<211> LENGTH: 373
<212> TYPE: PRT
<213> ORGANISM: Artificial Sequence
<220> FEATURE:
<223> OTHER INFORMATION: Description of Artificial Sequences; note =
      synthetic construct

<400> SEQUENCE: 12

Met Lys Pro His Phe Arg Asn Thr Val Glu Arg Met Tyr Arg Asp Thr
1               5                   10                  15

Phe Ser Tyr Asn Phe Tyr Asn Arg Pro Ile Leu Ser Arg Arg Asn Thr
            20                  25                  30

Val Trp Leu Cys Tyr Glu Val Lys Thr Lys Gly Pro Ser Arg Pro Arg
        35                  40                  45
```

Leu Asp Ala Lys Ile Phe Arg Gly Gln Val Tyr Ser Gln Pro Glu His
    50                  55                  60

His Ala Glu Met Cys Phe Leu Ser Trp Phe Cys Gly Asn Gln Leu Pro
65                  70                  75                  80

Ala Tyr Lys Cys Phe Gln Ile Thr Trp Phe Val Ser Trp Thr Pro Cys
                85                  90                  95

Pro Asp Cys Val Ala Lys Leu Ala Glu Phe Leu Ala Glu His Pro Asn
            100                 105                 110

Val Thr Leu Thr Ile Ser Ala Ala Arg Leu Tyr Tyr Tyr Trp Glu Arg
        115                 120                 125

Asp Tyr Arg Arg Ala Leu Cys Arg Leu Ser Gln Ala Gly Ala Arg Val
    130                 135                 140

Lys Ile Met Asp Asp Glu Glu Phe Ala Tyr Cys Trp Glu Asn Phe Val
145                 150                 155                 160

Tyr Ser Glu Gly Gln Pro Phe Met Pro Trp Tyr Lys Phe Asp Asp Asn
                165                 170                 175

Tyr Ala Phe Leu His Arg Thr Leu Lys Glu Ile Leu Arg Asn Pro Met
            180                 185                 190

Glu Ala Met Tyr Pro His Ile Phe Tyr Phe His Phe Lys Asn Leu Arg
        195                 200                 205

Lys Ala Tyr Gly Arg Asn Glu Ser Trp Leu Cys Phe Thr Met Glu Val
210                 215                 220

Val Lys His His Ser Pro Val Ser Trp Lys Arg Gly Val Phe Arg Asn
225                 230                 235                 240

Gln Val Asp Pro Glu Thr His Cys His Ala Glu Arg Cys Phe Leu Ser
                245                 250                 255

Trp Phe Cys Asp Asp Ile Leu Ser Pro Asn Thr Asn Tyr Glu Val Thr
            260                 265                 270

Trp Tyr Thr Ser Trp Ser Pro Cys Pro Glu Cys Ala Gly Glu Val Ala
        275                 280                 285

Glu Phe Leu Ala Arg His Ser Asn Val Asn Leu Thr Ile Phe Thr Ala
    290                 295                 300

Arg Leu Tyr Tyr Phe Trp Asp Thr Asp Tyr Gln Glu Gly Leu Arg Ser
305                 310                 315                 320

Leu Ser Gln Glu Gly Ala Ser Val Glu Ile Met Gly Tyr Lys Asp Phe
                325                 330                 335

Lys Tyr Cys Trp Glu Asn Phe Val Tyr Asn Asp Asp Glu Pro Phe Lys
            340                 345                 350

Pro Trp Lys Gly Leu Lys Tyr Asn Phe Leu Phe Leu Asp Ser Lys Leu
        355                 360                 365

Gln Glu Ile Leu Glu
    370

<210> SEQ ID NO 13
<211> LENGTH: 2672
<212> TYPE: DNA
<213> ORGANISM: Artificial Sequence
<220> FEATURE:
<223> OTHER INFORMATION: Description of Artificial Sequences; note =
      synthetic construct

<400> SEQUENCE: 13 ttcccttttgc aattgccttg ggtcctgccg cacagagcgg cctgtcttta tcagaggtcc      60
ctctgccagg gggagggccc cagagaaaac cagaaagagg gtgagagact gaggaagata     120

| | | | | |
|---|---|---|---|---|
| aagcgtccca | gggcctccta | caccagcgcc | tgagcaggaa | ggggagggg ccatgactac | 180 |
| gaggccctgg | gaggtcactt | tagggagggc | tgtcctgaaa | cctggagcct ggagcagaaa | 240 |
| gtgaaaccct | ggtgctccag | acaaagatct | tagtcgggac | tagccggcca aggatgaagc | 300 |
| ctcacttcag | aaacacagtg | gagcgaatgt | atcgagacac | attctcctac aactttata | 360 |
| atagacccat | cctttctcgt | cggaataccg | tctggctgtg | ctacgaagtg aaaacaaagg | 420 |
| gtccctcaag | gccccgtttg | gacgcaaaga | tctttcgagg | ccaggtgtat tcccagcctg | 480 |
| agcaccacgc | agaaatgtgc | ttcctctctt | ggttctgtgg | caaccagctg cctgcttaca | 540 |
| agtgtttcca | gatcacctgg | tttgtatcct | ggaccccctg | cccggactgt gtggcgaagc | 600 |
| tggccgaatt | cctggctgag | caccccaatg | tcaccctgac | catctccgcc gcccgcctct | 660 |
| actactactg | ggaaagagat | taccgaaggg | cgctctgcag | gctgagtcag gcaggggccc | 720 |
| gcgtgaagat | tatggacgat | gaagaatttg | catactgctg | ggaaaacttt gtgtacagtg | 780 |
| aaggtcagcc | attcatgcct | tggtacaaat | tcgatgacaa | ttatgcattc ctgcaccgca | 840 |
| cgctaaagga | gattctcaga | aacccgatgg | aggcaatgta | tccacacata ttctacttcc | 900 |
| actttaaaaa | cctacgcaaa | gcctatggtc | ggaacgaaag | ctggctgtgc ttcaccatgg | 960 |
| aagttgtaaa | gcaccactca | cctgtctcct | ggaagagggg | cgtcttccga aaccaggtgg | 1020 |
| atcctgagac | ccattgtcat | gcagaaaggt | gcttcctctc | ttggttctgt gacgacatac | 1080 |
| tgtctcctaa | cacaaactac | gaggtcacct | ggtacacatc | ttggagccct tgcccagagt | 1140 |
| gtgcagggga | ggtggccgag | ttcctggcca | ggcacagcaa | cgtgaatctc accatcttca | 1200 |
| ccgcccgcct | ctactactc | tgggatacag | attaccagga | ggggctccgc agcctgagtc | 1260 |
| aggaagggc | ctccgtggag | atcatgggct | acaaagattt | taaatattgt tgggaaaact | 1320 |
| ttgtgtacaa | tgatgatgag | ccattcaagc | cttggaaagg | actaaaatac aactttctat | 1380 |
| tcctggacag | caagctgcag | gagattctcg | agtgaggggt | ctccccgggc ctcatggtct | 1440 |
| gtctcctcta | gcctcctgct | catgttgtgc | aggcctcccc | tccatcctgg accagctgtg | 1500 |
| cttttgcctg | gtcatcctga | gcccctcctg | gcctcagggc | cattccatag tgctcccctg | 1560 |
| cctcaccacc | tcctctccgc | tctcccaggc | tcttcctgca | gaggcctctt tctgcctcca | 1620 |
| tggctatcca | tccacccacc | aagaccctgt | tccctgagcc | tgcatgcccc taacctgcct | 1680 |
| tttcccatct | ccccagcata | acctaatatt | tttttttttt | ttttgagacg gaatttcgct | 1740 |
| ctgtcaccca | gactggagtg | caatggcttg | atcttggctc | actgcaaact ctgcctacca | 1800 |
| ggttcaagcg | attctcctgc | ctcgcctcc | cgagtagctg | gaattacaga cgcctgccac | 1860 |
| cacgcacagc | taactttttt | ttttttgta | tttttagtag | tgactgggtt tcaccatgtt | 1920 |
| ggccaggctg | gtcttgaact | cctgacctca | ggtgatccgc | ctatctcagc ctcccaaagt | 1980 |
| gctgggatta | caggcgtgag | ccactggccc | ggcggcacaa | ccaaatctta ttaaactcac | 2040 |
| cctaggctgg | ccgcggtgac | tcatgcctat | aatcccccag | caatttggga ggcagaggtg | 2100 |
| agagaatcgc | ttgagcccag | gaattcgaga | ccagcctggg | ccacatgaca aagcccatc | 2160 |
| tctacaaaaa | aattacaaaa | aaaaaaaaa | caggtgtggt | ggcatgcacc tgtagtttaa | 2220 |
| gctgcttgga | aggatgaagt | gggaggattg | cttgagccgg | ggaggtggag gctgcagtga | 2280 |
| actgagatca | cgtcactgaa | ctccagtctg | agcaacagat | cgagaccctg cctgaaaata | 2340 |
| aatcaataaa | taaactcaac | cgaaatgggt | atgaaagttg | aaatgggtat gtaagttgaa | 2400 |
| aaccagaagt | tttgagaaac | atcctttgtt | aactttcatc | ctacaaattg ggtcattcat | 2460 |
| gtcctacgca | gctaaaacag | agcccaggag | ccagggagga | aaagcagtca ggccacacac | 2520 |

```
cattgctccc aaaatggact tctctgcaag cctgactcct gaaactgtgc attgtaccct    2580
gaaaccagct ttatccatag cttctgcaat aaatggctgt aagtcttgga aaaaaaaaa    2640 aaaaaaaaaa aaaaaaaaaa aaaaaaaaaa aa                                 2672
```

<210> SEQ ID NO 14
<211> LENGTH: 4
<212> TYPE: PRT
<213> ORGANISM: Artificial Sequence
<220> FEATURE:
<223> OTHER INFORMATION: Description of Artificial Sequences; note = synthetic construct

<400> SEQUENCE: 14

Pro Pro Leu Pro
1

<210> SEQ ID NO 15
<211> LENGTH: 67
<212> TYPE: DNA
<213> ORGANISM: Artificial Sequence
<220> FEATURE:
<223> OTHER INFORMATION: Description of Artificial Sequences; note = synthetic construct

<400> SEQUENCE: 15

```
acagagcttc aaaaaagag cgggacaggg acaagcgtat ctaagaggct gaacatgaat    60
ccacaga                                                             67
```

<210> SEQ ID NO 16
<211> LENGTH: 97
<212> TYPE: DNA
<213> ORGANISM: Artificial Sequence
<220> FEATURE:
<223> OTHER INFORMATION: Description of Artificial Sequences; note = synthetic construct

<400> SEQUENCE: 16

```
cctggggctg tgccggggaa gtgcgtgcgt tccttcagga gaacacacac gtgagactgc    60
gcatcttcgc tgcccgcatc tatgattacg accccct                             97
```

<210> SEQ ID NO 17
<211> LENGTH: 194
<212> TYPE: DNA
<213> ORGANISM: Artificial Sequence
<220> FEATURE:
<223> OTHER INFORMATION: Description of Artificial Sequences; note = synthetic construct

<400> SEQUENCE: 17

```
ttaaagaggg ctgctcaact gcaaggacgc tgtaagcagg aagagaagcc acagcgcttc    60
agaaaagagt gggacaggga caagcatatc taagaggctg aacatgaatc cacagatcag   120
aaacccgatg aaggcaatgt atccaggcac attctacttc caatttaaaa acctatggga   180
agccaacgat cgga                                                     194
```

<210> SEQ ID NO 18
<211> LENGTH: 60
<212> TYPE: DNA
<213> ORGANISM: Artificial Sequence
<220> FEATURE:
<223> OTHER INFORMATION: Description of Artificial Sequences; note = synthetic construct -continued

<400> SEQUENCE: 18 ttcccttttgc aattgccttg ggtcctgccg cacagagcgg cctgtctta tcagaggtcc    60

<210> SEQ ID NO 19
<211> LENGTH: 397
<212> TYPE: DNA
<213> ORGANISM: Artificial Sequence
<220> FEATURE:
<223> OTHER INFORMATION: Description of Artificial Sequences; note = synthetic construct

<400> SEQUENCE: 19
aatgatgatg agccattcaa gccttggaaa ggactaaaat acaactttct attcctggac    60
agcaagctgc aggagattct cgagtgaggg gtctccccgg gcctcatggt ctgtctcctc   120
tagcctcctg ctcatgttgt gcaggcctcc cctccatcct ggaccagctg tgcttttgcc   180
tggtcatcct gagcccctcc tggcctcagg gccattccat agtgctcccc tgcctcacca   240
cctcctctcc gctctcccag gctcttcctg cagaggcctc tttctgcctc catggctatc   300
catccaccca ccaagaccct gttccctgag cctgcatgcc cctaacctgc cttttcccat   360
ctccccagca taacctaata ttttttttttt ttttttg                          397

<210> SEQ ID NO 20
<211> LENGTH: 24
<212> TYPE: DNA
<213> ORGANISM: Artificial Sequence
<220> FEATURE:
<223> OTHER INFORMATION: Description of Artificial Sequences; note = synthetic construct

<400> SEQUENCE: 20
atactgctta aagtcgtgac aacc                                            24

<210> SEQ ID NO 21
<211> LENGTH: 15
<212> TYPE: DNA
<213> ORGANISM: Artificial Sequence
<220> FEATURE:
<223> OTHER INFORMATION: Description of Artificial Sequences; note = synthetic construct

<400> SEQUENCE: 21
cacggtggta cttct                                                      15

<210> SEQ ID NO 22
<211> LENGTH: 142
<212> TYPE: PRT
<213> ORGANISM: Artificial Sequence
<220> FEATURE:
<223> OTHER INFORMATION: Description of Artificial Sequences; note = synthetic construct

<400> SEQUENCE: 22

Met Lys Val Gly Gly Ile Glu Asp Arg Gln Leu Glu Ala Leu Lys Arg
 1               5                  10                  15

Ala Ala Leu Lys Ala Cys Glu Leu Ser Tyr Ser Pro Tyr Ser His Phe
            20                  25                  30

Arg Val Gly Cys Ser Ile Leu Thr Asn Asn Asp Val Ile Phe Thr Gly
        35                  40                  45

Ala Asn Val Glu Asn Ala Ser Tyr Ser Asn Cys Ile Cys Ala Glu Arg
    50                  55                  60

Ser Ala Met Ile Gln Val Leu Met Ala Gly His Arg Ser Gly Trp Lys

```
                65                  70                  75                  80
Cys Met Val Ile Cys Gly Asp Ser Glu Asp Gln Cys Val Ser Pro Cys
                    85                  90                  95

Gly Val Cys Arg Gln Phe Ile Asn Glu Phe Val Val Lys Asp Phe Pro
                100                 105                 110

Ile Val Met Leu Asn Ser Thr Gly Ser Arg Ser Lys Val Met Thr Met
                115                 120                 125

Gly Glu Leu Leu Pro Met Ala Phe Gly Pro Ser His Leu Asn
        130                 135                 140

<210> SEQ ID NO 23
<211> LENGTH: 130
<212> TYPE: PRT
<213> ORGANISM: Artificial Sequence
<220> FEATURE:
<223> OTHER INFORMATION: Description of Artificial Sequences; note =
      synthetic construct

<400> SEQUENCE: 23

Met Asn Arg Gln Glu Leu Ile Thr Glu Ala Leu Lys Ala Arg Asp Met
  1               5                  10                  15

Ala Tyr Ala Pro Tyr Ser Lys Phe Gln Val Gly Ala Ala Leu Leu Thr
             20                  25                  30

Lys Asp Gly Lys Val Tyr Arg Gly Asn Ile Glu Asn Ala Ala Tyr Ser
         35                  40                  45

Met Cys Asn Cys Ala Glu Arg Thr Ala Leu Phe Lys Ala Val Ser Glu
     50                  55                  60

Gly Asp Thr Glu Phe Gln Met Leu Ala Val Ala Ala Asp Thr Pro Gly
 65                  70                  75                  80

Pro Val Ser Pro Cys Gly Ala Cys Arg Gln Val Ile Ser Glu Leu Cys
                 85                  90                  95

Thr Lys Asp Val Ile Val Val Leu Thr Asn Leu Gln Gly Gln Ile Lys
                100                 105                 110

Glu Met Thr Val Glu Glu Leu Leu Pro Gly Ala Phe Ser Ser Glu Asp
            115                 120                 125

Leu His
    130

<210> SEQ ID NO 24
<211> LENGTH: 123
<212> TYPE: PRT
<213> ORGANISM: Artificial Sequence
<220> FEATURE:
<223> OTHER INFORMATION: Description of Artificial Sequences; note =
      synthetic construct

<400> SEQUENCE: 24

Glu Asp Ala Leu Ala Phe Ala Leu Leu Pro Leu Ala Ala Ala Cys Ala
  1               5                  10                  15

Arg Thr Pro Leu Ser Asn Phe Asn Val Gly Ala Ile Ala Arg Gly Val
             20                  25                  30

Ser Gly Thr Trp Tyr Phe Gly Ala Asn Met Glu Phe Ile Gly Ala Thr
         35                  40                  45

Met Gln Gln Thr Val His Ala Glu Gln Ser Ala Ile Ser His Ala Trp
     50                  55                  60

Leu Ser Gly Glu Lys Ala Leu Ala Ala Ile Thr Val Asn Tyr Thr Pro
 65                  70                  75                  80

Cys Gly His Cys Arg Gln Phe Met Asn Glu Leu Asn Ser Gly Leu Asp
```

```
                    85                  90                  95

Leu Arg Ile His Leu Pro Gly Arg Glu Ala His Ala Leu Arg Asp Tyr
                100                 105                 110

Leu Pro Asp Ala Phe Gly Pro Lys Asp Leu Glu
        115                 120

<210> SEQ ID NO 25
<211> LENGTH: 135
<212> TYPE: PRT
<213> ORGANISM: Artificial Sequence
<220> FEATURE:
<223> OTHER INFORMATION: Description of Artificial Sequences; note =
      synthetic construct

<400> SEQUENCE: 25

Met Thr Ser Glu Lys Gly Pro Ser Thr Gly Asp Pro Thr Leu Arg Arg
 1               5                  10                  15

Arg Ile Glu Pro Trp Glu Phe Asp Val Phe Tyr Asp Pro Arg Glu Leu
             20                  25                  30

Arg Lys Glu Ala Cys Leu Leu Tyr Glu Ile Lys Trp Gly Met Ser Arg
         35                  40                  45

Lys Ile Trp Arg Ser Ser Gly Lys Asn Thr Thr Asn His Val Glu Val
     50                  55                  60

Asn Phe Ile Lys Lys Phe Thr Ser Glu Arg Asp Phe His Pro Ser Ile
 65                  70                  75                  80

Ser Cys Ser Ile Thr Trp Phe Leu Ser Trp Ser Pro Cys Trp Glu Cys
                 85                  90                  95

Ser Gln Ala Ile Arg Glu Phe Leu Ser Arg His Pro Gly Val Thr Leu
                100                 105                 110

Val Ile Tyr Val Ala Arg Leu Phe Trp His Met Asp Gln Gln Asn Arg
            115                 120                 125

Gln Gly Leu Arg Asp Leu Val
        130                 135

<210> SEQ ID NO 26
<211> LENGTH: 130
<212> TYPE: PRT
<213> ORGANISM: Artificial Sequence
<220> FEATURE:
<223> OTHER INFORMATION: Description of Artificial Sequences; note =
      synthetic construct

<400> SEQUENCE: 26

Met Asp Ser Leu Leu Met Asn Arg Arg Lys Phe Leu Tyr Gln Phe Lys
 1               5                  10                  15

Asn Val Arg Trp Ala Lys Gly Arg Arg Glu Thr Tyr Leu Cys Tyr Val
             20                  25                  30

Val Lys Arg Arg Asp Ser Ala Thr Ser Phe Ser Leu Asp Phe Gly Tyr
         35                  40                  45

Leu Arg Asn Lys Asn Gly Cys His Val Glu Leu Leu Phe Leu Arg Tyr
     50                  55                  60

Ile Ser Asp Trp Asp Leu Asp Pro Gly Arg Cys Tyr Arg Val Thr Trp
 65                  70                  75                  80

Phe Thr Ser Trp Ser Pro Cys Tyr Asp Cys Ala Arg His Val Ala Asp
                 85                  90                  95

Phe Leu Arg Gly Asn Pro Asn Leu Ser Leu Arg Ile Phe Thr Ala Arg
                100                 105                 110

Leu Tyr Phe Cys Glu Asp Arg Lys Ala Glu Pro Glu Gly Leu Arg Arg
```

```
                115             120             125

Leu His
    130

<210> SEQ ID NO 27
<211> LENGTH: 138
<212> TYPE: PRT
<213> ORGANISM: Artificial Sequence
<220> FEATURE:
<223> OTHER INFORMATION: Description of Artificial Sequences; note =
      synthetic construct

<400> SEQUENCE: 27

Met Lys Pro His Phe Arg Asn Thr Val Glu Arg Met Tyr Arg Asp Thr
1               5                   10                  15

Phe Ser Tyr Asn Phe Tyr Asn Arg Pro Ile Leu Ser Arg Arg Asn Thr
            20                  25                  30

Val Trp Leu Cys Tyr Glu Val Lys Tyr Lys Gly Pro Ser Arg Pro Pro
        35                  40                  45

Leu Asp Ala Lys Ile Phe Arg Gly Gln Val Tyr Ser Glu Leu Lys His
    50                  55                  60

Pro Glu Met Arg Phe Glu His Trp Phe Ser Lys Trp Arg Lys Leu His
65                  70                  75                  80

Arg Asp Gln Glu Tyr Glu Val Thr Trp Tyr Ile Ser Trp Ser Pro Cys
                85                  90                  95

Thr Lys Cys Thr Arg Asp Met Ala Thr Phe Leu Ala Glu Asp Pro Lys
            100                 105                 110

Val Thr Leu Thr Ile Phe Val Ala Arg Leu Tyr Tyr Phe Trp Asp Pro
        115                 120                 125

Asp Tyr Gln Glu Ala Leu Arg Ser Leu Cys
    130                 135

<210> SEQ ID NO 28
<211> LENGTH: 121
<212> TYPE: PRT
<213> ORGANISM: Artificial Sequence
<220> FEATURE:
<223> OTHER INFORMATION: Description of Artificial Sequences; note =
      synthetic construct

<400> SEQUENCE: 28

Glu Pro Trp Val Arg Gly Arg His Glu Thr Tyr Leu Cys Tyr Glu Val
1               5                   10                  15

Glu Arg Met His Asn Asp Thr Trp Val Leu Leu Asn Gln Arg Arg Gly
            20                  25                  30

Phe Leu Cys Asn Gln Ala Pro His Lys His Gly Phe Leu Glu Gly Arg
        35                  40                  45

His Ala Glu Leu Cys Phe Leu Asp Val Ile Pro Phe Trp Lys Leu Asp
    50                  55                  60

Leu Asp Gln Asp Tyr Arg Val Thr Cys Phe Thr Ser Trp Ser Pro Cys
65                  70                  75                  80

Phe Ser Cys Ala Gln Glu Met Ala Lys Phe Ile Ser Lys Asn Lys His
                85                  90                  95

Val Ser Leu Cys Ile Phe Thr Ala Arg Ile Tyr Asp Asp Gln Gly Arg
            100                 105                 110

Cys Gln Glu Gly Leu Arg Thr Leu Ala
        115                 120
```

-continued

```
<210> SEQ ID NO 29
<211> LENGTH: 17
<212> TYPE: PRT
<213> ORGANISM: Artificial Sequence
<220> FEATURE:
<223> OTHER INFORMATION: Description of Artificial Sequences; note =
      synthetic construct

<400> SEQUENCE: 29

Ile Lys Pro Leu Leu Met Asp Glu Gln Asp His Gly Tyr Ala Leu Thr
1               5                   10                  15

Gly

<210> SEQ ID NO 30
<211> LENGTH: 8
<212> TYPE: PRT
<213> ORGANISM: Artificial Sequence
<220> FEATURE:
<223> OTHER INFORMATION: Description of Artificial Sequences; note =
      synthetic construct

<400> SEQUENCE: 30

Asn Ser Gly Val Thr Ile Gln Ile
1               5

<210> SEQ ID NO 31
<211> LENGTH: 8
<212> TYPE: PRT
<213> ORGANISM: Artificial Sequence
<220> FEATURE:
<223> OTHER INFORMATION: Description of Artificial Sequences; note =
      synthetic construct

<400> SEQUENCE: 31

Arg Ala Gly Val Gln Ile Ala Ile
1               5

<210> SEQ ID NO 32
<211> LENGTH: 11
<212> TYPE: PRT
<213> ORGANISM: Artificial Sequence
<220> FEATURE:
<223> OTHER INFORMATION: Description of Artificial Sequences; note =
      synthetic construct

<400> SEQUENCE: 32

Lys Arg Asp Gly Pro Arg Ala Thr Met Lys Ile
1               5                   10

<210> SEQ ID NO 33
<211> LENGTH: 8
<212> TYPE: PRT
<213> ORGANISM: Artificial Sequence
<220> FEATURE:
<223> OTHER INFORMATION: Description of Artificial Sequences; note =
      synthetic construct

<400> SEQUENCE: 33

Glu Ala Gly Ala Lys Ile Ser Ile
1               5

<210> SEQ ID NO 34
<211> LENGTH: 142
<212> TYPE: PRT
<213> ORGANISM: Artificial Sequence
<220> FEATURE:
<223> OTHER INFORMATION: Description of Artificial Sequences; note =
      synthetic construct
```

<400> SEQUENCE: 34

```
Met Lys Val Gly Gly Ile Glu Asp Arg Gln Leu Glu Ala Leu Lys Arg
1               5                   10                  15

Ala Ala Leu Lys Ala Cys Glu Leu Ser Tyr Ser Pro Tyr Ser His Phe
            20                  25                  30

Arg Val Gly Cys Ser Ile Leu Thr Asn Asn Asp Val Ile Phe Thr Gly
        35                  40                  45

Ala Asn Val Glu Asn Ala Ser Tyr Ser Asn Cys Ile Cys Ala Glu Arg
    50                  55                  60

Ser Ala Met Ile Gln Val Leu Met Ala Gly His Arg Ser Gly Trp Lys
65                  70                  75                  80

Cys Met Val Ile Cys Gly Asp Ser Glu Asp Gln Cys Val Ser Pro Cys
                85                  90                  95

Gly Val Cys Arg Gln Phe Ile Asn Glu Phe Val Val Lys Asp Phe Pro
            100                 105                 110

Ile Val Met Leu Asn Ser Thr Gly Ser Arg Ser Lys Val Met Thr Met
        115                 120                 125

Gly Glu Leu Leu Pro Met Ala Phe Gly Pro Ser His Leu Asn
130                 135                 140
```

<210> SEQ ID NO 35
<211> LENGTH: 131
<212> TYPE: PRT
<213> ORGANISM: Artificial Sequence
<220> FEATURE:
<223> OTHER INFORMATION: Description of Artificial Sequences; note = synthetic construct

<400> SEQUENCE: 35

```
Met Asn Arg Gln Glu Leu Ile Thr Glu Ala Leu Lys Ala Arg Asp Met
1               5                   10                  15

Ala Tyr Ala Pro Tyr Ser Lys Phe Gln Val Gly Ala Ala Leu Leu Thr
            20                  25                  30

Lys Asp Gly Lys Val Tyr Arg Gly Cys Asn Ile Glu Asn Ala Ala Tyr
        35                  40                  45

Ser Met Cys Asn Cys Ala Glu Arg Thr Ala Leu Phe Lys Ala Val Ser
50                  55                  60

Glu Gly Asp Thr Glu Phe Gln Met Leu Ala Val Ala Ala Asp Thr Pro
65                  70                  75                  80

Gly Pro Val Ser Pro Cys Gly Ala Cys Arg Gln Val Ile Ser Glu Leu
            85                  90                  95

Cys Thr Lys Asp Val Ile Val Val Leu Thr Asn Leu Gln Gly Gln Ile
            100                 105                 110

Lys Glu Met Thr Val Glu Glu Leu Leu Pro Gly Ala Phe Ser Ser Glu
        115                 120                 125

Asp Leu His
    130
```

<210> SEQ ID NO 36
<211> LENGTH: 106
<212> TYPE: PRT
<213> ORGANISM: Artificial Sequence
<220> FEATURE:
<223> OTHER INFORMATION: Description of Artificial Sequences; note = synthetic construct

<400> SEQUENCE: 36

```
Asp Ala Leu Ser Gln Ala Ala Ile Ala Ala Asn Arg Ser His Met
  1               5                  10                  15

Pro Tyr Ser Lys Ser Pro Ser Gly Val Ala Leu Glu Cys Lys Asp Gly
                 20                  25                  30

Arg Ile Phe Ser Gly Ser Tyr Ala Glu Asn Ala Ala Phe Asn Pro Thr
             35                  40                  45

Leu Pro Pro Leu Gln Gly Ala Leu Ile Leu Leu Asn Leu Lys Gly Tyr
         50                  55                  60

Asp Tyr Pro Asp Ile Gln Arg Ala Val Leu Ala Glu Lys Ala Asp Ala
 65                  70                  75                  80

Pro Leu Ile Gln Trp Asp Ala Thr Ser Ala Thr Leu Lys Ala Leu Gly
                 85                  90                  95

Cys His Ser Ile Asp Arg Val Leu Leu Ala
                100                 105
```

<210> SEQ ID NO 37
<211> LENGTH: 135
<212> TYPE: PRT
<213> ORGANISM: Artificial Sequence
<220> FEATURE:
<223> OTHER INFORMATION: Description of Artificial Sequences; note = synthetic construct

<400> SEQUENCE: 37

```
Met Thr Ser Glu Lys Gly Pro Ser Thr Gly Asp Pro Thr Leu Arg Arg
  1               5                  10                  15

Arg Ile Glu Pro Trp Glu Phe Asp Val Phe Tyr Asp Pro Arg Glu Leu
                 20                  25                  30

Arg Lys Glu Ala Cys Leu Leu Tyr Glu Ile Lys Trp Gly Met Ser Arg
             35                  40                  45

Lys Ile Trp Arg Ser Ser Gly Lys Asn Thr Thr Asn His Val Glu Val
         50                  55                  60

Asn Phe Ile Lys Lys Phe Thr Ser Glu Arg Asp Phe His Pro Ser Ile
 65                  70                  75                  80

Ser Cys Ser Ile Thr Trp Phe Leu Ser Trp Ser Pro Cys Trp Glu Cys
                 85                  90                  95

Ser Gln Ala Ile Arg Ser Phe Leu Ser Arg His Pro Gly Val Ile Leu
                100                 105                 110

Val Ile Tyr Val Ala Arg Leu Phe Trp His Asn Asp Gln Gln Asn Arg
            115                 120                 125

Gln Gly Leu Arg Asp Leu Val
        130                 135
```

<210> SEQ ID NO 38
<211> LENGTH: 92
<212> TYPE: PRT
<213> ORGANISM: Artificial Sequence
<220> FEATURE:
<223> OTHER INFORMATION: Description of Artificial Sequences; note = synthetic construct

<400> SEQUENCE: 38

```
Met Arg Ala Ser Glu Tyr Tyr His Cys Trp Arg Asn Phe Val Asn Tyr
  1               5                  10                  15

Pro Pro Gly Asp Glu Ala His Trp Pro Gln Tyr Pro Pro Leu Trp Met
                 20                  25                  30

Met Leu Tyr Ala Leu Glu Leu His Cys Ile Ile Leu Ser Leu Pro Pro
             35                  40                  45
```

Cys Leu Lys Ile Ser Arg Arg Trp Gln Asn His Leu Thr Phe Phe Glu
        50                  55                  60

Leu His Leu Gln Asn Cys His Tyr Gln Thr Ile Pro Pro His Ile Leu
65                  70                  75                  80

Leu Ala Thr Leu Ile His Pro Ser Val Ala Trp Arg
                85                  90

<210> SEQ ID NO 39
<211> LENGTH: 60
<212> TYPE: PRT
<213> ORGANISM: Artificial Sequence
<220> FEATURE:
<223> OTHER INFORMATION: Description of Artificial Sequences; note =
      synthetic construct

<400> SEQUENCE: 39

Met Thr Phe Lys Asp Tyr Phe Tyr Cys Trp Asn Thr Phe Val Glu Asn
1               5                   10                  15

His Glu Arg Thr Phe Lys Ala Trp Glu Gly Leu His Glu Asn Ser Val
            20                  25                  30

Arg Leu Thr Arg Gln Leu Arg Arg Ile Leu Pro Leu Tyr Glu Val
        35                  40                  45

Asp Asp Leu Arg Asp Ala Phe Arg Thr Leu Gly Leu
    50                  55                  60

<210> SEQ ID NO 40
<211> LENGTH: 57
<212> TYPE: PRT
<213> ORGANISM: Artificial Sequence
<220> FEATURE:
<223> OTHER INFORMATION: Description of Artificial Sequences; note =
      synthetic construct

<400> SEQUENCE: 40

Met Asn Tyr Asp Glu Phe Gln His Cys Trp Ser Lys Phe Val Tyr Ser
1               5                   10                  15

Gln Arg Glu Leu Phe Glu Pro Trp Asn Asn Leu Pro Lys Tyr Tyr Ile
            20                  25                  30

Leu Leu His Ile Met Leu Gly Glu Ile Leu Arg His Ser Met Asp Pro
        35                  40                  45

Pro Thr Phe Thr Phe Asn Phe Asn Asn
    50                  55

<210> SEQ ID NO 41
<211> LENGTH: 48
<212> TYPE: PRT
<213> ORGANISM: Artificial Sequence
<220> FEATURE:
<223> OTHER INFORMATION: Description of Artificial Sequences; note =
      synthetic construct

<400> SEQUENCE: 41

Met Thr Tyr Ser Glu Phe Lys His Cys Trp Asp Thr Phe Val Asp His
1               5                   10                  15

Gln Gly Cys Pro Phe Gln Pro Trp Asp Gly Leu Asp Glu His Ser Gln
            20                  25                  30

Asp Leu Ser Gly Arg Leu Arg Ala Ile Leu Gln Asn Gly Glu Asn
        35                  40                  45

<210> SEQ ID NO 42
<211> LENGTH: 40
<212> TYPE: PRT

```
<213> ORGANISM: Artificial Sequence
<220> FEATURE:
<223> OTHER INFORMATION: Description of Artificial Sequences; note =
      synthetic construct
<221> NAME/KEY: VARIANT
<222> LOCATION: (12)...(27)
<223> OTHER INFORMATION: Xaa can be any amino acid

<400> SEQUENCE: 42

Thr Asn His Val Glu Val Asn Phe Ile Lys Lys Xaa Xaa Xaa Xaa
1               5                   10                  15

Xaa Xaa Xaa Xaa Xaa Xaa Xaa Xaa Xaa Xaa Xaa Trp Phe Leu Ser Trp
                20                  25                  30

Ser Pro Cys Trp Glu Cys Ser Gln
        35                  40

<210> SEQ ID NO 43
<211> LENGTH: 39
<212> TYPE: PRT
<213> ORGANISM: Artificial Sequence
<220> FEATURE:
<223> OTHER INFORMATION: Description of Artificial Sequences; note =
      synthetic construct
<221> NAME/KEY: VARIANT
<222> LOCATION: (12)...(26)
<223> OTHER INFORMATION: Xaa can be any amino acid

<400> SEQUENCE: 43

Gly Cys His Val Glu Leu Leu Phe Leu Arg Tyr Xaa Xaa Xaa Xaa Xaa
1               5                   10                  15

Xaa Xaa Xaa Xaa Xaa Xaa Xaa Xaa Xaa Xaa Trp Phe Thr Ser Trp Ser
                20                  25                  30

Pro Cys Tyr Asp Cys Ala Arg
        35

<210> SEQ ID NO 44
<211> LENGTH: 40
<212> TYPE: PRT
<213> ORGANISM: Artificial Sequence
<220> FEATURE:
<223> OTHER INFORMATION: Description of Artificial Sequences; note =
      synthetic construct
<221> NAME/KEY: VARIANT
<222> LOCATION: (12)...(27)
<223> OTHER INFORMATION: Xaa can be any amino acid

<400> SEQUENCE: 44

Lys Tyr His Pro Glu Met Arg Phe Phe His Trp Xaa Xaa Xaa Xaa Xaa
1               5                   10                  15

Xaa Xaa Xaa Xaa Xaa Xaa Xaa Xaa Xaa Xaa Xaa Trp Tyr Ile Ser Trp
                20                  25                  30

Ser Pro Cys Thr Lys Cys Thr Arg
        35                  40

<210> SEQ ID NO 45
<211> LENGTH: 39
<212> TYPE: PRT
<213> ORGANISM: Artificial Sequence
<220> FEATURE:
<223> OTHER INFORMATION: Description of Artificial Sequences; note =
      synthetic construct
<221> NAME/KEY: VARIANT
<222> LOCATION: (12)...(26)
<223> OTHER INFORMATION: Xaa can be any amino acid

<400> SEQUENCE: 45
```

```
Gly Arg His Ala Glu Leu Cys Phe Leu Asp Val Xaa Xaa Xaa Xaa
1               5                   10                  15

Xaa Xaa Xaa Xaa Xaa Xaa Xaa Xaa Xaa Cys Phe Thr Ser Trp Ser
            20                  25                  30

Pro Cys Phe Ser Cys Ala Gln
        35
```

<210> SEQ ID NO 46
<211> LENGTH: 35
<212> TYPE: PRT
<213> ORGANISM: Artificial Sequence
<220> FEATURE:
<223> OTHER INFORMATION: Description of Artificial Sequences; note = synthetic construct
<221> NAME/KEY: VARIANT
<222> LOCATION: (12)...(22)
<223> OTHER INFORMATION: Xaa can be any amino acid

<400> SEQUENCE: 46

```
Thr Val His Ala Glu Gln Ser Ala Ile Ser His Xaa Xaa Xaa Xaa
1               5                   10                  15

Xaa Xaa Xaa Xaa Xaa Xaa Xaa Ile Thr Val Asn Tyr Thr Pro Cys Gly His
            20                  25                  30

Cys Arg Gln
        35
```

<210> SEQ ID NO 47
<211> LENGTH: 43
<212> TYPE: PRT
<213> ORGANISM: Artificial Sequence
<220> FEATURE:
<223> OTHER INFORMATION: Description of Artificial Sequences; note = synthetic construct
<221> NAME/KEY: VARIANT
<222> LOCATION: (12)...(30)
<223> OTHER INFORMATION: Xaa can be any amino acid

<400> SEQUENCE: 47

```
Cys Ile Cys Ala Glu Arg Ser Ala Met Ile Gln Xaa Xaa Xaa Xaa
1               5                   10                  15

Xaa Xaa Xaa Xaa Xaa Xaa Xaa Xaa Xaa Xaa Xaa Xaa Xaa Xaa Glu Asp
            20                  25                  30

Gln Cys Val Ser Pro Cys Gly Val Cys Arg Gln
        35                  40
```

<210> SEQ ID NO 48
<211> LENGTH: 11
<212> TYPE: PRT
<213> ORGANISM: Artificial Sequence
<220> FEATURE:
<223> OTHER INFORMATION: Description of Artificial Sequences; note = synthetic construct

<400> SEQUENCE: 48

```
Thr Asn His Val Glu Val Asn Phe Ile Lys Lys
1               5                   10
```

<210> SEQ ID NO 49
<211> LENGTH: 13
<212> TYPE: PRT
<213> ORGANISM: Artificial Sequence
<220> FEATURE:
<223> OTHER INFORMATION: Description of Artificial Sequences; note = synthetic construct

<400> SEQUENCE: 49

```
Trp Phe Leu Ser Trp Ser Pro Cys Trp Glu Cys Ser Gln
1               5                   10
```

<210> SEQ ID NO 50
<211> LENGTH: 11
<212> TYPE: PRT
<213> ORGANISM: Artificial Sequence
<220> FEATURE:
<223> OTHER INFORMATION: Description of Artificial Sequences; note =
      synthetic construct

<400> SEQUENCE: 50

```
Gly Cys His Val Glu Leu Leu Phe Leu Arg Tyr
1               5                   10
```

<210> SEQ ID NO 51
<211> LENGTH: 13
<212> TYPE: PRT
<213> ORGANISM: Artificial Sequence
<220> FEATURE:
<223> OTHER INFORMATION: Description of Artificial Sequences; note =
      synthetic construct

<400> SEQUENCE: 51

```
Trp Phe Thr Ser Trp Ser Pro Cys Tyr Asp Cys Ala Arg
1               5                   10
```

<210> SEQ ID NO 52
<211> LENGTH: 11
<212> TYPE: PRT
<213> ORGANISM: Artificial Sequence
<220> FEATURE:
<223> OTHER INFORMATION: Description of Artificial Sequences; note =
      synthetic construct

<400> SEQUENCE: 52

```
Ala Ala His Ala Glu Glu Ala Phe Phe Asn Thr
1               5                   10
```

<210> SEQ ID NO 53
<211> LENGTH: 13
<212> TYPE: PRT
<213> ORGANISM: Artificial Sequence
<220> FEATURE:
<223> OTHER INFORMATION: Description of Artificial Sequences; note =
      synthetic construct

<400> SEQUENCE: 53

```
Trp Tyr Val Ser Ser Ser Pro Cys Ala Ala Cys Ala Asp
1               5                   10
```

<210> SEQ ID NO 54
<211> LENGTH: 11
<212> TYPE: PRT
<213> ORGANISM: Artificial Sequence
<220> FEATURE:
<223> OTHER INFORMATION: Description of Artificial Sequences; note =
      synthetic construct

<400> SEQUENCE: 54

```
His Cys His Ala Glu Arg Cys Phe Leu Ser Trp
1               5                   10
```

<210> SEQ ID NO 55
<211> LENGTH: 13
<212> TYPE: PRT
<213> ORGANISM: Artificial Sequence

```
<220> FEATURE:
<223> OTHER INFORMATION: Description of Artificial Sequences; note =
      synthetic construct

<400> SEQUENCE: 55

Trp Tyr Thr Ser Trp Ser Pro Cys Pro Asp Cys Ala Gly
1               5                   10

<210> SEQ ID NO 56
<211> LENGTH: 11
<212> TYPE: PRT
<213> ORGANISM: Artificial Sequence
<220> FEATURE:
<223> OTHER INFORMATION: Description of Artificial Sequences; note =
      synthetic construct

<400> SEQUENCE: 56

Gly Arg His Ala Glu Leu Cys Phe Leu Asp Val
1               5                   10

<210> SEQ ID NO 57
<211> LENGTH: 13
<212> TYPE: PRT
<213> ORGANISM: Artificial Sequence
<220> FEATURE:
<223> OTHER INFORMATION: Description of Artificial Sequences; note =
      synthetic construct

<400> SEQUENCE: 57

Cys Phe Thr Ser Trp Ser Pro Cys Phe Ser Cys Ala Gln
1               5                   10

<210> SEQ ID NO 58
<211> LENGTH: 11
<212> TYPE: PRT
<213> ORGANISM: Artificial Sequence
<220> FEATURE:
<223> OTHER INFORMATION: Description of Artificial Sequences; note =
      synthetic construct

<400> SEQUENCE: 58

Lys Tyr His Pro Glu Met Arg Phe Phe His Trp
1               5                   10

<210> SEQ ID NO 59
<211> LENGTH: 13
<212> TYPE: PRT
<213> ORGANISM: Artificial Sequence
<220> FEATURE:
<223> OTHER INFORMATION: Description of Artificial Sequences; note =
      synthetic construct

<400> SEQUENCE: 59

Trp Tyr Ile Ser Trp Ser Pro Cys Thr Lys Cys Thr Arg
1               5                   10

<210> SEQ ID NO 60
<211> LENGTH: 11
<212> TYPE: PRT
<213> ORGANISM: Artificial Sequence
<220> FEATURE:
<223> OTHER INFORMATION: Description of Artificial Sequences; note =
      synthetic construct

<400> SEQUENCE: 60

Thr Val His Ala Glu Gln Ser Ala Ile Ser His
1               5                   10
```

```
<210> SEQ ID NO 61
<211> LENGTH: 13
<212> TYPE: PRT
<213> ORGANISM: Artificial Sequence
<220> FEATURE:
<223> OTHER INFORMATION: Description of Artificial Sequences; note =
      synthetic construct

<400> SEQUENCE: 61

Ile Thr Val Asn Tyr Thr Pro Cys Gly His Cys Arg Gln
 1               5                  10

<210> SEQ ID NO 62
<211> LENGTH: 11
<212> TYPE: PRT
<213> ORGANISM: Artificial Sequence
<220> FEATURE:
<223> OTHER INFORMATION: Description of Artificial Sequences; note =
      synthetic construct

<400> SEQUENCE: 62

Val Cys His Ala Glu Leu Asn Ala Ile Met Asn
 1               5                  10

<210> SEQ ID NO 63
<211> LENGTH: 13
<212> TYPE: PRT
<213> ORGANISM: Artificial Sequence
<220> FEATURE:
<223> OTHER INFORMATION: Description of Artificial Sequences; note =
      synthetic construct

<400> SEQUENCE: 63

Met Tyr Val Ala Leu Phe Pro Cys Asn Glu Cys Ala Lys
 1               5                  10
```

What is claimed is:

1. A method of screening for an antiviral agent, comprising
   a) detecting the expression level of CEM15 in a first blood sample from a subject having human immunodeficiency virus (HIV)
   b) administering to the subject an agent to be screened; and
   c) detecting the expression level of CEM15 in a second blood sample from the subject, wherein the second blood sample is obtained after the agent is administered, wherein an increased expression level of CEM15 in the second blood sample compared to the first blood sample indicates that the agent is an antiviral agent.

2. The method of claim 1, wherein detecting the expression level of CEM15 in the first blood sample and in the second blood sample comprises detecting the level of CEM mRNA.

3. The method of claim 1, wherein detecting the expression level of CEM15 in the first blood sample and in the second blood sample comprises detecting the level of CEM15 protein.

4. The method of claim 1, wherein detecting the expression level of CEM15 in the first blood sample and in the second blood sample comprises detecting the expression level of CEM15 in a peripheral blood mononuclear cell (PBMC).

* * * * *